(12) United States Patent
Yamazaki et al.

(10) Patent No.: US 9,234,223 B2
(45) Date of Patent: Jan. 12, 2016

(54) METHOD FOR PRODUCING L-CYSTEINE

(75) Inventors: Shunsuke Yamazaki, Kawasaki (JP); Gen Nonaka, Kawasaki (JP); Kazuhiro Takumi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 13/431,104

(22) Filed: Mar. 27, 2012

(65) Prior Publication Data

US 2012/0252076 A1 Oct. 4, 2012

Related U.S. Application Data

(60) Provisional application No. 61/470,573, filed on Apr. 1, 2011.

(51) Int. Cl.
C12P 13/12 (2006.01)
C12N 9/02 (2006.01)
C12N 9/10 (2006.01)
C12N 9/88 (2006.01)

(52) U.S. Cl.
CPC .............. C12P 13/12 (2013.01); C12N 9/001 (2013.01); C12N 9/0051 (2013.01); C12N 9/1007 (2013.01); C12N 9/88 (2013.01); C12Y 103/01076 (2013.01); C12Y 108/99001 (2013.01); C12Y 201/01107 (2013.01); C12Y 499/01004 (2013.01); C12Y 402/99 (2013.01)

(58) Field of Classification Search
None
See application file for complete search history.

(56) References Cited

U.S. PATENT DOCUMENTS

| | | | |
|---|---|---|---|
| 5,856,148 A | 1/1999 | Burlingame | |
| 5,972,663 A | 10/1999 | Winterhalter et al. | |
| 6,218,168 B1 | 4/2001 | Leinfelder et al. | |
| 7,759,094 B2 | 7/2010 | Rieping | |
| 8,008,048 B2 | 8/2011 | Nonaka et al. | |
| 2003/0077766 A1 | 4/2003 | Takagi et al. | |
| 2005/0009162 A1 | 1/2005 | Maier et al. | |
| 2005/0069994 A1 | 3/2005 | Ptitsyn et al. | |
| 2005/0112731 A1 | 5/2005 | Kashiwagi et al. | |
| 2005/0124049 A1* | 6/2005 | Ziyatdinov et al. | 435/113 |
| 2005/0221453 A1 | 10/2005 | Takagi et al. | |
| 2007/0026505 A1 | 2/2007 | Madden et al. | |
| 2008/0076163 A1 | 3/2008 | Takagi et al. | |
| 2009/0226984 A1 | 9/2009 | Nonaka et al. | |
| 2009/0298136 A1 | 12/2009 | Zelder et al. | |
| 2010/0047879 A1 | 2/2010 | Figge et al. | |
| 2010/0209977 A1 | 8/2010 | Takumi et al. | |
| 2010/0216196 A1 | 8/2010 | Nonaka et al. | |
| 2010/0233765 A1 | 9/2010 | Nonaka et al. | |
| 2011/0033902 A1 | 2/2011 | Nonaka et al. | |
| 2011/0177566 A1 | 7/2011 | Savrasova et al. | |
| 2011/0212496 A1 | 9/2011 | Takikawa et al. | |
| 2012/0190084 A1 | 7/2012 | Schneider et al. | |

FOREIGN PATENT DOCUMENTS

| | | |
|---|---|---|
| CA | 2386539 A1 | 4/2001 |
| CA | 2386539 C | 4/2007 |
| EP | 2479279 | 7/2012 |
| JP | 11-155571 A | 6/1999 |
| JP | 2002-233384 A | 8/2002 |
| JP | 2003-511086 | 3/2003 |
| JP | 2003-169668 A | 6/2003 |
| JP | 2005-245311 A | 9/2005 |
| JP | 2005-287333 A | 10/2005 |
| JP | 2009-501550 | 1/2009 |
| JP | 2010-022215 | 2/2010 |
| WO | WO03/006666 A2 | 1/2003 |
| WO | WO2005/108561 A2 | 11/2005 |
| WO | WO2006/082254 A2 | 8/2006 |
| WO | WO2007/077041 A1 | 7/2007 |
| WO | WO2008/127240 A1 | 10/2008 |
| WO | WO2009/043372 A1 | 4/2009 |

OTHER PUBLICATIONS

Stoupe et al., Sulfite reductase hemoprotein in Handbook of Metalloproteins (Messerschmidt et al., eds.), 2001, 471-485.*
Kredich, The molecular basis for positive regulation of cys promoters in *Salmonella typhimurium* and *Escherichia coli*, Mol. Microbiol., 1992, 6, 2747-53.*
Chambers et al., Cysteine and S-sulphocysteine biosynthesis in bacteria, Arch. Mikrobiol., 1971, 77, 165-84.*
Wu et al., High-level expression of *Escherichia coli* NADPH-sulfite reductase: requirement for a cloned cysG plasmid to overcome limiting siroheme cofactor, J. Bacteriol., 1991, 173, 325-33.*
Ostrowski et al., Characterization of the cysJIH Regions of *Salmonella tryphimurium* and *Escherichia coli* B, J. Biol. Chem., 1989, 264, 15726-37.*
Ostrowski et al., Characterization of the flavoprotein moieties of NADPH-sulfite reductase from *Salmonella typhimurium* and *Escherichia coli*, J. Biol. Chem., 1989, 264, 15796-15808.*
Wahl et al., Molecular hybridization of immobilized nucleic acids, Methods Enz., 1987, 152, 399-407.*
Kredich, Biosynthesis of Cysteine in *Escherichia coli* and *Salmonella* Cellular and Molecular Biology, Neidhardt, F.C., Ed., 2nd Edition, vol. 1, ASM Press, 1996, pp. 514-527.*
International Search Report for PCT Patent App. No. PCT/JP2012/058696 (Jul. 3, 2012).
Supplementary European Search Report for European Patent App. No. 12767953.8 (Nov. 24, 2014).
Warren, M. J., et al., "The *Escherichia coil* cysG gene encodes 5-adenosylnnethione-dependent uroporphyrinogen III methylase," Biochem. J. 1990;265:725-729.

(Continued)

*Primary Examiner* — Robert Mondesi
*Assistant Examiner* — Todd M Epstein
(74) *Attorney, Agent, or Firm* — Shelly Guest Cermak; Cermak Nakajima & McGowan LLP

(57) ABSTRACT

A method for producing L-cysteine and the like is provided by developing a novel technique for improving bacterial L-cysteine-producing ability. The method includes the steps of culturing a bacterium belonging to the genus *Escherichia* which has L-cysteine-producing ability, and in which expression of a gene involved in sulfite reduction is enhanced, in a medium containing thiosulfate, and collecting L-cysteine, a related substance thereof, or a mixture thereof which accumulate in the medium.

5 Claims, 3 Drawing Sheets

(56) References Cited

OTHER PUBLICATIONS

Dassler, T., et al., "Identification of a major facilitator protein from *Escherichia coli* involved in efflux of metabolites of the cysteine pathway," Mol. Microbiol. 2000;36(5):1101-1112.

Eschenbrenner, M., et al., "The Flavin Reductase Activity of the Flavoprotein Component of Sulfite Reductase from *Escherichia coli*," J. Biol. Chem. 1995;270(35):20550-20555.

Gaudu, P., et al., "The NADPH:sulfite reductase of *Escherichia coli* is paraquat reductase," Eur. J. Biochem. 1994;226:459-463.

Li, C., et al., "Cloning of the 3'-phosphoadenylyl sulfate reductase and sulfite reductase genes and *Escherichia coli* K-12," Gene 1987;53:227-234.

MacDonald, H., et al., "Molecular cloning and functional analysis of the cysG and nirB genes of *Escherichia coli* K12, two closely-linked genes required for NADH-dependent nitrite reductase activity," Mol. Gen. Genet. 1985;200:328-334.

Peakman, T., et al., "Nucleotide sequence, organisation and structural analysis of the products of genes in the nirB-cysG region of the *Escherichia coli* K-12 chromosome," Eur. J. Biochem. 1990;191:315-323.

Spencer, J. B., et al., "The *Escherichia coli* cysG gene encodes the multifunctional protein, siroheme synthase," FEBS Lett. 1993;335(1):57-60.

\* cited by examiner

Figure 2

Sequence of native promoter Pnlp0

```
                              -35(Pnlp2)                    -10(Pnlp2)
aaaacgtgaggaaatacctggattttcctggttattttgccgcaggtcagcgtatcgtg -35(Pnlp1)              -10(Pnlp1)    transcription start site
aagatcttttccagtgttcagtagggtgccttgcacggtaattatgtcactggttattaa M  S
ccaattttcctggggataaatgagc
```

Sequence of mutant promoter Pnlp8

```
                              -35(Pnlp2)                    -10(Pnlp2)
aaaacgtgaggaaatacctggattttcctggttattttgccgcaggtcagcgtataatg -35(Pnlp1)              -10(Pnlp1)    transcription start site
aagatcttttccagtgttgacaagggtgccttgcacggttataatgtcactggttattaa M  S
ccaattttcctggggataaatgagc
```

METHOD FOR PRODUCING L-CYSTEINE

This application claims priority under 35 U.S.C. §119 to U.S. Provisional Patent Application No. 61/470,573, filed Apr. 1, 2011, the entirety of which is incorporated by reference herein. Also, the Sequence Listing filed electronically herewith is hereby incorporated by reference (File name: 2012-03-27T_US-464_Seq_List; File size: 88 KB; Date recorded: Mar. 27, 2012).

BACKGROUND OF THE INVENTION

1. Field of the Invention

The present invention relates to a method for producing L-cysteine or a related substance thereof. L-cysteine and related substances thereof are used in the fields of drugs, cosmetics, and foods.

2. Brief Description of the Related Art

L-cysteine is conventionally obtained by extraction from keratin-containing substances such as hair, horns, and feathers, or converting the precursor DL-2-aminothiazoline-4-carboxylic acid using a microbial enzyme. L-cysteine can also be produced on a large scale by an immobilized enzyme method utilizing a novel enzyme. Furthermore, L-cysteine can also be produced by fermentation utilizing a microorganism.

The ability of a microorganism to produce L-cysteine can be improved by enhancing the activity of an enzyme of the L-cysteine biosynthesis pathway, or an activity of an enzyme involved in generation of a compound which acts as a substrate of that pathway, such as L-serine. Microorganisms which are able to produce L-cysteine include, for example, a coryneform bacterium in which intracellular serine acetyltransferase activity is increased (Japanese Patent Laid-open (Kokai) No. 2002-233384). L-cysteine-producing ability can also be increased by incorporating a serine acetyltransferase which has been mutated so that feedback inhibition by L-cysteine is attenuated (Japanese Patent Laid-open (Kokai) No. 11-155571, U.S. Patent Published Application No. 20050112731 and U.S. Pat. No. 6,218,168). A mutant serA gene coding for a mutant 3-phosphoglycerate dehydrogenase of which feedback inhibition by serine is attenuated is also known, and use thereof in production of L-cysteine by *Escherichia coli* has been suggested (U.S. Pat. No. 5,856,148 and U.S. Patent Published Application No. 20050009162).

Furthermore, L-cysteine-producing ability of a microorganism can also be improved by suppressing the system which acts to decompose L-cysteine. Microorganisms in which this system has been suppressed, and the L-cysteine-producing ability is enhanced, include coryneform bacteria or *Escherichia* bacteria in which activity of cystathionine-β-lyase (Japanese Patent Laid-open (Kokai) No. 11-155571), tryptophanase (Japanese Patent Laid-open (Kokai) No. 2003-169668), or O-acetylserine sulfhydrylase B (Japanese Patent Laid-open (Kokai) No. 2005-245311) is attenuated or deleted.

Moreover, L-cysteine-producing ability of a microorganism can also be improved by enhancing the L-cysteine-secreting ability. For example, techniques have been reported of enhancing L-cysteine-producing ability by enhancing expression of the ydeD gene (Dassler et al., Mol. Microbiol., 36, 1101-1112 (2000)), yfiK gene (Macdonald and Cole, Molecular and General Genetics, 200(2):328-334 (1985)), or yeaS gene (Warren et al., Biochemical Journal, 265(3):725-729 (1990)), which codes for a protein that participates in secretion of L-cysteine. Furthermore, techniques have been reported of enhancing L-cysteine-producing ability by enhancing expression of the mar locus, emr locus, acr locus, cmr locus, mex gene, bmr gene or qacA gene (U.S. Pat. No. 5,972,663), or emrAB, emrKY, yojIH, acrEF, bcr or cusA gene (Japanese Patent Laid-open (Kokai) No. 2005-287333). These loci/genes encode proteins which are responsible for secreting a substance which is cytotoxic from the cells.

L-cysteine is a sulfur-containing amino acid, and therefore, metabolism of a sulfur source is involved in the production of L-cysteine. The biosynthesis pathway of L-cysteine when glucose is the carbon source and the sulfate or thiosulfate ion is the sulfur source, and examples of genes involved in that pathway are shown in FIG. 1.

Sulfite reductase is an enzyme that catalyzes, in the sulfate reduction pathway (Frederick C., Neidhardt et al., *Escherichia Coli* and *Salmonella* Cellular and Molecular Biology, 2nd Edition, Vol. 1, ASM Press, 514-527) in which sulfate ion ($SO_4^{2-}$) is converted into sulfide ion ($-S^{2-}$), the reaction of reducing sulfite ion ($-SO_3^{2-}$) into sulfide ion ($-S^{2-}$) as the final step. The sulfide ion generated from the sulfate ion via the sulfate reduction pathway reacts with O-acetylserine (OAS) to generate L-cysteine. That is, when L-cysteine is produced with sulfate ions as the sulfur source, the sulfite reductase is considered to be one of the enzymes that participate in the L-cysteine biosynthesis. It is known that the sulfite reductase of *Escherichia coli* has an $\alpha_8\beta_4$ complex structure which includes α subunits encoded by the cysJ gene and β subunits encoded by the cysI gene. Furthermore, the cysG gene codes for the biosynthesis enzyme of siroheme, which is a cofactor of the sulfite reductase β subunit. The cysJ gene and the cysI gene are present on the same operon, whereas the cysG gene is on a different site of the genome. The details of the cysJ gene, the cysI gene and the proteins encoded by these genes are described in Ostrowski et al., Journal of Biological Chemistry, 264(27):15796-15808 (1989), Li et al., Gene, 53(2-3):227-234 (1987), Gaudu and Fontecave, European Journal of Biochemistry, 226 (2):459-463 (1994), Eschenbrenner et al., Journal of Biological Chemistry, 270(35): 20550-20555 (1995) and Ostrowski et al., Journal of Biological Chemistry, 264(26):15726-15737 (1989). Furthermore, the details of the cysG gene and the protein encoded by this gene are described in Peakman et al., European Journal of Biochemistry, 191(2):315-323 (1990), Macdonald and Cole, Molecular and General Genetics, 200(2):328-334 (1985), Warren et al., Biochemical Journal, 265(3):725-729 (1990) and Spencer et al., FEBS Letters 335(1):57-60 (1993).

Although there has been no report directly linking enhancing expression of the cysG gene, cysJ gene or cysI gene with increased L-cysteine production, an *Escherichia coli* bacteria in which activity of a protein encoded by the cysB gene is enhanced is known as an L-cysteine-producing bacterium (International Patent Publication WO01/27307). Because the protein encoded by the cysB gene positively regulates expression of the cysJIH operon which includes the cysJ gene and cysI gene coding for sulfite reductase, expression of the cysJ gene and cysI gene may be increased in that *Escherichia coli*. On the other hand, expression of the cysG gene is not regulated by the protein encoded by the cysB gene, and enhancement of expression of the cysG gene for L-cysteine production has not been reported.

Furthermore, the effectiveness of enhancing expression of the cysG gene, cysJ gene or cysI gene in the production of amino acids other than L-cysteine has been suggested. For example, enhancing expression of the cys genes including the cysG gene, cysJ gene and cysI gene, is referred to concerning production of L-threonine or L-lysine (U.S. Pat. No. 7,759,094), production of L-threonine (International Patent Publication WO03/006666), and production of L-methionine (U.S. Patent Published Application No. 2009298136 and International Patent Publication WO2008/127240). Furthermore, enhancing expression of the cys genes including the cysJ gene and the cysI gene is also referred to concerning production of L-methionine (International Patent Publication WO2009/043372, International Patent Publication WO2005/108561, International Patent Publication WO2007/077041, and International Patent Publication WO2006/082254). Moreover, enhancing expression of the cysJIH operon including the cysJ gene and the cysI gene is also referred to concerning production of L-methionine (U.S. Patent Published Application No. 20100047879). Furthermore, increasing L-arginine production by enhancing expression of the cysG gene has been reported (U.S. Patent Published Application No. 20050069994).

On the other hand, thiosulfate is metabolized in a pathway other than the sulfate reduction pathway (FIG. 1), and it is not known whether sulfite reductase participates in the metabolism of thiosulfate. Furthermore, all the aforementioned findings concerning production of amino acids fail to suggest that enhancing expression of the cysG gene, cysJ gene or cysI gene can be effective for amino acid production using thiosulfate as the sulfur source. As described above, the relationship between production of an amino acid such as L-cysteine using thiosulfate as the sulfur source and the cysG gene, cysJ gene or cysI gene has not been previously reported.

SUMMARY OF THE INVENTION

An aspect of the present invention is to provide a method for producing L-cysteine, a related substance thereof, or a mixture thereof by developing a novel technique for improving L-cysteine-producing ability of a bacterium.

It is an aspect of the present invention to provide a method of improving production of L-cysteine when thiosulfate is used as the sulfur source, in a bacterium by modifying the bacterium so that expression of a gene involved in the sulfite reduction is increased.

It is an aspect of the present invention to provide a method for producing L-cysteine, a related substance thereof, or a mixture thereof, which comprises:

culturing a bacterium belonging to the genus *Escherichia* in a medium comprising thiosulfate, which bacterium has L-cysteine-producing ability and is modified so that expression of a gene involved in sulfite reduction is increased; and collecting L-cysteine, a related substance thereof, or a mixture thereof from the medium.

It is a further aspect of the present invention to provide a method as described above, wherein the gene involved in sulfite reduction is a gene selected from the group consisting of the cysG gene, the cysJ gene, and the cysI gene.

It is a further aspect of the present invention to provide a method as described above, wherein expression of at least the cysG gene is increased.

It is a further aspect of the present invention to provide a method as described above, wherein expression of the cysG gene, the cysJ gene, and the cysI gene is increased.

It is a further aspect of the present invention to provide a method as described above, wherein expression of the gene involved in sulfite reduction is increased by increasing copy number of the gene involved in sulfite reduction, or by modifying an expression control sequence of the gene.

It is a further aspect of the present invention to provide a method as described above, wherein the bacterium is *Escherichia coli*.

It is a further aspect of the present invention to provide a method as described above, wherein the bacterium further has a characteristic selected from the group consisting of:
(a) biosynthesis system of L-cysteine is enhanced,
(b) secretion system of L-cysteine is enhanced.

It is a further aspect of the present invention to provide a method as described above, wherein the related substance is L-cystine or a thiazolidine derivative.

According to the present invention, L-cysteine-producing ability of a bacterium can be improved when thiosulfate is used as a sulfur source. Furthermore, according to the present invention, L-cysteine, a related substance thereof, or a mixture thereof can be efficiently produced when thiosulfate is used as a sulfur source.

BRIEF DESCRIPTION OF THE DRAWINGS

FIG. 2 shows the nucleotide sequence (SEQ ID NO: 51) of the ligation site of a wild-type promoter Pnlp0 of the nlpD gene and a gene ligated downstream thereof, and the nucleotide sequence (SEQ ID NO: 52) of ligation site of a mutant type promoter Pnlp8 of the nlpD gene and a gene ligated downstream thereof.

DETAILED DESCRIPTION OF THE PREFERRED EMBODIMENTS

<1> Bacterium

Figure 1:
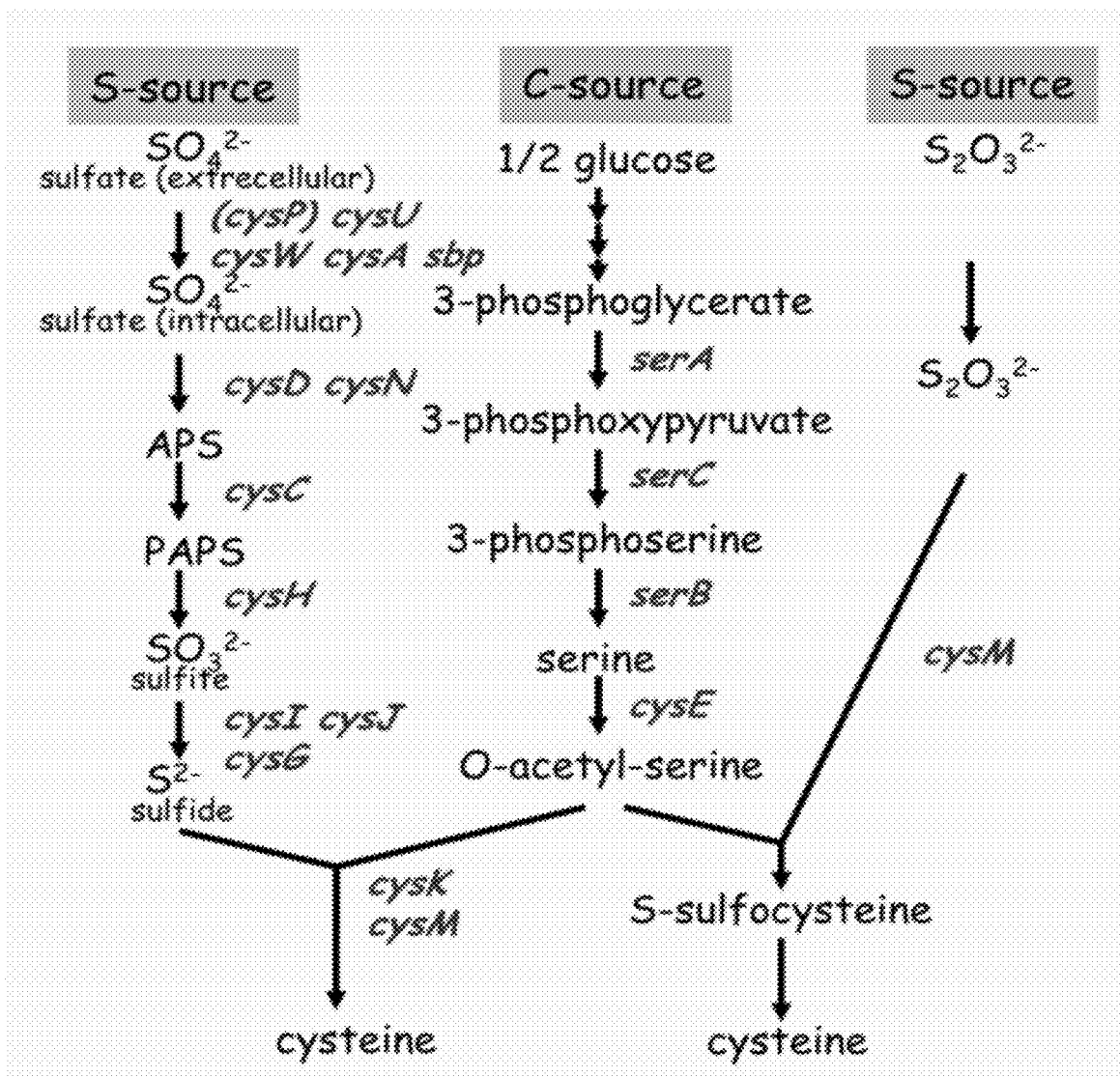
FIG. 1 shows an outline of the biosynthesis pathway of L-cysteine when glucose is used as the carbon source, and sulfate ion or thiosulfate ion is used as the sulfur source, and examples of the genes which are involved.

The bacterium which can be used in accordance with the presently described invention (henceforth also referred to as the bacterium of the present invention) is a bacterium belonging to the genus *Escherichia* which is able to produce L-cysteine, and is modified so that expression of a gene involved in sulfite reduction is increased.

L-cysteine can be in free form, a salt thereof, or a mixture of these. Examples of the salt include, for example, sulfate, hydrochloride, carbonate, ammonium salt, sodium salt, and potassium salt.

The L-cysteine-producing ability can refer to an ability of a bacterium to produce and cause accumulation of L-cysteine, a related substance thereof, or a mixture of these, in the medium or the cells of the bacterium in such an amount that L-cysteine, the related substance thereof, or the mixture of these can be collected from the medium or cells, when the bacterium is cultured in the medium. A bacterium having L-cysteine-producing ability can mean a bacterium that can produce and accumulate L-cysteine, a related substance thereof, or a mixture of these in a medium in a larger amount compared with a wild-type strain or a parent strain. A bacterium having L-cysteine-producing ability can mean a bacterium that can produce and accumulate L-cysteine, a related substance thereof, or a mixture of these in a medium in an amount of 0.05 g/L or more, 0.1 g/L or more, 0.2 g/L or more, or even 0.4 g/L or more.

A portion of the L-cysteine produced by the bacterium can be converted into L-cystine in the medium by formation of a disulfide bond. Further, S-sulfocysteine may be generated by the reaction of L-cysteine and thiosulfate contained in the medium (Szczepkowski T. W., Nature, vol. 182 (1958)). Furthermore, L-cysteine generated in bacterial cells may be condensed with a ketone or aldehyde, for example, pyruvic acid, which is present in the cells, to produce a thiazolidine derivative via a hemithioketal as an intermediate (refer to Japanese Patent No. 2992010). These thiazolidine derivative and hemithioketal may exist as an equilibrated mixture.

Furthermore, L-cysteine can be used as a starting material in the biosyntheses of γ-glutamylcysteine, glutathione, cystathionine, homocysteine, L-methionine, S-adenosylmethionine, and so forth. Therefore, by using a bacterium having an ability to produce any of these compounds via L-cysteine in addition to the ability to produce L-cysteine, these compounds can be produced.

Therefore, the L-cysteine-producing ability is not limited to an ability to produce and accumulate only L-cysteine in a medium or cells, but also includes an ability to produce and accumulate L-cysteine, L-cystine, a derivative of L-cysteine as mentioned above (for example, S-sulfocysteine, a thiazolidine derivative, and a hemithioketal), a compound which is produced via L-cysteine as mentioned above (for example, γ-glutamylcysteine, glutathione, cystathionine, homocysteine, L-methionine, and S-adenosylmethionine), or a mixture of these in the medium or cells, L-cystine, a derivative of L-cysteine as mentioned above, and a compound produced via L-cysteine as mentioned above can be collectively referred to as a related substance of L-cysteine.

The bacterium having L-cysteine-producing ability can inherently have L-cysteine-producing ability, or it may be obtained by modifying a microorganism such as those described below by mutagenesis or a recombinant DNA technique so that it acquires L-cysteine-producing ability.

The bacterium is not particularly limited, so long as it is a bacterium belonging to the genus *Escherichia* and having L-cysteine-producing ability. Specifically, those classified into the genus *Escherichia* according to the taxonomy used in the NCBI (National Center for Biotechnology Information) database (www.ncbi.nlm.nih.gov/Taxonomy/Browser/wwwtax.cgi?id91347) can be used.

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. Examples of *Escherichia* bacteria include, for example, *Escherichia coli*. Specific examples of *Escherichia coli* include the *Escherichia coli* W3110 strain (ATCC 27325), *Escherichia coli* MG1655 strain (ATCC 47076) and so forth, which are derived from the prototype wild-type strain, K12.

These strains are available from, for example, the American Type Culture Collection (Address: P.O. Box 1549, Manassas, Va. 20108, United States of America). That is, registration numbers are given to each of the strains, and the strains can be ordered by using these registration numbers (refer to www.atcc.org/). The registration numbers of the strains are listed in the catalogue of the American Type Culture Collection.

Methods for imparting L-cysteine-producing ability to bacteria belonging to the genus *Escherichia* and methods for enhancing L-cysteine-producing ability of such bacteria are described below.

To impart L-cysteine-producing ability to a bacterium, methods conventionally employed in the breeding of coryneform bacteria, *Escherichia* bacteria, and so forth can be used. Such methods include acquiring an auxotrophic mutant strain, an analogue resistant strain, or a metabolic regulation mutant strain, or constructing a recombinant strain in which an L-cysteine biosynthesis enzyme is overexpressed, and so forth (see "Amino Acid Fermentation", Gakkai Shuppan Center (Ltd.), 1st Edition, published May 30, 1986, pp. 77-100). In the breeding of L-cysteine-producing bacteria, one or more kinds of the above-described properties such as auxotrophy, analogue resistance, and metabolic regulation mutation can be imparted. Also, expression of one or more of the L-cysteine biosynthesis enzymes can be enhanced. Furthermore, imparting such properties as auxotrophy, analogue resistance, and metabolic regulation mutation can be combined with enhancing a biosynthesis enzyme.

An auxotrophic mutant strain, L-cysteine analogue resistant strain, or metabolic regulation mutant strain having L-cysteine-producing ability can be obtained by subjecting a parent strain or wild-type strain to conventional mutagenesis, such as exposure to X-rays or UV irradiation or a treatment with a mutagen such as N-methyl-N'-nitro-N-nitrosoguanidine (MNNG) or ethyl methanesulfonate (EMS), and then selecting a strain exhibiting autotrophy, analogue resistance or a metabolic regulation mutation and having L-cysteine-producing ability from the obtained mutant strains.

Methods for imparting L-cysteine-producing ability to bacteria belonging to the genus *Escherichia* or enhancing L-cysteine-producing ability of such bacteria, and bacteria having L-cysteine-producing ability are specifically exemplified below.

<Impartation or Enhancement of L-Cysteine-Producing Ability, and L-Cysteine-Producing Bacteria>

L-Cysteine-producing ability of a bacterium can be imparted or enhanced by enhancing the biosynthesis system of L-cysteine. "To enhance the biosynthesis system of L-cysteine" can mean, for example, to enhance activity of an enzyme involved in the biosynthesis of L-cysteine. Examples of enzymes involved in the biosynthesis of L-cysteine include enzymes of the L-cysteine biosynthesis pathway and enzymes involved in synthesis of a compound which acts as a substrate in the L-cysteine biosynthesis pathway, such as L-serine, and specific examples include serine acetyltransferase (SAT) and 3-phosphoglycerate dehydrogenase (PGD). Enhancement of an enzymatic activity can be attained by enhancing expression of a gene coding for the objective enzyme, or by enhancing specific activity of the objective enzyme, as described later. Because serine acetyltransferase is inhibited by feedback inhibition by L-cysteine, the enzymatic activity of this enzyme can be enhanced by, in particular, incorporating a mutant type cysE gene coding for serine acetyltransferase of which feedback inhibition is attenuated or eliminated into a bacterium. Furthermore, because 3-phosphoglycerate dehydrogenase is inhibited by feedback inhibition by serine, the enzymatic activity of this enzyme can be enhanced by, in particular, incorporating a mutant type serA gene coding for a mutant 3-phosphoglycerate dehydrogenase of which feedback inhibition is attenuated or eliminated into a bacterium.

Mutant SATs which are derived from *Escherichia coli* and are resistant to feedback inhibition include the following mutations: replacement of the methionine residue at position 256 with a glutamate residue (Japanese Patent Laid-open No. 11-155571), replacement of the methionine residue at position 256 with an isoleucine residue (Denk, D. and Boeck, A., J. General Microbiol., 133, 515-525 (1987)), a mutation in the region from the amino acid residue at position 97 to the amino acid residue at position 273 or deletion of the C-terminus region from the amino acid residue at position 227 (International Patent Publication WO97/15673, U.S. Pat. No. 6,218, 168), one or more mutations in the amino acid sequence corresponding to positions 89 to 96 of wild-type SAT, wherein a mutant SAT including the mutation(s) is desensitized to feedback inhibition by L-cysteine (U.S. Patent Published Application No. 20050112731(A1)), replacement of the Val residue and the Asp residue at positions 95 and 96 of wild-type SAT with Arg residue and Pro residue, respectively (name of the mutant gene: cysE5, U.S. Patent Published Application No. 20050112731(A1)), replacement of the threonine residue at position 167 with an alanine residue (U.S. Pat. No. 6,218,168, U.S. Patent Published Application No. 20050112731(A1)), and so forth.

The gene coding for SAT is not limited to the gene derived from *Escherichia coli*, and any gene coding for a protein having the SAT activity can be used. For example, an SAT isozyme of *Arabidopsis thaliana* desensitized to feedback inhibition by L-cysteine is known, and the gene encoding this SAT can also be used (FEMS Microbiol. Lett., 179, 453-459 (1999)).

Furthermore, the serA5 gene is known to code for a mutant PGD resistant to feedback inhibition by serine (U.S. Pat. No. 6,180,373).

Furthermore, L-cysteine-producing ability of a bacterium can also be improved by enhancing the L-cysteine secretion system. The L-cysteine secretion system can be enhanced by enhancing expression of a gene coding for one or more proteins involved in secretion of L-cysteine. Examples of proteins involved in secretion of L-cysteine include the YdeD protein encoded by the ydeD gene, the YfiK protein encoded by the yfiK gene, and the YeaS protein encoded by the yeaS gene. Therefore, by enhancing expression of the ydeD gene (Dassler et al., Mol. Microbiol., 36, 1101-1112 (2000)), the yfiK gene (Japanese Patent Laid-open (Kokai) No. 2004-49237) or the yeaS gene (European Patent Laid-open No. 1016710), L-cysteine-producing ability can be enhanced. Furthermore, by introducing a mutation into the threonine residue of the position 28, the phenylalanine residue of the position 137, and/or the leucine residue of the position 188 of the YeaS protein, the L-cysteine secretion system is also enhanced, and L-cysteine-producing ability can be enhanced (European Patent Laid-open No. 2218729). Specifically, replacing the threonine residue at position 28 with asparagine residue, replacing the phenylalanine residue at position 137 with serine, glutamine, alanine, histidine, cysteine or glycine residue, and/or replacing the leucine residue at position 188 with glutamine residue in the YeaS protein are particular examples (European Patent Laid-open No. 2218729).

Furthermore, proteins which are able to secrete a substance which is cytotoxic include those involved in secretion of L-cysteine. Therefore, by enhancing expression of a gene coding for any one of them, the L-cysteine secretion system can be enhanced. For example, by increasing expression of the mar locus, emr locus, acr locus, cmr locus, mex gene, bmr gene or qacA gene (U.S. Pat. No. 5,972,663), or emrAB, emrKY, yojIH, acrEF, bcr or cusA gene (Japanese Patent Laid-open (Kokai) No. 2005-287333), which encode proteins which secrete a substance which is cytotoxic from cells, L-cysteine-producing ability can be enhanced.

Furthermore, the L-cysteine-producing ability can also be improved by enhancing the sulfate/thiosulfate transport system. The sulfate/thiosulfate transport system proteins are encoded by the cysPTWAM cluster genes (Japanese Patent Laid-open (Kokai) No. 2005-137369, European Patent No. 1528108).

Furthermore, the L-cysteine-producing ability of a bacterium can be improved by reducing the activity of cysteine desulfhydrase, which contributes to decomposition of L-cysteine. Proteins having the cysteine desulfhydrase activity of *Escherichia coli* include cystathionine-β-lyase encoded by the metC gene (Japanese Patent Laid-open (Kokai) No. 11-155571, Chandra et al., Biochemistry, 21, 3064-3069 (1982)), tryptophanase encoded by the tnaA gene (Japanese Patent Laid-open (Kokai) No. 2003-169668, Austin Newton et al., J. Biol. Chem., 240, 1211-1218 (1965)), O-acetylserine sulfhydrylase B encoded by the cysM gene (Japanese Patent Laid-open (Kokai) No. 2005-245311) and MalY encoded by the malY gene (Japanese Patent Laid-open (Kokai) No. 2005-245311). The enzymatic activity can be reduced by the methods described herein.

The L-cysteine-producing bacterium can have one of the aforementioned properties for improving L-cysteine-producing ability, or two or more of them in any combination. For example, in the L-cysteine-producing bacterium, either the biosynthesis system of L-cysteine or the secretion system of L-cysteine can be enhanced, and both can be enhanced.

Specific examples of L-cysteine-producing bacteria include, but are not limited to, *Escherichia* bacteria such as the *E. coli* JM15 strain transformed with multiple kinds of cysE gene alleles encoding serine acetyltransferase (SAT) resistant to feedback inhibition (U.S. Pat. No. 6,218,168), *E. coli* W3110 strain in which a gene encoding a protein suitable for secretion of a cytotoxic substance is overexpressed (U.S. Pat. No. 5,972,663), *E. coli* in which cysteine desulfhydrase activity is decreased (Japanese Patent Laid-open (Kokai) No. 11-155571), and *E. coli* W3110 strain in which activity of the positive transcriptional control factor of the cysteine regulon encoded by the cysB gene is increased (WO01/27307), *E. coli* having the plasmid pACYC-DES (Japanese Patent Laid-open (Kokai) No. 2005-137369 (U.S. Patent Published Application No. 20050124049(A1), European Patent Laid-open No. 1528108(A1))) containing the ydeD gene, a mutant cysE gene, and a mutant serA5 gene, and so forth. pACYC-DES is a plasmid obtained by inserting the above three kinds of genes into pACYC184, and expression of each of the genes is controlled by the PompA promoter.

The ability to produce compounds biosynthesized from L-cysteine as a starting material, such as γ-glutamylcysteine, glutathione, cystathionine, homocysteine, L-methionine and S-adenosylmethionine, can also be imparted or enhanced by enhancing activity of an enzyme of biosynthesis system of an objective compound, or reducing activity of an enzyme of a pathway branching from the biosynthesis system of an objective compound, or reducing the activity of an enzyme that decomposes an objective compound.

For example, the ability to produce γ-glutamylcysteine can be enhanced by enhancing the γ-glutamylcysteine synthetase activity, and/or reducing the glutathione synthetase activity. Furthermore, the ability to produce glutathione can be imparted or enhanced by enhancing the γ-glutamylcysteine synthetase activity and/or the glutathione synthetase activity. Furthermore, by using a γ-glutamylcysteine synthetase which has been mutated to be resistant to feedback inhibition by glutathione, the ability to produce γ-glutamylcysteine or glutathione can be enhanced. Production of glutathione is described in detail in the overview of Li et al. (Yin Li, Gongyuan Wei, Jian Chen, Appl. Microbiol. Biotechnol., 66:233-242 (2004)).

The ability to produce L-methionine can be imparted or enhanced by imparting L-threonine auxotrophy or norleucine resistance (Japanese Patent Laid-open (Kokai) No. 2000-139471). In *E. coli*, the genes encoding the enzymes involved in the biosynthesis of L-threonine exist as the threonine operon (thrABC), and an L-threonine auxotrophic strain that has lost the biosynthesis ability for L-homoserine and the following compounds can be obtained by, for example, deleting the thrBC moiety. In a norleucine resistant strain, the S-adenosylmethionine synthetase activity can be attenuated, and L-methionine-producing ability can be imparted or enhanced. In *E. coli*, S-adenosylmethionine synthetase is encoded by the metK gene. The ability to produce L-methionine can also be imparted or enhanced by deleting the methionine repressor or enhancing the activity of an enzyme involved in L-methionine biosynthesis, such as homoserine transsuccinylase, cystathionine γ-synthase and aspartokinase-homoserine dehydrogenase II (Japanese Patent Laid-open (Kokai) No. 2000-139471). In *E. coli*, the methionine repressor is encoded by the metJ gene, homoserine transsuccinylase is encoded by the metA gene, cystathionine γ-synthase is encoded by the metB gene, and aspartokinase-homoserine dehydrogenase II is encoded by the metL gene. Furthermore, by using a homoserine transsuccinylase which has been mutated to be resistant to feedback inhibition by L-methionine, the ability to produce L-methionine can also be imparted or enhanced (Japanese Patent Laid-open (Kokai) No. 2000-139471, U.S. Patent Published Application No. 20090029424). Because L-methionine is biosynthesized via L-cysteine as an intermediate, the ability to produce L-methionine can also be improved by improving the ability to produce L-cysteine (Japanese Patent Laid-open (Kokai) No. 2000-139471, U.S. Patent Published Application No. 20080311632). Therefore, to impart or enhance the ability to produce L-methionine, it can also be effective to impart or enhance the ability to produce L-cysteine.

Specific examples of bacteria that produce L-methionine include *E. coli* strains such as AJ11539 (NRRL B-12399), AJ11540 (NRRL B-12400), AJ11541 (NRRL B-12401), AJ11542 (NRRL B-12402) (British Patent No. 2075055), 218 strain resistant to norleucine, which is an analogue of L-methionine (VKPM B-8125, Russian Patent No. 2209248), and 73 strain (VKPM B-8126, Russian Patent No. 2215782).

Furthermore, the strain AJ13425 (FERM P-16808, Japanese Patent Laid-open (Kokai) No. 2000-139471), which is derived from the *E. coli* W3110, can also be used to produce L-methionine. AJ13425 is an L-threonine auxotrophic strain in which the methionine repressor is deleted, intracellular S-adenosylmethionine synthetase activity is attenuated, and intracellular homoserine transsuccinylase activity, cystathionine γ-synthase activity, and aspartokinase-homoserine dehydrogenase II activity are enhanced. AJ13425 was deposited on May 14, 1998 at the National Institute of Bioscience and Human Technology, Agency of Industrial Science and Technology, Ministry of International Trade and Industry (currently National Institute of Advanced Industrial Science and Technology, International Patent Organism Depository, Address: Tsukuba Central 6, 1-1, Higashi 1-Chome, Tsukuba-shi, Ibaraki-ken, 305-8566, Japan), and assigned an accession number of FERM P-16808.

Because cystathionine and homocysteine are intermediates in the L-methionine biosynthesis pathway, it can be effective to partially use the aforementioned L-methionine enhancing methods to enhance production of these substances. Specifically for enhancing cystathionine production, a methionine-auxotrophic mutant strain (Japanese Patent Application No. 2003-010654) and a method of adding cysteine (or raw material for biosynthesis thereof) and/or homoserine (or raw material for biosynthesis thereof) to a fermentation medium (Japanese Patent Laid-open (Kokai) No. 2005-168422) can be used. Since homocysteine is produced by using cystathionine as a precursor, the aforementioned methods for enhancing cystathionine production are also effective for enhancing homocysteine production.

Furthermore, the ability to produce compounds produced from a starting material of L-methionine, such as S-adenosylmethionine, can also be imparted or enhanced by enhancing activity of an enzyme of the biosynthesis system of the objective compound, or reducing the activity of an enzyme of a pathway branching away from the biosynthesis pathway of the objective compound or an enzyme that decomposes the objective compound. For example, the ability to produce S-adenosylmethionine can be imparted or enhanced by enhancing the methionine adenosyltransferase activity (European Patent Laid-open Nos. 0647712 and 1457569) or enhancing the secretion factor MdfA encoded by the mdfA gene (U.S. Pat. No. 7,410,789).

Methods for increasing enzymatic activities of SAT and so forth and reducing enzymatic activities of cysteine desulfhydrase and so forth are exemplified below.

<Method for Increasing Enzymatic Activity>

The expression "enzymatic activity is increased" can mean that the objective enzymatic activity is increased compared with that of a non-modified strain such as a wild-type strain or a parent strain. Although the degree of increase of the enzymatic activity is not particularly limited so long as the enzymatic activity is increased compared with a non-modified strain, the enzymatic activity is increased 1.5 times or more, 2 times or more, or even 3 times or more, compared with that of a non-modified strain. Furthermore, when "enzymatic activity is increased", this includes not only when the objective enzymatic activity is increased in a strain which has the native objective enzymatic activity, but also when the objective enzymatic activity is imparted to a strain which does not have the native objective enzymatic activity. Moreover, so long as the objective enzymatic activity is increased as a result, an enzyme that is originally present in a bacterium may be attenuated or deleted, and then an appropriate enzyme may be also introduced.

Modification for increasing enzymatic activity may be attained by, for example, enhancing expression of a gene coding for the objective enzyme. The expression "enhancing or enhancement of expression of a gene" can have the same meaning as "increase of expression of a gene".

Enhancement of expression of a gene can be attained by, for example, increasing the copy number of the gene.

The copy number of the objective gene can be increased by introducing the gene into a chromosome. A gene can be introduced into a chromosome by, for example, using homologous recombination. For example, a large number of copies of a gene can be introduced into a chromosome by homologous recombination for a target sequence that is present on the chromosome in a large copy number. Examples of such target sequences include, but are not limited to, repetitive DNA and inverted repeats which are present at the both ends of a transposon. The objective gene can be ligated to the side of a gene coding for the objective enzyme on a chromosome in tandem or can also be introduced into an unnecessary gene on a chromosome so that the objective gene overlaps with the unnecessary gene. Such gene introduction can be attained by using a temperature sensitive vector or by using an integration vector. Alternatively, as disclosed in U.S. Pat. No. 5,595,889, it is also possible to incorporate the objective gene into a transposon, and allow it to be transferred to a chromosomal DNA to introduce a large number of copies of the gene. As the transposon, for example, Mu, Tn10 and Tn5 can be used. Whether an objective gene has been introduced into a chromosome can be confirmed by Southern hybridization using a part of the objective gene as a probe.

Furthermore, the copy number of an objective gene can also be increased by introducing a vector containing the gene into the host bacterium. For example, the copy number of an objective gene can be increased by ligating a DNA fragment containing the objective gene with a vector that functions in the host bacterium to construct an expression vector of the objective gene, and transforming the host bacterium with the expression vector. As the vector, a vector autonomously replicable in the cell of the host bacterium can be used. The vector can be a multi-copy vector. Furthermore, the vector can have a marker such as an antibiotic resistance gene for selection of the transformants. Examples of vectors autonomously replicable in *Escherichia coli* cells include pUC19, pUC18, pHSG299, pHSG399, pHSG398, pACYC184, pBR322, pSTV29 (all of these are available from Takara Bio), pMW219 (NIPPON GENE), pTrc99A (Pharmacia), pPROK series vectors (Clontech), pKK233-2 (Clontech), pET series vectors (Novagen), pQE series vectors (QIAGEN), broad host spectrum vector RSF1010, and so forth.

Furthermore, expression of a gene can be enhanced by improving transcription efficiency of the gene. Transcription efficiency of a gene can be improved by, for example, substituting a stronger promoter for the native promoter of the gene on the chromosome. A "stronger promoter" can mean a promoter that improves the transcription of the gene compared to the wild-type promoter. As a stronger promoter, for example, known high expression promoters, such as T7 promoter, trp promoter, lac promoter, tac promoter, and PL promoter, can be used. Furthermore, as the stronger promoter, a highly-active promoter may be obtained by using various reporter genes. For example, the −35 and −10 regions in the promoter region can be made so they are more similar to the consensus sequence, and hence the activity of the promoter can be enhanced (International Patent Publication WO00/18935). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Furthermore, gene expression can also be enhanced by improving the translation efficiency of the gene. Translation efficiency of a gene can be improved by, for example, replacing the SD sequence (also referred to as the ribosome binding site (RBS)) on the chromosome with a stronger SD sequence. The "stronger SD sequence" can mean a SD sequence that provides improved translation of mRNA compared to the wild-type SD sequence. Examples of a stronger SD sequence include, for example, the RBS of the gene 10 derived from phage T7 (Olins P. O. et al, Gene, 1988, 73, 227-235). Furthermore, it is known that substitution, insertion, or deletion of several nucleotides in the spacer region between RBS and the start codon, especially in the sequence immediately upstream of the start codon (5'-UTR), can significantly affect the stability and translation efficiency of the mRNA, and hence the translation efficiency of a gene can also be improved by such a modification.

Regions affecting gene expression, such as the promoter, SD sequence, and spacer region between RBS and the start codon, are also generically called "expression control regions" or "expression control sequences". An expression control region can be determined by using a promoter-search vector or gene analysis software such as GENETYX. Such expression control regions can be modified by, for example, a method using a temperature sensitive vector or the Red driven integration method (WO2005/010175).

Further, expression of an objective gene can also be enhanced by amplifying a regulator that increases expression of the gene, or deleting or attenuating a regulator that reduces expression of the gene. Examples of such regulators include, for example, those belonging to the LysR family, and so forth, and they can be found by using a database, such as EcoCyc (ecocyc.org/), or the like. A regulator can be modified by monitoring the increase of the transcription amount of the objective gene, or the increase of the amount of the objective protein, as an index.

Such methods for enhancing gene expression as mentioned above may be used independently or in an arbitrary combination.

Furthermore, a modification that increases enzymatic activity can also be attained by, for example, enhancing specific activity of the objective enzyme. An enzyme having enhanced specific activity can be obtained by, for example, searching various bacteria. Furthermore, a highly-active enzyme may also be obtained by introducing a mutation into the enzyme. Enhancement of specific activity may be independently used, or may be used in an arbitrary combination with such methods for enhancing gene expression as mentioned above.

The method of the transformation is not particularly limited, and conventionally known methods can be used. For example, methods of treating recipient cells with calcium chloride so as to increase permeability thereof for DNA, which has been reported for *Escherichia coli* K-12 strain (Mandel, M. and Higa, A., J. Mol. Biol., 53:159-162 (1970)), and methods of preparing competent cells from cells which are at the growth phase, followed by transformation with DNA, which has been reported for *Bacillus subtilis* (Duncan, C. H., Wilson, G. A. and Young, F. E., Gene, 1, 153 (1977)) can be used. Alternatively, a method of making DNA-recipient cells into protoplasts or spheroplasts, which can easily take up recombinant DNA, followed by introducing a recombinant DNA into the cells, which is known to be applicable to *Bacillus subtilis*, actinomycetes and yeasts (Chang, S, and Choen, S. N., 1979, Molec. Gen. Genet., 168:111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)), can be used.

Increase of the objective enzymatic activity can be confirmed by measuring the enzymatic activity.

Increase of the transcription amount of an objective gene can be confirmed by comparing the amount of mRNA transcribed from the gene with that of a wild-type strain or a non-modified strain. Examples of methods for evaluating amount of mRNA include Northern hybridization, RT-PCR, and so forth (Molecular Cloning, Cold spring Harbor Laboratory Press, Cold Spring Harbor (USA), 2001).

Increase of the amount of the objective protein can be confirmed by Western blotting using an antibody (Molecular Cloning, Cold Spring Harbor Laboratory Press, Cold Spring Harbor (USA), 2001).

<Methods for Reducing Enzymatic Activity>

The expression "enzymatic activity is reduced" can mean that the enzymatic activity is decreased compared with that of a non-modified strain such as a wild-type strain or a parent strain, and includes when the activity has completely disappeared. Although the degree of the reduction of the enzymatic activity is not particularly limited so long as the activity is reduced compared with that of a non-modified strain, it can be reduced to, for example, 75% or less, 50% or less, 25% or less, or 10% or less compared with that of a non-modified strain, and the complete disappearance of the activity is an example. Depending on the type of enzyme, it may be better not to completely eliminate the enzymatic activity.

A modification for reducing the enzymatic activity can be attained by, for example, reducing expression of a gene coding for the objective enzyme. Expression of a gene can be reduced by, for example, modifying an expression control sequence, such as promoter and SD sequence, of the gene. When an expression control sequence is modified, one or more nucleotides, two or more nucleotides, or even three or more nucleotides, of the expression control sequence can be modified. Furthermore, a part or all of the expression control sequence can be deleted. Expression of a gene can also be reduced by expressing an antisense RNA.

A modification for reducing enzymatic activity can also be attained by, for example, deleting a part or all of a coding region of a gene coding for the objective enzyme on a chromosome. Furthermore, the whole gene, including the sequences upstream and downstream of the gene on the chromosome, may be deleted. The region to be deleted may be an N-terminus region, an internal region or a C-terminus region, so long as the enzymatic activity is reduced. Deletion of a longer region will usually more surely inactivate the gene. Furthermore, the reading frames upstream and downstream of the region to be deleted may not be the same.

A modification for reducing enzymatic activity can also be attained by introducing a mutation resulting in amino acid substitution (missense mutation), a stop codon (nonsense mutation), or a frame shift mutation which adds or deletes one or two nucleotides into a coding region of a gene coding for the objective enzyme on a chromosome (Journal of Biological Chemistry, 272:8611-8617 (1997); Proceedings of the National Academy of Sciences, USA, 95 5511-5515 (1998); Journal of Biological Chemistry, 266, 20833-20839 (1991)).

A modification for reducing the enzymatic activity can also be attained by inserting another sequence into a coding region of a gene coding for the objective enzyme on the chromosome. Such a sequence may be inserted into any region of the gene, and insertion of a longer sequence can more surely inactivate the objective gene. Reading frames upstream and downstream of the insertion site may not be the same. The other sequence is not particularly limited so long as a sequence which decreases or deletes function of the encoded protein is chosen, and examples include a marker gene such as antibiotic resistance genes, a gene useful for L-cysteine production, and so forth.

A gene on a chromosome can be modified as described above by, for example, preparing a deletion-type gene, in which a partial sequence of the gene is deleted so that the deletion-type gene does not produce a protein that can normally function, and then transforming a bacterium with a recombinant DNA containing the deletion-type gene to cause homologous recombination between the deletion-type gene and the native gene on the chromosome, which results in substitution of the deletion-type gene for the native gene on the chromosome. The above operation can be made easier by introducing a marker gene suitable for a characteristic of the host such as auxotrophy into the recombinant DNA. The protein encoded by the deletion-type gene has a conformation different from that of the wild-type protein, even if it is even produced, and thus the function is reduced or deleted. Such gene disruption based on gene substitution utilizing homologous recombination has already been established, and examples include the method called Red-driven integration (Datsenko, K. A., and Wanner, B. L., Proc. Natl. Acad. Sci. USA, 97:6640-6645 (2000)), methods using a linear DNA such as the method of utilizing Red driven integration in combination with an excision system derived from λ phage (Cho, E. H., Gumport, R. I., Gardner, J. F., J. Bacteriol., 184:5200-5203 (2002)) (refer to WO2005/010175), methods using a plasmid containing a temperature sensitive replication origin, methods using a plasmid capable of conjugative transfer, methods utilizing a suicide vector without a replication origin in a host (U.S. Pat. No. 6,303,383, Japanese Patent Laid-open (Kokai) No. 05-007491), and so forth.

A modification for reducing enzymatic activity can also be attained by, for example, mutagenesis. Examples of mutagenesis include exposure to UV irradiation or a treatment with a typical mutagen such as N-methyl-N'-nitro-N-nitrosoguanidine (MNNG), ethyl methanesulfonate (EMS) and methyl methanesulfonate (MMS).

Decrease of the enzymatic activity can be confirmed by measuring the enzymatic activity. The cysteine desulfhydrase activity can be measured by the method described in Japanese Patent Laid-open (Kokai) No. 2002-233384.

Decrease of the transcription amount of an objective gene can be confirmed by comparing the amount of the mRNA transcribed from the gene with that of a non-modified strain. Examples of methods for evaluating amount of mRNA include Northern hybridization, RT-PCR, and so forth (Molecular Cloning, Cold Spring Harbor Laboratory Press, Cold Spring Harbor, USA, 2001).

Decrease of the amount of an objective protein can be confirmed by Western blotting using an antibody (Molecular Cloning, Cold Spring Harbor Laboratory Press, Cold Spring Harbor, USA, 2001).

<Enhancement of Expression of Gene Involved in Sulfite Reduction>

The bacterium can be modified so that expression of one or more genes involved in sulfite reduction is increased. The bacterium can be obtained by modifying a bacterium belonging to the genus *Escherichia* and having L-cysteine-producing ability such as those mentioned above so that expression of a gene involved in sulfite reduction is increased. The bacterium can also be obtained by modifying a bacterium belonging to the genus *Escherichia* so that expression of a gene involved in sulfite reduction is increased, and then imparting or enhancing L-cysteine-producing ability.

Examples of the gene involved in sulfite reduction include a gene coding for a sulfite reductase. Sulfite reductase can refer to a protein having sulfite-reducing activity. The sulfite-reducing activity can mean an activity of catalyzing the reaction of reducing sulfite ion ($-SO_3^{2-}$) into sulfide ion ($-S^{2-}$). Examples of the gene coding for sulfite reductase include the cysJ gene and the cysI gene. The sulfite reductase of *Escherichia coli* is an NADPH-dependent sulfite reductase (EC 1.8.1.2), and it has an $\alpha_8\beta_4$ complex structure which includes a subunits encoded by the cysJ gene and β subunits encoded by the cysI gene. Therefore, when a protein shows the sulfite-reducing activity, this can mean not only that the protein encoded by the gene shows sulfite-reducing activity by itself, but also that a complex including the protein as a subunit shows the sulfite-reducing activity.

Furthermore, examples of the gene involved in sulfite reduction can include a gene involved in the biosynthesis of a cofactor of sulfite reductase. Examples of the cofactor of sulfite reductase include siroheme used as a prosthetic group, and NADPH and flavin used as a coenzyme. Among these, siroheme is a particular example. Examples of the gene involved in the biosynthesis of siroheme include the cysG gene coding for siroheme synthetase. The protein encoded by the cysG gene has an activity of catalyzing conversion of uroporphyrinogen III (Uro'gen III) as an intermediate into siroheme.

The proteins encoded by the cysJ gene, cysI gene and cysG gene are also referred to as the CysJ protein, CysI protein and CysG protein, respectively.

The cysJ gene of the *Escherichia coli* K12 MG1655 strain corresponds to the complementary sequence of the sequence at positions 2888121 to 2889920 in the genome sequence registered at the NCBI database as GenBank accession NC_000913 (VERSION NC_000913.2 GI: 49175990). The cysJ gene of the *Escherichia coli* K12 MG1655 strain is synonymous with ECK2759 and JW2734. The CysJ protein of the *Escherichia coli* K12 MG1655 strain is registered as GenBank accession NP_417244 (version NP_417244.1 GI: 16130671, locus_tag="b2764").

The cysI gene of the *Escherichia coli* K12 MG1655 strain corresponds to the complementary sequence of the sequence at positions 2886409 to 2888121 of the genome sequence. The cysI gene of the *Escherichia coli* K12 MG1655 strain is synonymous with ECK2758 and JW2733. The CysI protein of the *Escherichia coli* K12 MG1655 strain is registered as GenBank accession NP_417243 (version NP_417243.1 GI: 16130670, locus_tag="b2763").

Furthermore, the cysG gene of the *Escherichia coli* K12 MG1655 strain corresponds to the sequence at positions 3495850 to 3497223 of the genome sequence. The cysG gene of the *Escherichia coli* K12 MG1655 strain is synonymous with ECK3356 and JW3331. The CysG protein of the *Escherichia coli* K12 MG1655 strain is registered as GenBank accession NP_417827 (version NP_417827.1 GI: 16131246, locus_tag="b3368").

The nucleotide sequences of the cysJ gene, cysI gene, and cysG gene of the MG1655 strain are shown as SEQ ID NOS: 39, 43 and 47, respectively. The amino acid sequences of the proteins encoded by these genes are shown as SEQ ID NOS: 40, 44 and 48, respectively. The nucleotide sequences of the cysJ gene, cysI gene and cysG gene of the *Pantoea ananatis* SC17 strain are shown as SEQ ID NOS: 41, 45 and 49, respectively. The amino acid sequences of the proteins encoded by these genes are shown as SEQ ID NOS: 42, 46 and 50, respectively. The *Pantoea ananatis* SC17 strain was deposited on Feb. 4, 2009 at the National Institute of Advanced Industrial Science and Technology, International Patent Organism Depository (Address: Tsukuba Central 6, 1-1, Higashi 1-Chome, Tsukuba-shi, Ibaraki-ken, 305-8566, Japan), and assigned an accession number of FERM BP-11091.

Since the nucleotide sequence of the cysJ gene may differ depending on the genus, species or strain to which the bacterium belongs, the cysJ gene of which expression is increased may be a variant of the nucleotide sequence shown as SEQ ID NO: 39 or 41, so long as it codes for a protein having the sulfite-reducing activity. A variant of the cysJ gene can be searched for by using BLAST (blast.genome.jp/) or the like with referring to, for example, the nucleotide sequence of SEQ ID NO: 39 or 41. The variant of the cysJ gene can include homologues of the gene, such as genes that can be amplified by PCR using a chromosome of such a microorganism as bacteria belonging to the family Enterobacteriaceae and coryneform bacteria as a template and synthetic oligonucleotides prepared on the basis of the nucleotide sequence of SEQ ID NO: 39 or 41.

The cysJ gene may encode for a protein having the amino acid sequence of the CysJ protein as mentioned above, such as the amino acid sequence shown as SEQ ID NO: 40 or 42, but can also include substitution, deletion, insertion, addition or the like of one or several amino acid residues at one or several positions, so long as it codes for a protein having the sulfite-reducing activity. Although the number meant by the term "one or several" may differ depending on positions in the three-dimensional structure of the protein or types of amino acid residues, specifically, it can be 1 to 20, 1 to 10, or even 1 to 5. The above substitution, deletion, insertion, or addition of one or several amino acid residues can be a conservative mutation that maintains normal function of the protein. The conservative mutation is typically a conservative substitution. The conservative substitution is a mutation wherein substitution takes place mutually among Phe, Trp and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion etc. can be a result of a naturally-occurring mutation (mutant or variant) due to an individual difference, a difference of species, or the like of a bacterium from which the gene is derived.

Furthermore, the gene having such a conservative mutation as mentioned above may be a gene coding for a protein showing a homology of 80% or more, 90% or more, 95% or more, 97% or more, or even 99% or more, to the total amino acid sequence of the CysJ protein, such as the total sequence of the amino acid sequence of SEQ ID NO: 40 or 42, and having the sulfite-reducing activity. In this specification, "homology" may mean "identity".

The cysJ gene may be a DNA that is able to hybridize with a probe that can be prepared from a known gene sequence, for example, a sequence complementary to a part or all of the nucleotide sequence of SEQ ID NO: 39 or 41, under stringent conditions, and coding for a protein having the sulfite-reducing activity. The "stringent conditions" can refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or even not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe used for the aforementioned hybridization may be a sequence that is complementary to a part of the gene as described above. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of the hybridization may be, for example, 50° C., 2×SSC and 0.1% SDS.

Similarly, since the nucleotide sequence of the cysI gene may differ depending on the genus, species or strain to which the bacterium belongs, the cysI gene of which expression is increased may be a variant of the nucleotide sequence of SEQ ID NO: 43 or 45, so long as it codes for a protein having the sulfite-reducing activity. The above explanations for variants of the cysJ gene and CysJ protein are similarly applied to the above variant of the cysI gene.

Similarly, since the nucleotide sequence of the cysG gene may differ depending on the genus, species or strain to which the bacterium belongs, the cysG gene of which expression is increased may be a variant of the nucleotide sequence of SEQ ID NO: 47 or 49, so long as it codes for a protein having the activity of catalyzing conversion of uroporphyrinogen III (Uro'gen III) into siroheme. The above explanation for variants of the cysJ gene and CysJ protein is similarly applied to the above variant of the cysG gene.

The aforementioned explanation of the variants of genes and proteins are also similarly applied to arbitrary proteins including enzymes such as serine acetyltransferase and 3-phosphoglycerate dehydrogenase and transporters such as YdeD protein, and the genes coding for them.

The phrase "expression of a gene involved in sulfite reduction is increased" can mean that the expression amount of the gene involved in sulfite reduction is increased compared with that of a non-modified strain such as a wild-type strain or a parent strain. Although the degree of increase of expression amount of the gene involved in sulfite reduction is not particularly limited so long as it is increased compared with that of a non-modified strain, it can be increased 1.5 times or more, 2 times or more, 3 times or more, compared with that of a non-modified strain. The phrase "expression of a gene involved in sulfite reduction is increased" can include not only when expression of a gene involved in sulfite reduction is increased in a strain in which the gene involved in sulfite reduction is natively expressed, but also when a gene involved in sulfite reduction is expressed in a strain in which the gene involved in sulfite reduction has not been natively expressed. That is, for example, when a gene involved in sulfite reduction is introduced into a strain not having the gene involved in sulfite reduction, and the gene involved in sulfite reduction is expressed in the strain. Moreover, so long as expression of a gene involved in sulfite reduction is increased as a result, expression of a gene involved in sulfite reduction and natively possessed by a bacterium may be attenuated or deleted, and then an appropriate sulfite reductase may be introduced.

The bacterium can be modified so that expression of at least a gene coding for siroheme synthetase is increased. Furthermore, the bacterium can be modified so that expression of a gene coding for siroheme synthetase is increased, and expression of a gene coding for sulfite reductase is increased.

Modification for increasing expression of a gene involved in sulfite reduction can be attained by the methods for enhancing expression of a gene exemplified in the section of <Methods for increasing enzymatic activity> mentioned above.

In addition, as mentioned above, a modification for increasing expression of a gene may also be attained by amplifying a regulator that increases expression of the objective gene. Examples of a regulator that increases expression of a gene coding for a sulfite reductase include the protein (CysB) encoded by the cysB gene. It is known that CysB positively regulates expression of the cysJIH operon containing the cysJ gene and cysI gene coding for a sulfite reductase, and therefore expression of a gene involved in sulfite reduction can be enhanced by enhancing expression of the cysB gene.

Increase of the expression of a gene can be confirmed by, for example, confirming the increase of the transcription amount of the gene by Northern hybridization or RT-PCR as described above, or by confirming increase of the protein amount by Western blotting. Furthermore, increase of the expression of a gene involved in sulfite reduction can also be confirmed by measuring activity of the protein encoded by the gene involved in sulfite reduction. Activity of sulfite reductase can be measured by a known method (Covbs J. et al., J. Biol. Chem., 268, 18604-18609 (1993)). Activity of siroheme synthetase can also be measured by a known method (Spencer J. B. et al., FEBS Lett., 335(1):57-60, Nov. 29, 1993).

<2> Method for Producing L-Cysteine, Related Substance Thereof or Mixture Thereof By culturing the bacterium described herein, obtained as described above, in a medium containing thiosulfate and collecting L-cysteine, a related substance thereof or a mixture thereof from the medium, these compounds can be produced. Examples of the related substance of L-cysteine include L-cystine, S-sulfocysteine, thiazolidine derivatives, hemithioketals corresponding to the thiazolidine derivatives, L-methionine, S-adenosylmethionine, and so forth mentioned above.

The medium can be any ordinary media which includes a carbon source, nitrogen source, sulfur source, inorganic ions, and other organic components as required, and must include thiosulfate.

As the carbon source, saccharides such as glucose, fructose, sucrose, molasses and starch hydrolysate, and organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the sulfur source, thiosulfate alone may be included, or other sulfur compounds may be also be present in the medium in addition to thiosulfate. Examples of other sulfur compounds include inorganic sulfur compounds such as sulfates, sulfites, hyposulfites and sulfides. Although the weight ratio of thiosulfate and the other sulfur compound contained in the medium is not particularly limited, for example, the weight ratio of thiosulfate:other sulfur source is usually 5:95 to 100:0, 20:80 to 100:0, 50:50 to 100:0, or even 80:20 to 100:0.

The content of thiosulfate in the medium can be, for example, usually 0.1 g/L or higher, or 0.3 g/L or higher. Although the maximum content of thiosulfate is not particularly limited, it may be, for example, 100 g/L or lower, or 10 g/L or lower. Thiosulfate may be a free acid or thiosulfate salt, or may be an arbitrary mixture thereof. The type of thiosulfate salt is not particularly limited, and examples include sodium salt, calcium salt, ammonium salt, and so forth.

Thiosulfate may be present in the medium over the entire period of the culture, or only a part of the culture period. For example, if the method includes a proliferation stage of the L-cysteine-producing bacterium, and a L-cysteine producing stage, it is sufficient that thiosulfate is present during at least the production stage, and thiosulfate may be or may not be present in the medium during the proliferation stage. Furthermore, thiosulfate may be present in the medium over the entire period or only a part of the L-cysteine producing stage. For example, the thiosulfate amount does not need to be within the aforementioned range over the entire period of the production stage, that is, thiosulfate may be present in the medium within the aforementioned range during an early period of that stage, and the thiosulfate content may decrease with the lapse of the culture time. Furthermore, thiosulfate may be added continuously or intermittently. In addition, the contents of medium components other than thiosulfate may also vary during the culture period, and they may be added during the culture period.

As organic trace amount nutrients, required substances such as vitamin B$_1$, yeast extract and so forth can be added in appropriate amounts. Other than these, potassium phosphate, magnesium sulfate, iron ions, manganese ions and so forth can be added in small amounts, as required.

The culture can be performed under aerobic conditions for 30 to 90 hours. The culture temperature can be controlled to be at 25° C. to 37° C., and pH can be controlled to be 5 to 8 during the culture. To adjust the pH, inorganic or organic acidic or alkaline substances, ammonia gas and so forth can be used.

L-cysteine, a related substance thereof or a mixture thereof can be collected from the culture broth by a combination of ion-exchange resin method (Nagai, H. et al., Separation Science and Technology, 39(16), 3691-3710), membrane separation method (Japanese Patent Laid-open (Kokai) Nos. 9-164323 and 9-173792), crystallization method (WO2008/078448, WO2008/078646), and other conventionally known methods.

The collected L-cysteine, a related substance thereof or a mixture thereof can contain microbial cells, medium components, moisture, metabolic by-products of microbes, and so forth in addition to the objective compounds.

L-cysteine obtained as described above can be used for production of L-cysteine derivatives. The L-cysteine derivatives include methylcysteine, ethylcysteine, carbocisteine, sulfocysteine, acetylcysteine, and so forth.

Furthermore, when a thiazolidine derivative of L-cysteine is accumulated in the medium, L-cysteine can be produced by collecting the thiazolidine derivative from the medium and breaking the reaction equilibrium between the thiazolidine derivative and L-cysteine so that L-cysteine is excessively produced. When S-sulfocysteine is accumulated in the medium, it can be converted into L-cysteine by reduction using a reducing agent such as dithiothreitol.

Examples

Hereafter, the present invention will be explained more specifically with reference to the following non-limiting example. In the following example, cysteine means L-cysteine.

Example

Production of Cysteine by *E. Coli* Overexpressing cysG Gene or cysGJI Genes Using Thiosulfate as the Sulfur Source Construction of Expression Plasmids for Genes Involved in Sulfite Reduction As genes involved in sulfite reduction, the cysG gene of *P. ananatis* SC17 strain, the cysGJI genes of *P. ananatis* SC17 strain, the cysG gene of *E. coli* MG1655 strain, and the cysGJI genes of *E. coli* MG1655 strain were used. These genes were each cloned in an expression vector to construct expression plasmids of the genes. The procedure is described in (1-1) to (1-7).

Construction of Expression Vectors

As the expression vector, pMIV-Pnlp23-ter constructed from pMIV-5JS (Japanese Patent Laid-open (Kokai) No. 2008-99668) was used. This vector has the nlp23 promoter (Pnlp23), which is a strong promoter, and the rrnB terminator, and has SalI and XbaI sites between Pnlp23 and the rrnB terminator. By amplifying an objective gene using primers in which SalI (or XhoI) and XbaI sites are designed, and inserting the amplified gene into the vector at a position between Pnlp23 and the rrnB terminator, an expression plasmid of the objective gene can be constructed. "Pnlp23" is a mutant promoter constructed from "Pnlp0", which is a promoter of the wild-type nlpD gene derived from the *E. coli* K12 strain, in order to control expression intensity.

As the expression vector, pMIV-Pnlp8-YeaS7 constructed from pMIV-5JS (Japanese Patent Laid-open (Kokai) No. 2008-99668) was also used. This vector has the nlp8 promoter (Pnlp8), which is a strong promoter, and the rrnB terminator, and further has the yeaS gene of the *E. coli* K12 strain cloned at a position between Pnlp8 and the rrnB terminator using SalI and XbaI sites. By amplifying an objective gene using primers in which SalI (or XhoI) and XbaI sites are designed, and inserting the amplified gene into the vector, an expression plasmid in which the yeaS gene fragment of the vector is replaced with the objective gene fragment can be constructed. "Pnlp8" is a mutant promoter constructed from "Pnlp0", which is a promoter of the wild-type nlpD gene of the *E. coli* K12 strain, in order to control expression intensity.

The details of the construction of these expression vectors are described below.

First, by PCR using the chromosomal DNA of the *E. coli* MG1655 strain as the template as well as a primer P1 (agct-gagtcgacccccagga aaaattggttaataac, SEQ ID NO: 13) and a primer P2 (agctgagcatgcttccaactgcgctaatgacgc, SEQ ID NO: 14) as primers, a DNA fragment containing a promoter region of the nlpD gene (henceforth wild-type nlpD gene promoter is referred to as "Pnlp0") of about 300 bp was obtained. At the 5' ends of the aforementioned primers, sites for the restriction enzymes SalI and PaeI were designed, respectively. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and a final cycle of 72° C. for 5 minutes. The resulting fragment was treated with SalI and PaeI, and inserted into pMIV-5JS (Japanese Patent Laid-open (Kokai) No. 2008-99668) at the SalI-PaeI site to obtain the plasmid pMIV-Pnlp0. The nucleotide sequence of the PaeI-SalI fragment containing the Pnlp0 promoter inserted into this pMIV-Pnlp0 plasmid was as shown in SEQ ID NO: 1.

Then, by PCR using the chromosomal DNA of the MG1655 strain as the template, as well as primer P3 (agct-gatcta gaaaacagaa tttgcctggc ggc, SEQ ID NO: 15) and primer P4 (agctgaggat ccaggaagag tttgtagaaa cgc, SEQ ID NO: 16) as primers, a DNA fragment containing a terminator region of the rrnB gene of about 300 bp was obtained. At the 5' ends of the aforementioned primers, sites for the restriction enzymes XbaI and BamHI were designed, respectively. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 59° C. for 20 seconds, and 72° C. for 15 seconds, and a final cycle of 72° C. for 5 minutes. The obtained fragment was treated with XbaI and BamHI, and inserted into pMIV-Pnlp0 at the XbaI-BamHI site to obtain the plasmid pMIV-Pnlp0-ter.

Then, by PCR using the chromosomal DNA of the MG1655 strain as the template, as well as primer P5 (agct-gagtcg acgtgttcgc tgaatacggg gt, SEQ ID NO: 17) and primer P6 (agctgatcta gagaaagcat caggattgca gc, SEQ ID NO: 18) as primers, a DNA fragment of about 700 bp containing the yeaS gene was obtained. At the 5' ends of the aforementioned primers, sites for the restriction enzymes SalI and XbaI were designed, respectively. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and a final cycle of 72° C. for 5 minutes. The resulting fragment was treated with SalI and XbaI, and inserted into pMIV-Pnlp0-ter at the SalI-XbaI site to obtain the plasmid pMIV-Pnlp0-YeaS3. As described above, a yeaS expression unit including the nlpD promoter, the yeaS gene, and the rrnB terminator ligated in this order was constructed on the pMIV-5JS vector.

In order to modify the −10 region of the nlpD promoter to make it a stronger promoter, the −10 region was randomized by the following method. The nlpD promoter region contains two of regions presumed to function as promoters (FIG. 2), and they are indicated as pnlp1 and pnlp2, respectively, in the drawing. By PCR using the plasmid pMIV-Pnlp0 as the template as well as the primers P1 and P7 (atcgtgaaga tcttttccag tgttnannag ggtgccttgc acggtnatna ngtcactgg ("n" means that the corresponding residue can be any of a, t, g and c), SEQ ID NO: 19) as primers, a DNA fragment in which the −10 region located at the 3' end side of the nlpD promoter (−10(Pnlp1), FIG. 2) was randomized was obtained. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and a final cycle of 72° C. for 5 minutes.

Similarly, by PCR using the plasmid pMIV-Pnlp0 as the template as well as the primers P2 and P8 (tggaaaagat cttcannnnn cgctgacctg cg ("n" means that the corresponding residue can be any of a, t, g and c), SEQ ID NO: 20) as primers, a DNA fragment in which the −10 region located at the 5' end side of the nlpD promoter (−10(Pnlp2), FIG. 2) was randomized was obtained. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and a final cycle of 72° C. for 5 minutes.

The obtained 3' and 5' end side fragments were ligated by using the BglII sites designed in the primers P7 and P8 to construct a fragment containing the full length of the nlpD promoter in which two −10 regions were randomized. By PCR using this fragment as the template as well as the primers P1 and P2 as primers, a DNA fragment containing the full length of a mutant type nlpD promoter was obtained. The PCR cycle was as follows: 95° C. for 3 minutes, followed by 2 cycles of 95° C. for 60 seconds, 50° C. for 30 seconds, and 72° C. for 40 seconds, 12 cycles of 94° C. for 20 seconds, 60° C. for 20 seconds, and 72° C. for 15 seconds, and a final cycle of 72° C. for 5 minutes.

The obtained DNA fragment containing the mutant Pnlp was treated with the restriction enzymes SalI and PaeI, for which sites were designed in the 5' ends of the primers, and inserted into the plasmid pMIV-Pnlp0-YeaS3 similarly treated with SalI and PaeI to substitute the mutant Pnlp for the wild-type nlpD promoter region (Pnlp0) on the plasmid. From the resultants, one having the promoter sequence (Pnlp8) shown in FIG. 2 was selected, and designated pMIV-Pnlp8-YeaS7. The nucleotide sequence of the PaeI-SalI fragment of the Pnlp8 promoter inserted into this plasmid was as shown in SEQ ID NO: 21.

In the same manner, a DNA fragment containing the mutant Pnlp was inserted into the plasmid pMIV-Pnlp0-ter treated with SalI and PaeI to substitute the mutant Pnlp for the nlpD promoter region (region of Pnlp0) on the plasmid. One of the resultants was designated pMIV-Pnlp23-ter. The nucleotide sequence of the PaeI-SalI fragment of the Pnlp23 promoter inserted into this plasmid was as shown in SEQ ID NO: 2.

(1-2) Construction of Overexpression Plasmid for cysG Gene of E. Coli MG1655 Strain By PCR using the chromosomal DNA of the E. coli MG1655 strain (ATCC No. 47076) as the template, as well as primer SalI-cysG (Ec) Fw (ACGCGTCGACATGGAT-CATTTGCCTATATT, SEQ ID NO: 8) and primer XbaI-cysG (Ec) Rv (GCTCTAGATTAATGGTTGGAGAACCAGTTC, SEQ ID NO: 9) as primers, the cysG gene fragment was amplified. At the 5' ends of these primers, sites for the restriction enzymes SalI and XbaI were designed. PCR was performed by using PrimeSTAR Polymerase (TaKaRa) and a standard reaction mixture composition described in the attached protocol with a PCR cycle of 94° C. for 5 minutes, followed by 30 cycles of 98° C. for 5 seconds, 55° C. for 10 seconds, and 72° C. for 2 minutes, and keeping at 4° C. as the final cycle. The obtained fragment was treated with SalI and XbaI, and inserted into pMIV-Pnlp23-ter treated with the same restriction enzymes to obtain the plasmid pMIV-Pnlp23-cysG (Ec) in which the cysG gene of the E. coli MG1655 strain was cloned.

(1-3) Cloning of cysJI Genes of E. Coli MG1655 Strain

By PCR using the chromosomal DNA of the E. coli MG1655 strain as the template as well as primer SalI-cysJ (Ec) Fw (ACGCGTCGACATGACGACACAGGTC-CCACC, SEQ ID NO: 10) and primer XbaI-cysI (Ec) Rv (GCTCTAGATTAATCCCACAAATCACGCGCC, SEQ ID NO: 11), the cysJI gene fragment was amplified. At the 5' ends of these primers, sites for the restriction enzymes SalI and XbaI were designed. PCR was performed by using PrimeSTAR Polymerase (TaKaRa) and a standard reaction mixture composition described in the attached protocol with a PCR cycle consisting of 94° C. for 5 minutes, followed by 30 cycles of 98° C. for 5 seconds, 55° C. for 10 seconds, and 72° C. for 2 minutes, and keeping at 4° C. as the final cycle. The obtained fragment was treated with SalI and XbaI, and inserted into pMIV-Pnlp23-ter treated with the same restriction enzymes to obtain the plasmid pMIV-Pnlp23-cysJI (Ec) in which the cysJI genes of the E. coli MG1655 strain were cloned.

(1-4) Construction of Coexpression Plasmid for cysG Gene and cysJI Genes of E. coli MG1655 Strain PCR was performed by using the chromosomal DNA of the E. coli MG1655 strain as the template as well as the primer SalI-cysG (Ec) Fw (SEQ ID NO: 8) and primer cysG-JI (Ec) Rv (CAACGCGGAAGGTGGGACCTGTGTCGT-CATGCGTCGTTATGTTCCAGTTTAATGGTT GGAGAACCAGTTCAGTTTATC, SEQ ID NO: 12) as primers. PCR was performed by using PrimeSTAR Polymerase (TaKaRa) and a standard reaction mixture composition described in the attached protocol with a PCR cycle consisting of 94° C. for 5 minutes, follow by 30 cycles of 98° C. for 5 seconds, 55° C. for 10 seconds, and 72° C. for 2 minutes, and keeping at 4° C. as the final cycle. By this PCR, a gene fragment which includes the cysG gene and a sequence of 18 bp containing the start codon of the cysJ gene added downstream of the cysG gene was obtained. The salts, polymerase, and primers were removed from the reaction mixture containing the obtained fragment, and the resultant was used as a primer of the following PCR.

PCR was performed by using the plasmid DNA of pMIV-Pnlp23-cysJI (Ec) constructed in (1-3) as a template, as well as the aforementioned gene fragment and the primer XbaI-cysI (Ec) Rv (SEQ ID NO: 11) as primers. PCR was performed by using PrimeSTAR GXL Polymerase (TaKaRa) and a standard reaction mixture composition described in the attached protocol with a PCR cycle consisting of 98° C. for 10 seconds, followed by 30 cycles of 98° C. for 10 seconds, 58°

C. for 15 seconds, and 68° C. for 2 minutes, and keeping at 4° C. as the final cycle. By this PCR, a gene fragment which includes the cysG gene sequence and the cysJI gene sequence ligated downstream of the cysG gene sequence was obtained. At the 5' ends of the primers, SalI and XbaI sites were designed, respectively. The obtained fragment was treated with SalI and XbaI, and inserted into pMIV-Pnlp23-ter treated with the same restriction enzymes to obtain the plasmid pMIV-Pnlp23-cysGJI (Ec) in which the cysGJI genes of the E. coli MG1655 strain were cloned.

(1-5) Construction of Overexpression Plasmid for cysG Gene of P. ananatis SC17 Strain By PCR using the chromosomal DNA of the P. ananatis SC17 strain (FERM BP-11091) as the template, as well as primer CysG Fw (XhoI) (ACGCCTCGAGATGGAT-TATTTGCCTCTTTT, SEQ ID NO: 3) and primer CysG Rv (XbaI) (GCTCTAGATCAAGCCAGATTGACAACGG, SEQ ID NO: 4) as primers, the cysG gene fragment was amplified. PCR was performed by using PrimeSTAR Polymerase (TaKaRa) and a standard reaction mixture composition described in the attached protocol with a PCR cycle of 94° C. for 5 minutes, follow by 30 cycles of 98° C. for 5 seconds, 55° C. for 10 seconds, and 72° C. for 2 minutes, and keeping at 4° C. as the final cycle. Although the start codon of the cysG gene on the chromosomal DNA of P. ananatis was GTG, the start codon of the cysG gene present in the DNA fragment obtained by PCR was modified to ATG by changing GTG in the sequence of the start codon attaching site of the primer to ATG. Further, at the 5' ends of the aforementioned primers, XhoI and XbaI sites were designed, respectively. Because a restriction enzyme site for SalI existed in the ORF of the cysG gene of P. ananatis, XhoI was used as a substitute for SalI. The obtained fragment was treated with XhoI and XbaI, and inserted into pMIV-Pnlp8-YeaS7 treated with SalI and XbaI to obtain the plasmid pMIV-Pnlp8-cysG (Pa) in which the cysG gene of the P. ananatis SC17 strain was cloned. pMIV-Pnlp8-cysG (Pa) has a structure that the yeaS gene fragment on pMIV-Pnlp8-YeaS7 was replaced with the cysG gene fragment of the P. ananatis SC17 strain.

(1-6) Cloning of cysJI Genes of P. ananatis SC17 Strain

By PCR using the chromosomal DNA of the P. ananatis SC17 strain as the template, as well as primer CysJ Fw (SalI) (ACGCGTCGACATGACGACTCAGGCACCAGG, SEQ ID NO: 5) and primer CysI Rv (XbaI) (GCTCTAGAT-CATTTTGCCTCCTGCCAGA, SEQ ID NO: 6) as primers, the cysJI gene fragment was amplified. At the 5' ends of the aforementioned primers, sites for the restriction enzymes SalI and XbaI were designed, respectively. PCR was performed by using PrimeSTAR Polymerase (TaKaRa) and a standard reaction mixture composition described in the attached protocol with a PCR cycle consisting of 94° C. for 5 minutes, followed by 30 cycles of 98° C. for 5 seconds, 55° C. for 10 seconds, and 72° C. for 2 minutes, and keeping at 4° C. as the final cycle. The obtained fragment was treated with SalI and XbaI, and inserted into pMIV-Pnlp23-ter treated with the same restriction enzymes to obtain the plasmid pMIV-Pnlp23-cysJI (Pa) in which the cysJI genes of the P. ananatis SC17 strain were cloned.

(1-7) Construction of Coexpression Plasmid for cysG Gene and cysJI Genes of P. ananatis SC17 Strain PCR was performed by using the chromosomal DNA of the P. ananatis SC17 strain as the template as well as the primer CysG Fw (XhoI) (SEQ ID NO: 3) and primer CysG-JI Rv (CTGGTGCCTGAGTCGTCATCGTTTTTC-CTCTCAAGCCAGATTGACAACGGCGGACTC GCG, SEQ ID NO: 7) as primers. PCR was performed by using PrimeSTAR Polymerase (TaKaRa) and a standard reaction mixture composition described in the attached protocol with a PCR cycle of 94° C. for 5 minutes, followed by 30 cycles of 98° C. for 5 seconds, 55° C. for 10 seconds, and 72° C. for 2 minutes, and keeping at 4° C. as the final cycle. By this PCR, a gene fragment which includes the cysG gene and a sequence of 11 bp containing the start codon of the cysJ gene added downstream of the cysG gene was obtained. The salts, polymerase, and primers were removed from the reaction mixture containing the obtained fragment, and the resultant was used as a primer for the following PCR.

PCR was performed by using the plasmid DNA of pMIV-Pnlp23-cysJI (Pa) constructed in (1-6) as the template, as well as the aforementioned gene fragment and the primer CysI Rv (XbaI) (SEQ ID NO: 6) as primers. PCR was performed by using PrimeSTAR GXL Polymerase (TaKaRa) and a standard reaction mixture composition described in the attached protocol with a PCR cycle of 98° C. for 10 seconds, followed by 30 cycles of 98° C. for 10 seconds, 58° C. for 15 seconds, and 68° C. for 2 minutes, and keeping at 4° C. as the final cycle. By this PCR, a gene fragment which includes the cysG gene sequence and the cysJI gene sequence ligated downstream of the cysG gene sequence was obtained. Although the start codon of the cysG gene on the chromosomal DNA of P. ananatis was GTG, the start codon of the cysG gene contained in the DNA fragment obtained by PCR was modified to ATG by changing GTG in the sequence of the start codon attaching site of the primer to ATG. Furthermore, at the 5' ends of the primers, XhoI and XbaI sites were designed, respectively. Since a restriction enzyme site for SalI existed in the ORF of the cysG gene of P. ananatis, XhoI was used as a substitute for SalI. The obtained fragment was treated with XhoI and XbaI, and inserted into pMIV-Pnlp23-ter treated with SalI and XbaI to obtain the plasmid pMIV-Pnlp23-cysGJI (Pa) in which the cysGJI genes of the P. ananatis SC17 strain were cloned.

(2) Construction of Cysteine-Producing E. Coli Bacterium

As a cysteine-producing E. coli bacterium, the MG1655int-4M/pACYC-DES strain was constructed which harbors the plasmid pACYC-DES having the ydeD gene, cysEX gene and serA5 gene, in which strain the cysM gene was introduced into the chromosome. The construction procedure will be described in (2-1) and (2-2).

(2-1) Construction of Plasmid pACYC-DES Having ydeD Gene, cysEX Gene and serA5 Gene The ydeD gene, cysEX gene and serA5 gene were cloned into the plasmid pACYC184 to construct the plasmid pACYC-DES. The ydeD gene encodes a transmembrane protein involved in secretion of metabolic products of the cysteine pathway, and it has been reported that it is useful for the cysteine production (U.S. Pat. No. 5,972,663). The cysEX gene is a mutant gene of cysE and codes for a mutant serine acetyltransferase (SAT) desensitized to feedback inhibition by cysteine (U.S. Pat. No. 6,218,168). The serA5 gene is a mutant gene of serA and codes for a mutant 3-phosphoglycerate dehydrogenase (PGD) deficient in the tyrosine residue at the C-terminus of the wild-type 3-phosphoglycerate dehydrogenase of Escherichia coli and desensitized to feedback inhibition by L-serine (U.S. Pat. No. 6,180,373). The construction procedure is shown below.

By PCR using the chromosomal DNA of the E. coli MG1655 strain as the template, as well as primer ydeD299F (agctgagtcg acatgtcgcg aaaagatggg gtg, SEQ ID NO: 22) and primer ydeD299R (agctgatcta gagtttgttc tggccccgac atc, SEQ ID NO: 23) as primers, the ydeD gene fragment of the Escherichia coli MG1655 strain was amplified.

Figure 3:
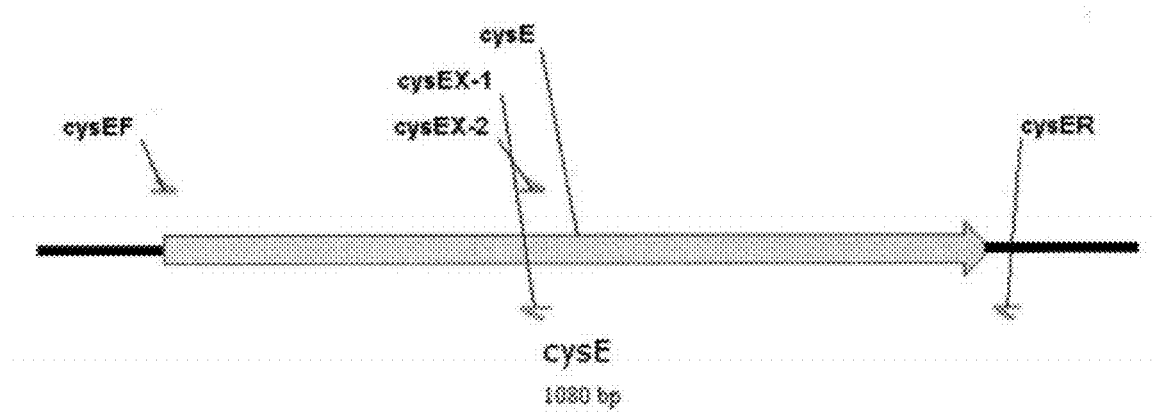
FIG. 3 shows the disposition of primers in the production of a cysEX gene fragment.

Furthermore, as shown in FIG. 3, the cysEX gene fragment was prepared. Specifically, first, by PCR using the chromosomal DNA of the *E. coli* MG1655 strain as the template, as well as primer cysEF (agctgagtcg acatgtcgtg tgaagaactg gaa, SEQ ID NO: 24) and primer cysEX-1 (atcaccgccg cttcaccaac g, SEQ ID NO: 25) as primers, an upstream side fragment of the cysEX gene was amplified. Then, by PCR using the chromosomal DNA of the *E. coli* MG1655 strain as the template, as well as primer cysEX-2 (cgttggtgaa gcggcggtga t, SEQ ID NO: 26) and primer cysER (agctgatcta gaatagatga ttacatcgca tcc, SEQ ID NO: 27) as primers, a downstream side fragment of the cysEX gene was amplified. These two PCR products were separated by electrophoresis and eluted from the gel. Subsequently, by performing PCR again using these two PCR products, these two PCR products were annealed at the overlapping portions to generate a DNA fragment containing the full length of the cysEX gene.

Furthermore, by PCR using the chromosomal DNA of the *E. coli* MG1655 strain as the template, as well as primer serA5F (agctgagtcg acatggcaaa ggtatcgctg gag, SEQ ID NO: 28) and primer serA5R (agctgatcta gattacagca gacgggcgcg aatgg, SEQ ID NO: 29) as primers, a serA5 gene fragment was amplified.

Furthermore, by PCR using the chromosomal DNA of the *E. coli* MG1655 strain as the template, as well as primer PrOMPAF (agctgagtcg accgcctcgt tatcatccaa aatc, SEQ ID NO: 30) and primer PrOMPAR (agctgagcat gcactaattt tcct-tgcgga ggc, SEQ ID NO: 31) as primers, a promoter PompA fragment was amplified.

At the 5' ends of the primer PrOMPAF, the primers ydeD299F, cysEF and serA5F for gene fragment amplification, SalI sites were designed. The amplified PompA fragment and each amplified gene fragment were treated with SalI and ligated to obtain three kinds of DNA fragments which include PompA and each gene ligated downstream of PompA.

Figure 4:
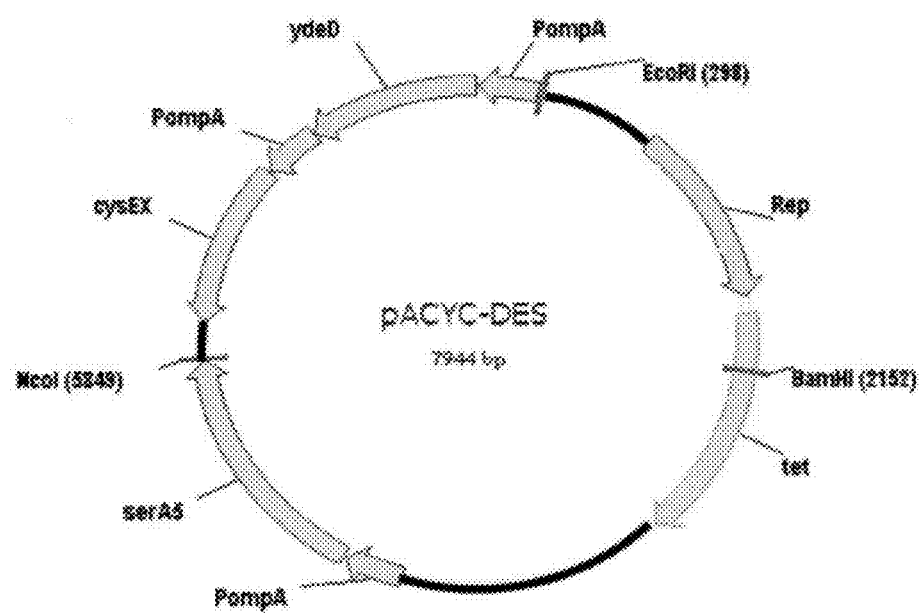
FIG. 4 shows the structure of the plasmid pACYC-DES.

Furthermore, at the 5' end of the primer PrOMPAR, a PaeI site was designed. At the 5' ends of the primers ydeD299R, cysER and serA5R for gene fragment amplification, restriction enzyme sites for incorporation into a vector were designed. By using these restriction enzyme sites, the three kinds of DNA fragments which include PompA and each gene ligated downstream of PompA were introduced into the plasmid pACYC184. A plasmid obtained as described above was designated pACYC-DES. The structure of pACYC-DES is shown in FIG. 4.

(2-2) Introduction of O-Acetyl-L-Serine Sulfhydrylase B Gene (cysM) into *E. coli* MG1655 Strain The O-acetyl-L-serine sulfhydrylase B gene (cysM) was introduced into the chromosome of the *E. coli* MG1655 strain to construct the MG1655int-4M strain. Furthermore, the plasmid pACYC-DES was introduced into the MG1655int-4M strain to construct an MG1655int-4M/pACYC-DES strain. For expression of the cysM gene introduced into the *E. coli* MG1655 strain, the promoter of the wild-type nlpD gene of the *P. ananatis* SC17 strain, "Pnlp4", was used. The construction procedure is explained below.

First, in order to express the cysM gene by using a promoter of an appropriate strength, a novel promoter Pnlp4 was obtained by the following procedure.

First, a DNA fragment containing about 180 bp of the promoter region of the nlpD gene was obtained by PCR using the genome of the *P. ananatis* SC17 strain as the template. The promoter of the wild-type nlpD gene of the *P. ananatis* SC17 strain amplified as described above is referred to as "Pnlp4". The primers used were primer P9 (agctgaaagc ttgcatgcac gcgtggcgat ctggcctgac tgc, SEQ ID NO: 32) and primer P10 (agctgagtcg accccgtggt ggcaaccttt aaaaaactg, SEQ ID NO: 33), and at the 5' ends of these primers, sites for the restriction enzymes SalI and PaeI were designed, respectively. The PCR cycle was as follows: 95° C. for 5 minutes, follow by 27 cycles of 94° C. for 20 seconds, 59° C. for 20 seconds, and 72° C. for 20 seconds, and a final cycle of 72° C. for 5 minutes. The obtained DNA fragment was treated with SalI and PaeI, and inserted into pMIV-Pnlp0-ter similarly treated with SalI and PaeI to obtain the plasmid pMIV-Pnlp-4-ter, which corresponded to pMIV-Pnlp0-ter in which Pnlp0 was replaced with Pnlp4. The nucleotide sequence of the PaeI-SalI fragment of Pnlp4 inserted into pMIV-Pnlp-4-ter is as shown in SEQ ID NO: 34.

The cysM gene cloned from the *E. coli* MG1655 strain was incorporated into the plasmid pMIV-Pnlp-4-ter obtained in (2-2). Specifically, by PCR using the genome of the *E. coli* MG1655 strain as the template, as well as primer P11 (agctgagtcg acgtgagtacattagaacaa acaat, SEQ ID NO: 37) and primer P12 (agctgatcta gaagtctccg atgctattaa tcc, SEQ ID NO: 38) as primers (98° C. for 5 minutes, followed by 30 cycles of 98° C. for 5 seconds, 50° C. for 10 seconds, and 72° C. for 60 seconds, and a final cycle of 72° C. for 2 minutes), the cysM gene fragment was amplified. The DNA fragment obtained as described above was treated with SalI and XbaI, and inserted into pMIV-Pnlp-4-ter treated with the same enzymes to prepare the plasmid pMIV-Pnlp-4-CysM, in which the cysM gene of the *E. coli* MG1655 strain was cloned. The nucleotide sequence of the cysM gene of the *E. coli* MG1655 strain is shown as SEQ ID NO: 35, and the amino acid sequence encoded by this gene is shown as SEQ ID NO: 36.

pMIV-Pnlp-4-CysM has the attachment sites for Mu phage originated from pMIV-5JS. Therefore, by allowing pMIV-Pnlp-4-CysM to coexist with the helper plasmid pMH10 having the Mu transposase gene (Zimenkov D. et al., Biotechnologiya (in Russian), 6, 1-22 (2004)) in a host cell, the cassette of Pnlp-4-CysM-rrnB terminator containing the chloramphenicol resistance gene existing on pMIV-Pnlp-4-CysM between the attachment sites of Mu phage can be inserted into the chromosome of the host. Furthermore, the chloramphenicol resistance gene carried by the pMIV-Pnlp-4-CysM plasmid exists between two attachment sites of λ phage (λattR and λattL), and can be excised and removed by the method described later.

First, the helper plasmid pMH10 was introduced into the MG1655 strain by electroporation, and the strain was cultured overnight at 30° C. on the LB agar medium containing 20 mg/L of kanamycin to select a strain into which pMH10 was introduced. The obtained transformant was cultured at 30° C., and pMIV-Pnlp-4-CysM was further introduced into this strain by electroporation. This strain, which was transformed with both pMH10 and pMIV-Pnlp-4-CysM, was subjected to a heat shock at 42° C. for 20 minutes, and then cultured at 39° C. on LB agar medium containing 20 mg/L of chloramphenicol to select colonies of chloramphenicol resistant strains. About 50 clones of the chloramphenicol resistant strains obtained as described above were each cultured at 39° C. for 48 hours on LB agar medium to eliminate pMH10 and pMIV-Pnlp-4-CysM. Then, a strain was obtained showing chloramphenicol resistance as a result of the insertion of the cassette containing the chloramphenicol resistance gene into the chromosome and showing kanamycin and ampicillin sensitivities as a result of the elimination of the both plasmids. Furthermore, it was confirmed that the objective cassette was inserted into the chromosome of the obtained strain by PCR using the chromosomal DNA of this strain as the template as well as the primers P1 and P6. The strain prepared as described above was designated MG1655int-4M (CmR).

The chloramphenicol resistance gene introduced into the MG1655int-4M (CmR) strain was removed with an excision system derived from λ phage. Specifically, the MG1655int-4M (CmR) strain was transformed with pMT-Int-Xis2 (WO2005/010175) carrying the Int-Xis gene of λ phage, and the MG1655int-4M strain showing chloramphenicol sensitivity was obtained from the obtained transformants.

Then, the plasmid pACYC-DES was introduced into MG1655int-4M to obtain the MG1655int-4M/pACYC-DES strain.

(3) Cysteine Production by E. Coli Overexpressing cysG Gene or cysGJI Genes using Thiosulfate as a Sulfur Source Strains of the above-obtained E. coli cysteine-producing bacterium, MG1655int-4M/pACYC-DES, were constructed, and into which the cysG overexpression plasimids pMIV-Pnlp23-cysG (Ec) and pMIV-Pnlp8-cysG (Pa), the cysG and cysJI coexpression plasmids pMIV-Pnlp23-cysGJI (Ec) and pMIV-Pnlp23-cysGJI (Pa), and pMIV-5JS as a control were each introduced. Cysteine production culture was performed with these strains, and cysteine production amounts were compared. For the cysteine production culture, a cysteine production medium having the following composition containing glucose as a carbon source and thiosulfate as a sulfur source was used.

Cysteine Production Medium: (Concentrations of the Components are Final Concentrations)

Components 1:

| | |
|---|---|
| $NH_4Cl$ | 12.1 g/L |
| $KH_2PO_4$ | 1.5 g/L |
| $MgSO_4 \cdot 7H_2O$ | 1 g/L |
| Thiamine hydrochloride | 0.1 mg/L |

Components 2:

| | |
|---|---|
| $FeSO_4 \cdot 7H_2O$ | 1.7 mg/L |
| $Na_2MoO_4 \cdot 2H_2O$ | 0.15 mg/L |
| $CoCl_2 \cdot 6H_2O$ | 0.7 mg/L |
| $MnCl \cdot 4H_2O$ | 1.6 mg/L |
| $ZnSO_4 \cdot 7H_2O$ | 0.3 mg/L |
| $CuSO_4 \cdot 5H_2O$ | 0.25 mg/L |

Components 3:

| | |
|---|---|
| Tryptone | 0.6 g/L |
| Yeast extract | 0.3 g/L |
| NaCl | 0.6 g/L |

Component 4:

| | |
|---|---|
| Calcium carbonate | 20 g/L |

Component 5:

| | |
|---|---|
| L-Histidine hydrochloride monohydrate | 135 mg/L |

Component 6:

| | |
|---|---|
| Sodium thiosulfate | 0.6 g/L |

Component 7:

| | |
|---|---|
| Pyridoxine hydrochloride | 2 mg/L |

Component 8:

| | |
|---|---|
| Glucose | 20 g/L |

For these components, stock solutions were prepared of 10-fold concentration (Components 1), 1000-fold concentration (Components 2), 100/6-fold concentration (Components 3), 100-fold concentration (Component 5), 1750/3-fold concentration (Component 6), 1000-fold concentration (Component 7), and 20-fold concentration (Component 8), they were mixed at the time of use, and the defined volume was obtained with sterilized water to attain the final concentrations. Sterilization was performed by autoclaving at 110° C. for 30 minutes (Components 1, 2, 3, 5 and 8), dry heat sterilization at 180° C. for 5 hours or longer (Component 4), or filter sterilization (Components 6 and 7). The L-cysteine production culture was performed as follows. Each L-cysteine-producing strain was spread on LB agar medium to perform pre-culture overnight at 34° C., and then cells corresponding to about 7 cm on the plate were scraped with an inoculation loop of 10-0 size (NUNC Blue Loop), and inoculated into 2 ml of the L-cysteine production medium contained in a large test tube (internal diameter: 23 mm, length: 20 cm) so as to make cell amounts at the time of the start of the culture substantially the same. Culture was performed at 37° C. with shaking, and terminated when glucose contained in the medium was completely consumed (21 to 24 hours). L-Cysteine produced in the medium was quantified by the method described by Gaitonde, M. K. (Biochem. J., 104(2):627-33, August 1967). In order to allow the strains to harbor the plasmids, chloramphenicol (25 mg/L) was added over the entire culture period. The experiment was performed in quadruplicate for each strain, and averages and standard deviations for the concentrations (g/L) of the accumulated cysteine are shown in Table 1.

It was revealed that, by enhancing expression of the cysG gene coding for the synthetase for siroheme, which is a cofactor of sulfite reductase, and further, by enhancing expression of the cysJI genes coding for the subunits of sulfite reductase in addition to the cysG gene, production of cysteine by fermentation in E. coli using thiosulfate as a sulfur source could be improved.

TABLE 1

Table 1: Effect of enhancement of expression of genes involved in sulfite reduction in E. coli cysteine-producing bacterium, MG1655int-4M/pACYC-DES

| Strain | L-Cysteine (g/L) |
|---|---|
| MG1655int-4M/pACYC-DES/5JS | 0.28 ± 0.04 |
| MG1655int-4M/pACYC-DES/pMIV-Pnlp23-cysG (Ec) | 0.60 ± 0.01 |
| MG1655int-4M/pACYC-DES/pMIV-Pnlp23-cysGJI (Ec) | 0.51 ± 0.05 |
| MG1655int-4M/pACYC-DES/pMIV-Pnlp8-cysG (Pa) | 0.57 ± 0.05 |
| MG1655int-4M/pACYC-DES/pMIV-Pnlp23-cysGJI (Pa) | 0.58 ± 0.01 |

Explanation of Sequence Listing
SEQ ID NO: 1: Nucleotide sequence of Pnlp0
SEQ ID NO: 2: Nucleotide sequence of Pnlp23
SEQ ID NOS: 3 and 4: Primers for amplification of P. ananatis cysG gene SEQ ID NOS: 5 and 6: Primers for amplification of *P. ananatis* cysJI genes SEQ ID NO: 7: Primer for amplification of *P. ananatis* cysGJI genes SEQ ID NOS: 8 and 9: Primers for amplification of *E. coli* cysG gene SEQ ID NOS: 10 and 11: Primers for amplification of *E. coli* cysJI genes SEQ ID NO: 12: Primer for amplification of *E. coli* cysGJI genes SEQ ID NOS: 13 to 20: Primers P1 to P8

SEQ ID NO: 21: Nucleotide sequence of Pnlp8

SEQ ID NOS: 22 and 23: Primers for amplification of *E. coli* ydeD gene

SEQ ID NOS: 24 to 27: Primers for amplification of cysEX gene

SEQ ID NOS: 28 and 29: Primers for amplification of serA5 gene

SEQ ID NOS: 30 and 31: Primers for amplification of promoter PompA

SEQ ID NOS: 32 and 33: Primers P9 and P10

SEQ ID NO: 34: Nucleotide sequence of Pnlp4

SEQ ID NO: 35: Nucleotide sequence of *E. coli* cysM gene

SEQ ID NO: 36: Amino acid sequence of *E. coli* CysM protein

SEQ ID NOS: 37 and 38: Primers P11 and P12

SEQ ID NO: 39: Nucleotide sequence of *E. coli* cysJ gene

SEQ ID NO: 40: Amino acid sequence of *E. coli* CysJ protein

SEQ ID NO: 41: Nucleotide sequence of *P. ananatis* cysJ gene

SEQ ID NO: 42: Amino acid sequence of *P. ananatis* CysJ protein

SEQ ID NO: 43: Nucleotide sequence of *E. coli* cysI gene

SEQ ID NO: 44: Amino acid sequence of *E. coli* CysI protein

SEQ ID NO: 45: Nucleotide sequence of *P. ananatis* cysI gene

SEQ ID NO: 46: Amino acid sequence of *P. ananatis* CysI protein

SEQ ID NO: 47: Nucleotide sequence of *E. coli* cysG gene

SEQ ID NO: 48: Amino acid sequence of *E. coli* CysG protein

SEQ ID NO: 49: Nucleotide sequence of *P. ananatis* cysG gene

SEQ ID NO: 50: Amino acid sequence of *P. ananatis* CysG protein

SEQ ID NO: 51: Nucleotide sequence of Pnlp0 including ligation site for downstream gene SEQ ID NO: 52: Nucleotide sequence of Pnlp8 including ligation site for downstream gene

What is claimed is:

1. A method for producing L-cysteine, a related substance thereof, or a mixture thereof, which comprises:
   A) culturing a bacterium belonging to the genus *Escherichia* in a medium comprising thiosulfate, which bacterium has L-cysteine-producing ability and is modified so that expression of a gene involved in sulfite reduction is increased by a method selected from the group consisting of increasing copy number of the gene involved in sulfite reduction, modifying an expression control sequence of the gene, and combinations thereof; and
   B) collecting L-cysteine, a related substance thereof, or a mixture thereof from the medium,
   wherein the gene involved in sulfite reduction is a cysG gene, and
   wherein the cysG gene comprises a DNA selected from the group consisting of:
   (a) a DNA comprising the nucleotide sequence of SEQ ID NO: 47 or 49,
   (b) a DNA encoding a protein comprising the amino acid sequence of SEQ ID NO: 48 or 50, and
   (c) a DNA encoding a protein comprising the amino acid sequence of SEQ ID NO: 48 or 50, but which includes one to 10 amino acid substitutions, deletions, insertions, or additions.

2. The method according to claim 1, wherein the bacterium is further modified so that expression of a cysJ gene and a cysI gene is increased by a method selected from the group consisting of increasing copy number of the cysJ and cysI gene, modifying an expression control sequence of the cysJ and cysI gene, and combinations thereof,
   wherein the cysJ gene comprises a DNA selected from the group consisting of:
   (d) a DNA comprising the nucleotide sequence of SEQ ID NO: 39 or 41,
   (e) a DNA hybridizable with a nucleotide sequence complementary to the nucleotide sequence of SEQ ID NO: 39 or 41 under stringent conditions comprising washing at a salt concentration corresponding to 0.1× SSC, 0.1% SDS at 68° C.,
   (f) a DNA encoding a protein comprising the amino acid sequence of SEQ ID NO: 40 or 42, and (g) a DNA encoding a protein comprising the amino acid sequence of SEQ ID NO: 40 or 42 but which includes one to 10 amino acid substitutions, deletions, insertions, or additions; and wherein the cysI gene comprises a DNA selected from the group consisting of:

(h) a DNA comprising the nucleotide sequence of SEQ ID NO: 43 or 45, (i) a DNA hybridizable with a nucleotide sequence complementary to the nucleotide sequence of SEQ ID NO: 43 or 45 under stringent conditions comprising washing at a salt concentration corresponding to 0.1× SSC, 0.1% SDS at 68° C., (j) a DNA encoding a protein comprising the amino acid sequence of SEQ ID NO: 44 or 46, and (k) a DNA encoding a protein comprising the amino acid sequence of SEQ ID NO: 44 or 46 but which includes one to 10 amino acid substitutions, deletions, insertions, or additions.

3. The method according to claim 1, wherein the bacterium is *Escherichia coli*.

4. The method according to claim 1, wherein the bacterium further has a characteristic selected from the group consisting of:

(a) biosynthesis system of L-cysteine is enhanced, (b) secretion system of L-cysteine is enhanced.

5. The method according to claim 1, wherein the related substance is L-cystine or a thiazolidine derivative.

\* \* \* \* \*

SEQUENCE LISTING

```
<160> NUMBER OF SEQ ID NOS: 52

<210> SEQ ID NO 1
<211> LENGTH: 313
<212> TYPE: DNA
<213> ORGANISM: Escherichia coli

<400> SEQUENCE: 1
gcatgcttcc aactgcgcta atgacgcagc tggacgaagg cgggattctc gtcttacccg      60 tagggagga gcaccagtat ttgaaacggg tgcgtcgtcg gggaggcgaa tttattatcg     120
ataccgtgga ggccgtgcgc tttgtccctt tagtgaaggg tgagctggct taaaacgtga    180
ggaaatacct ggattttcc tggttatttt gccgcaggtc agcgtatcgt gaacatcttt     240
tccagtgttc agtagggtgc cttgcacggt aattatgtca ctggttatta accaattttt    300
cctgggggtc gac                                                        313

<210> SEQ ID NO 2
<211> LENGTH: 313
<212> TYPE: DNA
<213> ORGANISM: Escherichia coli

<400> SEQUENCE: 2
gcatgcttcc aactgcgcta atgacgcagc tggacgaagg cgggattctc gtcttacccg      60 tagggagga gcaccagtat ttgaaacggg tgcgtcgtcg gggaggcgaa tttattatcg     120
ataccgtgga ggccgtgcgc tttgtccctt tagtgaaggg tgagctggct taaaacgtga    180
ggaaatacct ggattttcc tggttatttt gccgcaggtc agcgtataat gaagatcttt     240
tccagtgttc agtagggtgc cttgcacggt tataatgtca ctggttatta accaattttt    300
cctgggggtc gac                                                        313

<210> SEQ ID NO 3
<211> LENGTH: 30
<212> TYPE: DNA
```

<213> ORGANISM: Artificial Sequence
<220> FEATURE:
<223> OTHER INFORMATION: CysG Fw(XhoI)

<400> SEQUENCE: 3
acgcctcgag atggattatt tgcctctttt                              30

<210> SEQ ID NO 4
<211> LENGTH: 28
<212> TYPE: DNA
<213> ORGANISM: Artificial Sequence
<220> FEATURE:
<223> OTHER INFORMATION: CysG Rv(XbaI)

<400> SEQUENCE: 4
gctctagatc aagccagatt gacaacgg                                28

<210> SEQ ID NO 5
<211> LENGTH: 30
<212> TYPE: DNA
<213> ORGANISM: Artificial Sequence
<220> FEATURE:
<223> OTHER INFORMATION: CysJ Fw(SalI)

<400> SEQUENCE: 5
acgcgtcgac atgacgactc aggcaccagg                              30

<210> SEQ ID NO 6
<211> LENGTH: 28
<212> TYPE: DNA
<213> ORGANISM: Artificial Sequence
<220> FEATURE:
<223> OTHER INFORMATION: CysI Rv(XbaI)

<400> SEQUENCE: 6
gctctagatc attttgcctc ctgccaga                                28

<210> SEQ ID NO 7
<211> LENGTH: 60
<212> TYPE: DNA
<213> ORGANISM: Artificial Sequence
<220> FEATURE:
<223> OTHER INFORMATION: CysG-JI Rv

<400> SEQUENCE: 7
ctggtgcctg agtcgtcatc gttttcctc tcaagccaga ttgacaacgg cggactcgcg     60

<210> SEQ ID NO 8
<211> LENGTH: 30
<212> TYPE: DNA
<213> ORGANISM: Artificial Sequence
<220> FEATURE:
<223> OTHER INFORMATION: SalI-cysG(Ec)Fw

<400> SEQUENCE: 8
acgcgtcgac atggatcatt tgcctatatt                              30

<210> SEQ ID NO 9
<211> LENGTH: 30
<212> TYPE: DNA
<213> ORGANISM: Artificial Sequence
<220> FEATURE:
<223> OTHER INFORMATION: XbaI-cysG(Ec)Rv

<400> SEQUENCE: 9
gctctagatt aatggttgga gaaccagttc                              30

<210> SEQ ID NO 10
<211> LENGTH: 30
<212> TYPE: DNA
<213> ORGANISM: Artificial Sequence
<220> FEATURE:
<223> OTHER INFORMATION: SalI-cysJ(Ec)Fw

<400> SEQUENCE: 10
acgcgtcgac atgacgacac aggtcccacc                                    30

<210> SEQ ID NO 11
<211> LENGTH: 30
<212> TYPE: DNA
<213> ORGANISM: Artificial Sequence
<220> FEATURE:
<223> OTHER INFORMATION: XbaI-cysI(Ec)Rv

<400> SEQUENCE: 11
gctctagatt aatcccacaa atcacgcgcc                                    30

<210> SEQ ID NO 12
<211> LENGTH: 78
<212> TYPE: DNA
<213> ORGANISM: Artificial Sequence
<220> FEATURE:
<223> OTHER INFORMATION: cysG-JI(Ec)Rv

<400> SEQUENCE: 12
caacgcggaa ggtgggacct gtgtcgtcat gcgtcgttat gttccagttt aatggttgga    60
gaaccagttc agtttatc                                                 78

<210> SEQ ID NO 13
<211> LENGTH: 36
<212> TYPE: DNA
<213> ORGANISM: Artificial Sequence
<220> FEATURE:
<223> OTHER INFORMATION: primer P1

<400> SEQUENCE: 13
agctgagtcg accccccagga aaaattggtt aataac                            36

<210> SEQ ID NO 14
<211> LENGTH: 33
<212> TYPE: DNA
<213> ORGANISM: Artificial Sequence
<220> FEATURE:
<223> OTHER INFORMATION: primer P2

<400> SEQUENCE: 14
agctgagcat gcttccaact gcgctaatga cgc                                33

<210> SEQ ID NO 15
<211> LENGTH: 33
<212> TYPE: DNA
<213> ORGANISM: Artificial Sequence
<220> FEATURE:
<223> OTHER INFORMATION: primer P3

<400> SEQUENCE: 15
agctgatcta gaaaacagaa tttgcctggc ggc                                33

<210> SEQ ID NO 16
<211> LENGTH: 33
<212> TYPE: DNA

```
<213> ORGANISM: Artificial Sequence
<220> FEATURE:
<223> OTHER INFORMATION: primer P4

<400> SEQUENCE: 16
agctgaggat ccaggaagag tttgtagaaa cgc                                    33

<210> SEQ ID NO 17
<211> LENGTH: 32
<212> TYPE: DNA
<213> ORGANISM: Artificial Sequence
<220> FEATURE:
<223> OTHER INFORMATION: primer P5

<400> SEQUENCE: 17
agctgagtcg acgtgttcgc tgaatacggg gt                                     32

<210> SEQ ID NO 18
<211> LENGTH: 32
<212> TYPE: DNA
<213> ORGANISM: Artificial Sequence
<220> FEATURE:
<223> OTHER INFORMATION: primer P6

<400> SEQUENCE: 18
agctgatcta gagaaagcat caggattgca gc                                     32

<210> SEQ ID NO 19
<211> LENGTH: 59
<212> TYPE: DNA
<213> ORGANISM: Artificial Sequence
<220> FEATURE:
<223> OTHER INFORMATION: primer P7
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 19
atcgtgaaga tcttttccag tgttnannag ggtgccttgc acggtnatna ngtcactgg        59

<210> SEQ ID NO 20
<211> LENGTH: 32
<212> TYPE: DNA
<213> ORGANISM: Artificial Sequence
<220> FEATURE:
<223> OTHER INFORMATION: primer P8
<220> FEATURE:
<221> NAME/KEY: misc_feature
<222> LOCATION: (16)..(20)
<223> OTHER INFORMATION: n is a, c, g, or t

<400> SEQUENCE: 20
tggaaaagat cttcannnnn cgctgacctg cg                                     32
```

<210> SEQ ID NO 21
<211> LENGTH: 312
<212> TYPE: DNA
<213> ORGANISM: Escherichia coli

<400> SEQUENCE: 21

```
gcatgcttcc aactgcgcta atgacgcagc tggacgaagg cgggattctc gtcttacccg      60 tagggagga gcaccagtat ttgaaacggg tgcgtcgtcg gggaggcgaa tttattatcg     120
ataccgtgga ggccgtgcgc tttgtccctt tagtgaaggg tgagctggct taaaacgtga    180
ggaaatacct ggattttcc tggttattt gccgcaggtc agcgtataat gaagatcttt      240
tccagtgttg acaagggtcc ttgcacggtt ataatgtcac tggttattaa ccaatttttc    300
ctgggggtcg ac                                                         312
```

<210> SEQ ID NO 22
<211> LENGTH: 33
<212> TYPE: DNA
<213> ORGANISM: Artificial Sequence
<220> FEATURE:
<223> OTHER INFORMATION: ydeD299F

<400> SEQUENCE: 22

```
agctgagtcg acatgtcgcg aaaagatggg gtg                                   33
```

<210> SEQ ID NO 23
<211> LENGTH: 33
<212> TYPE: DNA
<213> ORGANISM: Artificial Sequence
<220> FEATURE:
<223> OTHER INFORMATION: ydeD299R

<400> SEQUENCE: 23

```
agctgatcta gagtttgttc tggccccgac atc                                   33
```

<210> SEQ ID NO 24
<211> LENGTH: 33
<212> TYPE: DNA
<213> ORGANISM: Artificial Sequence
<220> FEATURE:
<223> OTHER INFORMATION: cysEF

<400> SEQUENCE: 24

```
agctgagtcg acatgtcgtg tgaagaactg gaa                                   33
```

<210> SEQ ID NO 25
<211> LENGTH: 21
<212> TYPE: DNA
<213> ORGANISM: Artificial Sequence
<220> FEATURE:
<223> OTHER INFORMATION: cysEX-1

<400> SEQUENCE: 25

```
atcaccgccg cttcaccaac g                                                21
```

<210> SEQ ID NO 26
<211> LENGTH: 21
<212> TYPE: DNA
<213> ORGANISM: Artificial Sequence
<220> FEATURE:
<223> OTHER INFORMATION: cysEX-2

<400> SEQUENCE: 26
```

```
cgttggtgaa gcggcggtga t                                               21
```

<210> SEQ ID NO 27
<211> LENGTH: 33
<212> TYPE: DNA
<213> ORGANISM: Artificial Sequence
<220> FEATURE:
<223> OTHER INFORMATION: cysER

<400> SEQUENCE: 27

```
agctgatcta gaatagatga ttacatcgca tcc                                  33
```

<210> SEQ ID NO 28
<211> LENGTH: 33
<212> TYPE: DNA
<213> ORGANISM: Artificial Sequence
<220> FEATURE:
<223> OTHER INFORMATION: serA5F

<400> SEQUENCE: 28

```
agctgagtcg acatggcaaa ggtatcgctg gag                                  33
```

<210> SEQ ID NO 29
<211> LENGTH: 35
<212> TYPE: DNA
<213> ORGANISM: Artificial Sequence
<220> FEATURE:
<223> OTHER INFORMATION: serA5R

<400> SEQUENCE: 29

```
agctgatcta gattacagca gacgggcgcg aatgg                                35
```

<210> SEQ ID NO 30
<211> LENGTH: 34
<212> TYPE: DNA
<213> ORGANISM: Artificial Sequence
<220> FEATURE:
<223> OTHER INFORMATION: PrOMPAF

<400> SEQUENCE: 30

```
agctgagtcg accgcctcgt tatcatccaa aatc                                 34
```

<210> SEQ ID NO 31
<211> LENGTH: 33
<212> TYPE: DNA
<213> ORGANISM: Artificial Sequence
<220> FEATURE:
<223> OTHER INFORMATION: PrOMPAR

<400> SEQUENCE: 31

```
agctgagcat gcactaattt tccttgcgga ggc                                  33
```

<210> SEQ ID NO 32
<211> LENGTH: 43
<212> TYPE: DNA
<213> ORGANISM: Artificial Sequence
<220> FEATURE:
<223> OTHER INFORMATION: primer P9

<400> SEQUENCE: 32

```
agctgaaagc ttgcatgcac gcgtggcgat ctggcctgac tgc                       43
```

<210> SEQ ID NO 33
<211> LENGTH: 39
<212> TYPE: DNA
<213> ORGANISM: Artificial Sequence -continued

```
<220> FEATURE:
<223> OTHER INFORMATION: primer P10

<400> SEQUENCE: 33
agctgagtcg accccgtggt ggcaaccttt aaaaaactg                                   39

<210> SEQ ID NO 34
<211> LENGTH: 192
<212> TYPE: DNA
<213> ORGANISM: Pantoea ananatis

<400> SEQUENCE: 34
gcatgcacgc gtggcgatct ggcctgactg ccttgttagc atttcttcat aactgtttca           60
tggaatcagg tagttgatat tgctactatc cagttcattc aacgaaaatc cagcgtttaa          120
cgtgccgcac agtgtattgt gctggtgaga cgagtaagtc agttttttaa aggttgccac          180
cacggggtcg ac                                                              192

<210> SEQ ID NO 35
<211> LENGTH: 912
<212> TYPE: DNA
<213> ORGANISM: Escherichia coli
<220> FEATURE:
<221> NAME/KEY: CDS
<222> LOCATION: (1)..(912)

<400> SEQUENCE: 35 gtg agt aca tta gaa caa aca ata ggc aat acg cct ctg gtg aag ttg            48
Met Ser Thr Leu Glu Gln Thr Ile Gly Asn Thr Pro Leu Val Lys Leu
1               5                   10                  15 cag cga atg ggg ccg gat aac ggc agt gaa gtg tgg tta aaa ctg gaa            96
Gln Arg Met Gly Pro Asp Asn Gly Ser Glu Val Trp Leu Lys Leu Glu
            20                  25                  30 ggc aat aac ccg gca ggt tcg gtg aaa gat cgt gcg gca ctt tcg atg           144
Gly Asn Asn Pro Ala Gly Ser Val Lys Asp Arg Ala Ala Leu Ser Met
        35                  40                  45 atc gtc gag gcg gaa aag cgc ggg gaa att aaa ccg ggt gat gtc tta           192
Ile Val Glu Ala Glu Lys Arg Gly Glu Ile Lys Pro Gly Asp Val Leu
50                  55                  60 atc gaa gcc acc agt ggt aac acc ggc att gcg ctg gca atg att gcc           240
Ile Glu Ala Thr Ser Gly Asn Thr Gly Ile Ala Leu Ala Met Ile Ala
65                  70                  75                  80 gcg ctg aaa ggc tat cgc atg aaa ttg ctg atg ccc gac aac atg agc           288
Ala Leu Lys Gly Tyr Arg Met Lys Leu Leu Met Pro Asp Asn Met Ser
                85                  90                  95 cag gaa cgc cgt gcg gcg atg cgt gct tat ggt gcg gaa ctg att ctt           336
Gln Glu Arg Arg Ala Ala Met Arg Ala Tyr Gly Ala Glu Leu Ile Leu
            100                 105                 110 gtc acc aaa gag cag ggc atg gaa ggt gcg cgc gat ctg gcg ctg gag           384
Val Thr Lys Glu Gln Gly Met Glu Gly Ala Arg Asp Leu Ala Leu Glu
        115                 120                 125 atg gcg aat cgt ggc gaa gga aag ctg ctc gat cag ttc aat aat ccc           432
Met Ala Asn Arg Gly Glu Gly Lys Leu Leu Asp Gln Phe Asn Asn Pro
    130                 135                 140 gat aac cct tat gcg cat tac acc acc act ggg ccg gaa atc tgg cag           480
Asp Asn Pro Tyr Ala His Tyr Thr Thr Thr Gly Pro Glu Ile Trp Gln
145                 150                 155                 160 caa acc ggc ggg cgc atc act cat ttt gtc tcc agc atg ggg acg acc           528
Gln Thr Gly Gly Arg Ile Thr His Phe Val Ser Ser Met Gly Thr Thr
                165                 170                 175 ggc act atc acc ggc gtc tca cgc ttt atg cgc gaa caa tcc aaa ccg           576
```

```
Gly Thr Ile Thr Gly Val Ser Arg Phe Met Arg Glu Gln Ser Lys Pro
            180                 185                 190 gtg acc att gtc ggc ctg caa ccg gaa gag ggc agc agc att ccc ggc      624
Val Thr Ile Val Gly Leu Gln Pro Glu Glu Gly Ser Ser Ile Pro Gly
            195                 200                 205 att cgc cgc tgg cct acg gaa tat ctg ccg ggg att ttc aac gct tct      672
Ile Arg Arg Trp Pro Thr Glu Tyr Leu Pro Gly Ile Phe Asn Ala Ser
210                 215                 220 ctg gtg gat gag gtg ctg gat att cat cag cgc gat gcg gaa aac acc      720
Leu Val Asp Glu Val Leu Asp Ile His Gln Arg Asp Ala Glu Asn Thr
225                 230                 235                 240 atg cgc gaa ctg gcg gtg cgg gaa gga ata ttc tgt ggc gtc agc tcc      768
Met Arg Glu Leu Ala Val Arg Glu Gly Ile Phe Cys Gly Val Ser Ser
            245                 250                 255 ggc ggc gcg gtt gcc gga gca ctg cgg gtg gca aaa gct aac cct gac      816
Gly Gly Ala Val Ala Gly Ala Leu Arg Val Ala Lys Ala Asn Pro Asp
            260                 265                 270 gcg gtg gtg gtg gcg atc atc tgc gat cgt ggc gat cgc tac ctt tct      864
Ala Val Val Val Ala Ile Ile Cys Asp Arg Gly Asp Arg Tyr Leu Ser
            275                 280                 285 acc ggg gtg ttt ggg gaa gag cat ttt agc cag ggg gcg ggg att taa      912
Thr Gly Val Phe Gly Glu Glu His Phe Ser Gln Gly Ala Gly Ile
            290                 295                 300

<210> SEQ ID NO 36
<211> LENGTH: 303
<212> TYPE: PRT
<213> ORGANISM: Escherichia coli

<400> SEQUENCE: 36

Met Ser Thr Leu Glu Gln Thr Ile Gly Asn Thr Pro Leu Val Lys Leu
1               5                   10                  15

Gln Arg Met Gly Pro Asp Asn Gly Ser Glu Val Trp Leu Lys Leu Glu
            20                  25                  30

Gly Asn Asn Pro Ala Gly Ser Val Lys Asp Arg Ala Ala Leu Ser Met
        35                  40                  45

Ile Val Glu Ala Glu Lys Arg Gly Glu Ile Lys Pro Gly Asp Val Leu
50                  55                  60

Ile Glu Ala Thr Ser Gly Asn Thr Gly Ile Ala Leu Ala Met Ile Ala
65                  70                  75                  80

Ala Leu Lys Gly Tyr Arg Met Lys Leu Leu Met Pro Asp Asn Met Ser
                85                  90                  95

Gln Glu Arg Arg Ala Ala Met Arg Ala Tyr Gly Ala Glu Leu Ile Leu
            100                 105                 110

Val Thr Lys Glu Gln Gly Met Glu Gly Ala Arg Asp Leu Ala Leu Glu
        115                 120                 125

Met Ala Asn Arg Gly Glu Gly Lys Leu Leu Asp Gln Phe Asn Asn Pro
130                 135                 140

Asp Asn Pro Tyr Ala His Tyr Thr Thr Thr Gly Pro Glu Ile Trp Gln
145                 150                 155                 160

Gln Thr Gly Gly Arg Ile Thr His Phe Val Ser Ser Met Gly Thr Thr
                165                 170                 175

Gly Thr Ile Thr Gly Val Ser Arg Phe Met Arg Glu Gln Ser Lys Pro
            180                 185                 190

Val Thr Ile Val Gly Leu Gln Pro Glu Glu Gly Ser Ser Ile Pro Gly
        195                 200                 205

Ile Arg Arg Trp Pro Thr Glu Tyr Leu Pro Gly Ile Phe Asn Ala Ser
```

```
                        210                 215                 220
Leu Val Asp Glu Val Leu Asp Ile His Gln Arg Asp Ala Glu Asn Thr
225                 230                 235                 240

Met Arg Glu Leu Ala Val Arg Glu Gly Ile Phe Cys Gly Val Ser Ser
                245                 250                 255

Gly Gly Ala Val Ala Gly Ala Leu Arg Val Ala Lys Ala Asn Pro Asp
                260                 265                 270

Ala Val Val Ala Ile Ile Cys Asp Arg Gly Asp Arg Tyr Leu Ser
                275                 280                 285

Thr Gly Val Phe Gly Glu Glu His Phe Ser Gln Gly Ala Gly Ile
                290                 295                 300

<210> SEQ ID NO 37
<211> LENGTH: 35
<212> TYPE: DNA
<213> ORGANISM: Artificial Sequence
<220> FEATURE:
<223> OTHER INFORMATION: primer P11

<400> SEQUENCE: 37
agctgagtcg acgtgagtac attagaacaa acaat                              35

<210> SEQ ID NO 38
<211> LENGTH: 33
<212> TYPE: DNA
<213> ORGANISM: Artificial Sequence
<220> FEATURE:
<223> OTHER INFORMATION: primer P12

<400> SEQUENCE: 38
agctgatcta gaagtctccg atgctattaa tcc                                33

<210> SEQ ID NO 39
<211> LENGTH: 1800
<212> TYPE: DNA
<213> ORGANISM: Escherichia coli
<220> FEATURE:
<221> NAME/KEY: CDS
<222> LOCATION: (1)..(1800)

<400> SEQUENCE: 39 atg acg aca cag gtc cca cct tcc gcg ttg ctt ccg ttg aac ccg gag    48
Met Thr Thr Gln Val Pro Pro Ser Ala Leu Leu Pro Leu Asn Pro Glu
1               5                   10                  15 caa ctg gca cgc ctt cag gcg gcc acg acc gat tta act ccc acc cag    96
Gln Leu Ala Arg Leu Gln Ala Ala Thr Thr Asp Leu Thr Pro Thr Gln
                20                  25                  30 ctt gcc tgg gtt tct ggc tat ttc tgg ggc gta ctc aat cag cag cct   144
Leu Ala Trp Val Ser Gly Tyr Phe Trp Gly Val Leu Asn Gln Gln Pro
            35                  40                  45 gct gcg ctt gca gcg acg cca gcg cca gcc gca gaa atg ccg ggt ata   192
Ala Ala Leu Ala Ala Thr Pro Ala Pro Ala Ala Glu Met Pro Gly Ile
        50                  55                  60 act att atc tcc gcc tcg caa acc ggc aat gcg cgc cgg gtt gct gaa   240
Thr Ile Ile Ser Ala Ser Gln Thr Gly Asn Ala Arg Arg Val Ala Glu
65                  70                  75                  80 gca tta cgt gat gat tta tta gca gca aaa ctg aac gtt aag ctg gtg   288
Ala Leu Arg Asp Asp Leu Leu Ala Ala Lys Leu Asn Val Lys Leu Val
                85                  90                  95 aac gcg ggc gac tat aaa ttc aaa caa atc gcc agc gaa aaa ctg ctc   336
Asn Ala Gly Asp Tyr Lys Phe Lys Gln Ile Ala Ser Glu Lys Leu Leu
                100                 105                 110
```

| | | |
|---|---|---|
| atc gta gtg acg tca acg caa ggg gaa ggg gaa ccg ccg gaa gaa gcc<br>Ile Val Val Thr Ser Thr Gln Gly Glu Gly Glu Pro Pro Glu Glu Ala<br>115                           120                        125 | | 384 |
| gtc gcg ctg cat aag ttc ctg ttc tcc aaa aaa gcg cca aag ctg gaa<br>Val Ala Leu His Lys Phe Leu Phe Ser Lys Lys Ala Pro Lys Leu Glu<br>    130                        135                        140 | | 432 |
| aac acc gcg ttt gcc gtg ttt agc ctc ggc gat agc tct tat gaa ttt<br>Asn Thr Ala Phe Ala Val Phe Ser Leu Gly Asp Ser Ser Tyr Glu Phe<br>145                         150                    155                  160 | | 480 |
| ttc tgc cag tcc ggg aaa gat ttc gac agc aag ctg gcg gaa ctg ggt<br>Phe Cys Gln Ser Gly Lys Asp Phe Asp Ser Lys Leu Ala Glu Leu Gly<br>                165                    170                    175 | | 528 |
| ggt gaa cgc ctg ctc gac cgt gtc gat gcc gat gtt gaa tac cag gct<br>Gly Glu Arg Leu Leu Asp Arg Val Asp Ala Asp Val Glu Tyr Gln Ala<br>180                         185                    190 | | 576 |
| gct gcc agc gag tgg cgc gcc cgc gtg gtt gat gcg ctt aaa tcg cgt<br>Ala Ala Ser Glu Trp Arg Ala Arg Val Val Asp Ala Leu Lys Ser Arg<br>    195                        200                    205 | | 624 |
| gcg cct gtc gcg gca cct tcg caa tcc gtc gct act ggc gcg gta aat<br>Ala Pro Val Ala Ala Pro Ser Gln Ser Val Ala Thr Gly Ala Val Asn<br>210                         215                    220 | | 672 |
| gaa atc cac acc agc ccg tac agc aaa gac gcg ccg ctg gtg gct agc<br>Glu Ile His Thr Ser Pro Tyr Ser Lys Asp Ala Pro Leu Val Ala Ser<br>225                         230                    235                  240 | | 720 |
| ctc tct gtt aac cag aaa att acc ggg cgt aac tct gaa aaa gac gtt<br>Leu Ser Val Asn Gln Lys Ile Thr Gly Arg Asn Ser Glu Lys Asp Val<br>                245                    250                    255 | | 768 |
| cgc cat atc gaa att gac tta ggt gac tcg ggc atg cgt tac cag ccg<br>Arg His Ile Glu Ile Asp Leu Gly Asp Ser Gly Met Arg Tyr Gln Pro<br>260                         265                    270 | | 816 |
| ggt gac gcg ctg ggc gtc tgg tat cag aac gat ccg gca ctg gtg aaa<br>Gly Asp Ala Leu Gly Val Trp Tyr Gln Asn Asp Pro Ala Leu Val Lys<br>    275                        280                    285 | | 864 |
| gaa ctt gtc gaa ctg ctg tgg ctg aaa ggc gat gaa cct gtc acc gtc<br>Glu Leu Val Glu Leu Leu Trp Leu Lys Gly Asp Glu Pro Val Thr Val<br>290                         295                    300 | | 912 |
| gag ggc aaa acg ttg cct ctg aac gaa gcg cta cag tgg cac ttc gaa<br>Glu Gly Lys Thr Leu Pro Leu Asn Glu Ala Leu Gln Trp His Phe Glu<br>305                         310                    315                  320 | | 960 |
| ctg acc gtc aac acc gcc aac att gtt gag aat tac gcc acg ctt acc<br>Leu Thr Val Asn Thr Ala Asn Ile Val Glu Asn Tyr Ala Thr Leu Thr<br>                325                    330                    335 | | 1008 |
| cgc agt gaa aca ctg ctg ccg ctg gtg ggc gat aaa gcg aag tta cag<br>Arg Ser Glu Thr Leu Leu Pro Leu Val Gly Asp Lys Ala Lys Leu Gln<br>    340                        345                    350 | | 1056 |
| cat tac gcc gcg acg acg ccg att gtt gac atg gtg cgt ttc tcc ccg<br>His Tyr Ala Ala Thr Thr Pro Ile Val Asp Met Val Arg Phe Ser Pro<br>355                         360                    365 | | 1104 |
| gca cag ctt gat gcc gaa gcg cta att aat ctg ctg cgc ccg ctg acg<br>Ala Gln Leu Asp Ala Glu Ala Leu Ile Asn Leu Leu Arg Pro Leu Thr<br>    370                        375                    380 | | 1152 |
| ccg cgt ctg tat tcc atc gcc tcc tcg cag gcg gaa gtc gag aac gaa<br>Pro Arg Leu Tyr Ser Ile Ala Ser Ser Gln Ala Glu Val Glu Asn Glu<br>385                         390                    395                  400 | | 1200 |
| gta cac gtc acc gtt ggt gtg gtg cgt tac gac gtg gaa ggc cgc gcc<br>Val His Val Thr Val Gly Val Val Arg Tyr Asp Val Glu Gly Arg Ala<br>                405                    410                    415 | | 1248 |
| cgt gcc ggt ggt gcc tcc agc ttc ctc gct gac cgc gtg gaa gaa gag<br>Arg Ala Gly Gly Ala Ser Ser Phe Leu Ala Asp Arg Val Glu Glu Glu | | 1296 |

```
                    420             425             430
ggc gaa gtc cgc gta ttt atc gaa cat aac gat aac ttc cgc ctg cca       1344
Gly Glu Val Arg Val Phe Ile Glu His Asn Asp Asn Phe Arg Leu Pro
        435                 440                 445 gcc aat cca gaa acc ccg gtg att atg att ggc cca ggc acc ggt att       1392
Ala Asn Pro Glu Thr Pro Val Ile Met Ile Gly Pro Gly Thr Gly Ile
450                 455                 460 gcg ccg ttc cgc gcc ttt atg cag caa cgc gcc gcc gac gaa gcg cca       1440
Ala Pro Phe Arg Ala Phe Met Gln Gln Arg Ala Ala Asp Glu Ala Pro
465                 470                 475                 480 ggt aaa aac tgg ctg ttc ttt ggt aat ccg cac ttt acg gaa gac ttc       1488
Gly Lys Asn Trp Leu Phe Phe Gly Asn Pro His Phe Thr Glu Asp Phe
                485                 490                 495 ctg tac cag gtg gag tgg cag cgc tac gtc aaa gat ggc gtg ctg aca       1536
Leu Tyr Gln Val Glu Trp Gln Arg Tyr Val Lys Asp Gly Val Leu Thr
        500                 505                 510 cgt atc gat ctt gcc tgg tcg cgc gat caa aaa gaa aaa gtt tac gta       1584
Arg Ile Asp Leu Ala Trp Ser Arg Asp Gln Lys Glu Lys Val Tyr Val
        515                 520                 525 caa gac aaa ctg cgc gaa cag ggc gcg gag ctg tgg cgc tgg atc aat       1632
Gln Asp Lys Leu Arg Glu Gln Gly Ala Glu Leu Trp Arg Trp Ile Asn
530                 535                 540 gat ggt gcc cac att tat gtc tgc ggc gac gct aat cgc atg gcg aaa       1680
Asp Gly Ala His Ile Tyr Val Cys Gly Asp Ala Asn Arg Met Ala Lys
545                 550                 555                 560 gac gtt gag cag gca ctt ctg gaa gtg att gcc gaa ttt ggt ggc atg       1728
Asp Val Glu Gln Ala Leu Leu Glu Val Ile Ala Glu Phe Gly Gly Met
                565                 570                 575 gac acc gaa gcg gcg gat gaa ttt tta agt gag ctg cgc gta gag cgc       1776
Asp Thr Glu Ala Ala Asp Glu Phe Leu Ser Glu Leu Arg Val Glu Arg
        580                 585                 590 cgt tat cag cga gat gtc tac taa                                       1800
Arg Tyr Gln Arg Asp Val Tyr
        595

<210> SEQ ID NO 40
<211> LENGTH: 599
<212> TYPE: PRT
<213> ORGANISM: Escherichia coli

<400> SEQUENCE: 40

Met Thr Thr Gln Val Pro Pro Ser Ala Leu Leu Pro Leu Asn Pro Glu
1               5                   10                  15

Gln Leu Ala Arg Leu Gln Ala Ala Thr Thr Asp Leu Thr Pro Thr Gln
            20                  25                  30

Leu Ala Trp Val Ser Gly Tyr Phe Trp Gly Val Leu Asn Gln Gln Pro
        35                  40                  45

Ala Ala Leu Ala Ala Thr Pro Ala Pro Ala Ala Glu Met Pro Gly Ile
    50                  55                  60

Thr Ile Ile Ser Ala Ser Gln Thr Gly Asn Ala Arg Arg Val Ala Glu
65                  70                  75                  80

Ala Leu Arg Asp Asp Leu Leu Ala Ala Lys Leu Asn Val Lys Leu Val
                85                  90                  95

Asn Ala Gly Asp Tyr Lys Phe Lys Gln Ile Ala Ser Glu Lys Leu Leu
            100                 105                 110

Ile Val Val Thr Ser Thr Gln Gly Glu Gly Glu Pro Pro Glu Glu Ala
        115                 120                 125

Val Ala Leu His Lys Phe Leu Phe Ser Lys Lys Ala Pro Lys Leu Glu
```

-continued

```
               130                 135                 140
Asn Thr Ala Phe Ala Val Phe Ser Leu Gly Asp Ser Ser Tyr Glu Phe
145                 150                 155                 160

Phe Cys Gln Ser Gly Lys Asp Phe Asp Ser Lys Leu Ala Glu Leu Gly
                165                 170                 175

Gly Glu Arg Leu Leu Asp Arg Val Asp Ala Asp Val Glu Tyr Gln Ala
                180                 185                 190

Ala Ala Ser Glu Trp Arg Ala Arg Val Val Asp Ala Leu Lys Ser Arg
                195                 200                 205

Ala Pro Val Ala Ala Pro Ser Gln Ser Val Ala Thr Gly Ala Val Asn
210                 215                 220

Glu Ile His Thr Ser Pro Tyr Ser Lys Asp Ala Pro Leu Val Ala Ser
225                 230                 235                 240

Leu Ser Val Asn Gln Lys Ile Thr Gly Arg Asn Ser Glu Lys Asp Val
                245                 250                 255

Arg His Ile Glu Ile Asp Leu Gly Asp Ser Gly Met Arg Tyr Gln Pro
                260                 265                 270

Gly Asp Ala Leu Gly Val Trp Tyr Gln Asn Asp Pro Ala Leu Val Lys
                275                 280                 285

Glu Leu Val Glu Leu Leu Trp Leu Lys Gly Asp Glu Pro Val Thr Val
                290                 295                 300

Glu Gly Lys Thr Leu Pro Leu Asn Glu Ala Leu Gln Trp His Phe Glu
305                 310                 315                 320

Leu Thr Val Asn Thr Ala Asn Ile Val Glu Asn Tyr Ala Thr Leu Thr
                325                 330                 335

Arg Ser Glu Thr Leu Leu Pro Leu Val Gly Asp Lys Ala Lys Leu Gln
                340                 345                 350

His Tyr Ala Ala Thr Thr Pro Ile Val Asp Met Val Arg Phe Ser Pro
                355                 360                 365

Ala Gln Leu Asp Ala Glu Ala Leu Ile Asn Leu Leu Arg Pro Leu Thr
                370                 375                 380

Pro Arg Leu Tyr Ser Ile Ala Ser Ser Gln Ala Glu Val Glu Asn Glu
385                 390                 395                 400

Val His Val Thr Val Gly Val Val Arg Tyr Asp Val Glu Gly Arg Ala
                405                 410                 415

Arg Ala Gly Gly Ala Ser Ser Phe Leu Ala Asp Arg Val Glu Glu Glu
                420                 425                 430

Gly Glu Val Arg Val Phe Ile Glu His Asn Asp Asn Phe Arg Leu Pro
                435                 440                 445

Ala Asn Pro Glu Thr Pro Val Ile Met Ile Gly Pro Gly Thr Gly Ile
450                 455                 460

Ala Pro Phe Arg Ala Phe Met Gln Gln Arg Ala Ala Asp Glu Ala Pro
465                 470                 475                 480

Gly Lys Asn Trp Leu Phe Phe Gly Asn Pro His Phe Thr Glu Asp Phe
                485                 490                 495

Leu Tyr Gln Val Glu Trp Gln Arg Tyr Val Lys Asp Gly Val Leu Thr
                500                 505                 510

Arg Ile Asp Leu Ala Trp Ser Arg Asp Gln Lys Glu Lys Val Tyr Val
                515                 520                 525

Gln Asp Lys Leu Arg Glu Gln Gly Ala Glu Leu Trp Arg Trp Ile Asn
                530                 535                 540

Asp Gly Ala His Ile Tyr Val Cys Gly Asp Ala Asn Arg Met Ala Lys
545                 550                 555                 560
```

Asp Val Glu Gln Ala Leu Leu Glu Val Ile Ala Glu Phe Gly Gly Met
            565                 570                 575

Asp Thr Glu Ala Ala Asp Glu Phe Leu Ser Glu Leu Arg Val Glu Arg
        580                 585                 590

Arg Tyr Gln Arg Asp Val Tyr
        595

<210> SEQ ID NO 41
<211> LENGTH: 1803
<212> TYPE: DNA
<213> ORGANISM: Pantoea ananatis
<220> FEATURE:
<221> NAME/KEY: CDS
<222> LOCATION: (1)..(1803)

<400> SEQUENCE: 41

| | |
|---|---:|
| atg acg act cag gca cca ggc tca atg ctt ccg ctc tct ccg gag caa<br>Met Thr Thr Gln Ala Pro Gly Ser Met Leu Pro Leu Ser Pro Glu Gln<br>1               5                   10                  15 | 48 |
| ctt gct cgt tta cag gca gca acg aca gat ttt tcc acc act cag atg<br>Leu Ala Arg Leu Gln Ala Ala Thr Thr Asp Phe Ser Thr Thr Gln Met<br>            20                  25                  30 | 96 |
| gcc tgg ctc tct ggc tat ttc tgg ggc atg gtc aat caa atg cca ggc<br>Ala Trp Leu Ser Gly Tyr Phe Trp Gly Met Val Asn Gln Met Pro Gly<br>        35                  40                  45 | 144 |
| cag gcg gtt gcc agc gcg cct gcg cag gct gaa acc ccg gcg att acg<br>Gln Ala Val Ala Ser Ala Pro Ala Gln Ala Glu Thr Pro Ala Ile Thr<br>    50                  55                  60 | 192 |
| ctg ctc tct gcc tca caa acc ggc aat gcc cgc cgg gta gcc gag cag<br>Leu Leu Ser Ala Ser Gln Thr Gly Asn Ala Arg Arg Val Ala Glu Gln<br>65                  70                  75                  80 | 240 |
| tta cgc gat gac ctg cag gcg gca aaa ctg acc gtg aat ctg gtc aac<br>Leu Arg Asp Asp Leu Gln Ala Ala Lys Leu Thr Val Asn Leu Val Asn<br>                85                  90                  95 | 288 |
| gcg ggc gac ttt aaa ttt aag cag att ggc cag gaa aaa att ctg att<br>Ala Gly Asp Phe Lys Phe Lys Gln Ile Gly Gln Glu Lys Ile Leu Ile<br>            100                 105                 110 | 336 |
| gtc gtg acc tcg acg cag ggc gaa ggc gaa cca ccg gaa gag gcc gtt<br>Val Val Thr Ser Thr Gln Gly Glu Gly Glu Pro Pro Glu Glu Ala Val<br>        115                 120                 125 | 384 |
| gcg ctg cat aaa ttc ctg atg tct aag aaa gcg ccc aaa atg gac ggc<br>Ala Leu His Lys Phe Leu Met Ser Lys Lys Ala Pro Lys Met Asp Gly<br>    130                 135                 140 | 432 |
| gcg gcc ttt gcc gtg ttt ggt ctg ggc gat acc tcc tat gaa ttc ttc<br>Ala Ala Phe Ala Val Phe Gly Leu Gly Asp Thr Ser Tyr Glu Phe Phe<br>145                 150                 155                 160 | 480 |
| agc aaa gcg ggc aaa gat ttt gac agc cgc ctg gcc gag ctg ggt gca<br>Ser Lys Ala Gly Lys Asp Phe Asp Ser Arg Leu Ala Glu Leu Gly Ala<br>                165                 170                 175 | 528 |
| gaa cga ctg ctg gat cgg gtc gat gcg gat gtt gaa tat gcc gag cag<br>Glu Arg Leu Leu Asp Arg Val Asp Ala Asp Val Glu Tyr Ala Glu Gln<br>            180                 185                 190 | 576 |
| gcc agc gcc tgg cgc gcg gca att act gcc gca ctg aaa gaa cgc gta<br>Ala Ser Ala Trp Arg Ala Ala Ile Thr Ala Ala Leu Lys Glu Arg Val<br>        195                 200                 205 | 624 |
| ccg gca gcg tca ccg gcc cag agt gcg gca acc gtc gcc ggc agc gtg<br>Pro Ala Ala Ser Pro Ala Gln Ser Ala Ala Thr Val Ala Gly Ser Val<br>    210                 215                 220 | 672 |
| aac gaa gtc ttc acc agc cct tac act aaa gag cag ccg ctt agt gcc<br>Asn Glu Val Phe Thr Ser Pro Tyr Thr Lys Glu Gln Pro Leu Ser Ala | 720 |

-continued

| | | | | | |
|---|---|---|---|---|---|
| 225 | | 230 | | 235 | 240 | agc ctg gcg gtt aac cag aaa att acc ggg cgc gat tcg gac aaa gat    768
Ser Leu Ala Val Asn Gln Lys Ile Thr Gly Arg Asp Ser Asp Lys Asp
                245                 250                 255 gtg cgt cac atc gaa atc gat ctg ggt gat tca gga tta cgc tac cag    816
Val Arg His Ile Glu Ile Asp Leu Gly Asp Ser Gly Leu Arg Tyr Gln
            260                 265                 270 cct ggt gat gcg ctg ggc gtc tgg tat gag aat gac gcg gcc ctg gtt    864
Pro Gly Asp Ala Leu Gly Val Trp Tyr Glu Asn Asp Ala Ala Leu Val
        275                 280                 285 aac gag ctg ctt gaa ctg gtg tgg cta aaa ggc gat gag ccg gtt gag    912
Asn Glu Leu Leu Glu Leu Val Trp Leu Lys Gly Asp Glu Pro Val Glu
    290                 295                 300 gtg cag ggc cag acg ctg cca ttg gca gag gcg ttg cag aaa cat ttt    960
Val Gln Gly Gln Thr Leu Pro Leu Ala Glu Ala Leu Gln Lys His Phe
305                 310                 315                 320 gag cta acg gtt aac acc gcg caa atc gtc gcg cag tac gca gcc tta    1008
Glu Leu Thr Val Asn Thr Ala Gln Ile Val Ala Gln Tyr Ala Ala Leu
                325                 330                 335 gca cgt aac gac gaa ctg ctg tcg ctg gtg gat gac aaa gcc aaa ctg    1056
Ala Arg Asn Asp Glu Leu Leu Ser Leu Val Asp Asp Lys Ala Lys Leu
            340                 345                 350 cag cag tat gcg caa cgc tat ccg att gtt gat atg gtt cgt ctg gca    1104
Gln Gln Tyr Ala Gln Arg Tyr Pro Ile Val Asp Met Val Arg Leu Ala
        355                 360                 365 cca gcc caa ctg agc gca gaa cag tta tcc ggc ttg ctg cgt ccg tta    1152
Pro Ala Gln Leu Ser Ala Glu Gln Leu Ser Gly Leu Leu Arg Pro Leu
    370                 375                 380 acg ccg cgt ctt tac tct atc gct tcg tct cag gcc gaa acc gat acc    1200
Thr Pro Arg Leu Tyr Ser Ile Ala Ser Ser Gln Ala Glu Thr Asp Thr
385                 390                 395                 400 gaa gta cat atc acc gtg ggg gcc gtg cgc ttt gat att gaa ggg cgc    1248
Glu Val His Ile Thr Val Gly Ala Val Arg Phe Asp Ile Glu Gly Arg
                405                 410                 415 ccg cgc ggc ggc ggc gct tcc acc tgg ctg gcg gat cgc att gaa gaa    1296
Pro Arg Gly Gly Gly Ala Ser Thr Trp Leu Ala Asp Arg Ile Glu Glu
            420                 425                 430 gac ggt gag gtg cgc gtg ttt atc gaa cac aac gat aat ttt cgc ctg    1344
Asp Gly Glu Val Arg Val Phe Ile Glu His Asn Asp Asn Phe Arg Leu
        435                 440                 445 ccc gcc aac ccg gat gca ccg gtc att atg att ggg cct ggc acc ggt    1392
Pro Ala Asn Pro Asp Ala Pro Val Ile Met Ile Gly Pro Gly Thr Gly
    450                 455                 460 att gcg ccg ttc cgc gcc ttt atg cag cag cgc gag aac gac ggc gcc    1440
Ile Ala Pro Phe Arg Ala Phe Met Gln Gln Arg Glu Asn Asp Gly Ala
465                 470                 475                 480 agc ggt aaa aac tgg cta ttc ttt ggc aat ccc cac ttt act gac gat    1488
Ser Gly Lys Asn Trp Leu Phe Phe Gly Asn Pro His Phe Thr Asp Asp
                485                 490                 495 ttc ctg tat cag gtg gaa tgg cag aaa tac gtg aaa gat ggc ctg tta    1536
Phe Leu Tyr Gln Val Glu Trp Gln Lys Tyr Val Lys Asp Gly Leu Leu
            500                 505                 510 acg aat atc gat ctg gcc tgg tcg cgc gat cag gcc gag aaa att tac    1584
Thr Asn Ile Asp Leu Ala Trp Ser Arg Asp Gln Ala Glu Lys Ile Tyr
        515                 520                 525 gta caa gat aaa atc cgc gcc aag ggt gcg gag gtg tgg agc tgg tta    1632
Val Gln Asp Lys Ile Arg Ala Lys Gly Ala Glu Val Trp Ser Trp Leu
    530                 535                 540 cag gaa ggc gcg cac ctt tac gtc tgc ggc gac gcc aat cgt atg gca    1680

```
                Gln Glu Gly Ala His Leu Tyr Val Cys Gly Asp Ala Asn Arg Met Ala
                545                 550                 555                 560 aaa gac gtt gag cag gca tta ctg gat gtg gtg gtc gaa cac ggc gct          1728
Lys Asp Val Glu Gln Ala Leu Leu Asp Val Val Val Glu His Gly Ala
                565                 570                 575 atg gat cgt gaa acg gct gac gaa ttt tta agt gag ctg cgc att gag          1776
Met Asp Arg Glu Thr Ala Asp Glu Phe Leu Ser Glu Leu Arg Ile Glu
580                 585                 590 cgc cgt tat cag cga gac gtt tac taa                                      1803
Arg Arg Tyr Gln Arg Asp Val Tyr
                595                 600

<210> SEQ ID NO 42
<211> LENGTH: 600
<212> TYPE: PRT
<213> ORGANISM: Pantoea ananatis

<400> SEQUENCE: 42

Met Thr Thr Gln Ala Pro Gly Ser Met Leu Pro Leu Ser Pro Glu Gln
1               5                   10                  15

Leu Ala Arg Leu Gln Ala Ala Thr Thr Asp Phe Ser Thr Thr Gln Met
            20                  25                  30

Ala Trp Leu Ser Gly Tyr Phe Trp Gly Met Val Asn Gln Met Pro Gly
        35                  40                  45

Gln Ala Val Ala Ser Ala Pro Ala Gln Ala Glu Thr Pro Ala Ile Thr
    50                  55                  60

Leu Leu Ser Ala Ser Gln Thr Gly Asn Ala Arg Arg Val Ala Glu Gln
65                  70                  75                  80

Leu Arg Asp Asp Leu Gln Ala Ala Lys Leu Thr Val Asn Leu Val Asn
                85                  90                  95

Ala Gly Asp Phe Lys Phe Lys Gln Ile Gly Gln Glu Lys Ile Leu Ile
            100                 105                 110

Val Val Thr Ser Thr Gln Gly Glu Gly Glu Pro Pro Glu Glu Ala Val
        115                 120                 125

Ala Leu His Lys Phe Leu Met Ser Lys Lys Ala Pro Lys Met Asp Gly
    130                 135                 140

Ala Ala Phe Ala Val Phe Gly Leu Gly Asp Thr Ser Tyr Glu Phe Phe
145                 150                 155                 160

Ser Lys Ala Gly Lys Asp Phe Asp Ser Arg Leu Ala Glu Leu Gly Ala
                165                 170                 175

Glu Arg Leu Leu Asp Arg Val Asp Ala Asp Val Glu Tyr Ala Glu Gln
            180                 185                 190

Ala Ser Ala Trp Arg Ala Ala Ile Thr Ala Ala Leu Lys Glu Arg Val
        195                 200                 205

Pro Ala Ala Ser Pro Ala Gln Ser Ala Ala Thr Val Ala Gly Ser Val
    210                 215                 220

Asn Glu Val Phe Thr Ser Pro Tyr Thr Lys Glu Gln Pro Leu Ser Ala
225                 230                 235                 240

Ser Leu Ala Val Asn Gln Lys Ile Thr Gly Arg Asp Ser Asp Lys Asp
                245                 250                 255

Val Arg His Ile Glu Ile Asp Leu Gly Asp Ser Gly Leu Arg Tyr Gln
            260                 265                 270

Pro Gly Asp Ala Leu Gly Val Trp Tyr Glu Asn Asp Ala Ala Leu Val
        275                 280                 285

Asn Glu Leu Leu Glu Leu Val Trp Leu Lys Gly Asp Glu Pro Val Glu
    290                 295                 300
```

```
Val Gln Gly Gln Thr Leu Pro Leu Ala Glu Ala Leu Gln Lys His Phe
305                 310                 315                 320

Glu Leu Thr Val Asn Thr Ala Gln Ile Val Ala Gln Tyr Ala Ala Leu
            325                 330                 335

Ala Arg Asn Asp Glu Leu Leu Ser Leu Val Asp Asp Lys Ala Lys Leu
        340                 345                 350

Gln Gln Tyr Ala Gln Arg Tyr Pro Ile Val Asp Met Val Arg Leu Ala
    355                 360                 365

Pro Ala Gln Leu Ser Ala Glu Gln Leu Ser Gly Leu Leu Arg Pro Leu
370                 375                 380

Thr Pro Arg Leu Tyr Ser Ile Ala Ser Ser Gln Ala Glu Thr Asp Thr
385                 390                 395                 400

Glu Val His Ile Thr Val Gly Ala Val Arg Phe Asp Ile Glu Gly Arg
            405                 410                 415

Pro Arg Gly Gly Gly Ala Ser Thr Trp Leu Ala Asp Arg Ile Glu Glu
        420                 425                 430

Asp Gly Glu Val Arg Val Phe Ile Glu His Asn Asp Asn Phe Arg Leu
    435                 440                 445

Pro Ala Asn Pro Asp Ala Pro Val Ile Met Ile Gly Pro Gly Thr Gly
450                 455                 460

Ile Ala Pro Phe Arg Ala Phe Met Gln Gln Arg Glu Asn Asp Gly Ala
465                 470                 475                 480

Ser Gly Lys Asn Trp Leu Phe Phe Gly Asn Pro His Phe Thr Asp Asp
            485                 490                 495

Phe Leu Tyr Gln Val Glu Trp Gln Lys Tyr Val Lys Asp Gly Leu Leu
        500                 505                 510

Thr Asn Ile Asp Leu Ala Trp Ser Arg Asp Gln Ala Glu Lys Ile Tyr
    515                 520                 525

Val Gln Asp Lys Ile Arg Ala Lys Gly Ala Glu Val Trp Ser Trp Leu
530                 535                 540

Gln Glu Gly Ala His Leu Tyr Val Cys Gly Asp Ala Asn Arg Met Ala
545                 550                 555                 560

Lys Asp Val Glu Gln Ala Leu Leu Asp Val Val Glu His Gly Ala
            565                 570                 575

Met Asp Arg Glu Thr Ala Asp Glu Phe Leu Ser Glu Leu Arg Ile Glu
        580                 585                 590

Arg Arg Tyr Gln Arg Asp Val Tyr
    595                 600

<210> SEQ ID NO 43
<211> LENGTH: 1713
<212> TYPE: DNA
<213> ORGANISM: Escherichia coli
<220> FEATURE:
<221> NAME/KEY: CDS
<222> LOCATION: (1)..(1713)

<400> SEQUENCE: 43 atg agc gaa aaa cat cca ggg cct tta gtg gtc gaa gga aaa ctg aca      48
Met Ser Glu Lys His Pro Gly Pro Leu Val Val Glu Gly Lys Leu Thr
1               5                   10                  15 gac gcc gag cgc atg aag cat gaa agc aac tac ctg cgc ggc acc att     96
Asp Ala Glu Arg Met Lys His Glu Ser Asn Tyr Leu Arg Gly Thr Ile
            20                  25                  30 gcg gaa gat tta aac gac ggt ctg acc ggc ggc ttt aag ggc gac aac    144
Ala Glu Asp Leu Asn Asp Gly Leu Thr Gly Gly Phe Lys Gly Asp Asn
```

-continued

```
              35                  40                  45
ttc ctg ctg att cgc ttc cac ggc atg tat cag cag gat gac cgc gac      192
Phe Leu Leu Ile Arg Phe His Gly Met Tyr Gln Gln Asp Asp Arg Asp
     50                  55                  60 atc cgc gcc gaa cgt gct gaa cag aag ctg gag ccg cgc cac gcg atg      240
Ile Arg Ala Glu Arg Ala Glu Gln Lys Leu Glu Pro Arg His Ala Met
 65                  70                  75                  80 ctg ctt cgc tgt cgt ctg ccg ggt ggg gtg att acc act aaa cag tgg      288
Leu Leu Arg Cys Arg Leu Pro Gly Gly Val Ile Thr Thr Lys Gln Trp
                 85                  90                  95 cag gcg atc gac aaa ttt gcc ggt gaa aac acc atc tat ggc agc att      336
Gln Ala Ile Asp Lys Phe Ala Gly Glu Asn Thr Ile Tyr Gly Ser Ile
             100                 105                 110 cgc ctg acc aac cgc cag acg ttt cag ttc cac ggc att ctg aaa aag      384
Arg Leu Thr Asn Arg Gln Thr Phe Gln Phe His Gly Ile Leu Lys Lys
         115                 120                 125 aac gtc aaa ccg gtg cac cag atg ctg cac tcg gtc ggt ctt gat gcg      432
Asn Val Lys Pro Val His Gln Met Leu His Ser Val Gly Leu Asp Ala
     130                 135                 140 ctg gcg aca gct aac gac atg aac cgt aac gta ctc tgc acc tcg aac      480
Leu Ala Thr Ala Asn Asp Met Asn Arg Asn Val Leu Cys Thr Ser Asn
145                 150                 155                 160 cct tac gag tcg cag ctg cac gcg gaa gcg tac gag tgg gcg aag aag      528
Pro Tyr Glu Ser Gln Leu His Ala Glu Ala Tyr Glu Trp Ala Lys Lys
                 165                 170                 175 att tct gag cat ctg ttg cct cgt acc cgc gcg tat gcg gag atc tgg      576
Ile Ser Glu His Leu Leu Pro Arg Thr Arg Ala Tyr Ala Glu Ile Trp
             180                 185                 190 ctc gac cag gaa aaa gtc gcc act act gat gaa gaa ccg atc ctc ggc      624
Leu Asp Gln Glu Lys Val Ala Thr Thr Asp Glu Glu Pro Ile Leu Gly
         195                 200                 205 cag acc tac ctg ccg cgt aaa ttc aaa acc acg gta gtg atc ccg cca      672
Gln Thr Tyr Leu Pro Arg Lys Phe Lys Thr Thr Val Val Ile Pro Pro
     210                 215                 220 cag aac gat atc gat ctg cac gcc aac gac atg aac ttc gtg gcg atc      720
Gln Asn Asp Ile Asp Leu His Ala Asn Asp Met Asn Phe Val Ala Ile
225                 230                 235                 240 gcc gaa aac ggc aag ctg gtg ggc ttt aac ctg ttg gtg ggc ggt ggg      768
Ala Glu Asn Gly Lys Leu Val Gly Phe Asn Leu Leu Val Gly Gly Gly
                 245                 250                 255 ctt tcc atc gaa cac ggc aac aag aaa acc tac gcc cgc acc gcg agt      816
Leu Ser Ile Glu His Gly Asn Lys Lys Thr Tyr Ala Arg Thr Ala Ser
             260                 265                 270 gag ttt ggc tat ctg ccg ctg gag cat acg ctg gcg gtg gcc gaa gcc      864
Glu Phe Gly Tyr Leu Pro Leu Glu His Thr Leu Ala Val Ala Glu Ala
         275                 280                 285 gtc gtg aca act cag cgt gac tgg ggt aac cga acc gat cgt aaa aat      912
Val Val Thr Thr Gln Arg Asp Trp Gly Asn Arg Thr Asp Arg Lys Asn
     290                 295                 300 gcc aaa acc aaa tac acg ctg gag cgc gtg ggg gtt gag acg ttt aaa      960
Ala Lys Thr Lys Tyr Thr Leu Glu Arg Val Gly Val Glu Thr Phe Lys
305                 310                 315                 320 gcg gaa gtg gag cgt cgc gcg ggg atc aaa ttt gaa ccg atc cgt cca     1008
Ala Glu Val Glu Arg Arg Ala Gly Ile Lys Phe Glu Pro Ile Arg Pro
                 325                 330                 335 tat gag ttc acc gga cga ggc gat cgt att ggc tgg gtt aag ggc att     1056
Tyr Glu Phe Thr Gly Arg Gly Asp Arg Ile Gly Trp Val Lys Gly Ile
             340                 345                 350 gat gat aac tgg cac ctg acg ctg ttt atc gaa aat ggt cgc atc ctt     1104
```

```
                                                                 1152
gat tat ccg gcg cgt ccg ctg aaa acc ggc ctg ctg gag atc gcg aag
Asp Tyr Pro Ala Arg Pro Leu Lys Thr Gly Leu Leu Glu Ile Ala Lys
    370                 375                 380

1200
atc cac aaa ggc gat ttc cgc att acg gcg aac cag aat ctg atc atc
Ile His Lys Gly Asp Phe Arg Ile Thr Ala Asn Gln Asn Leu Ile Ile
385                 390                 395                 400

1248
gcc ggt gta ccg gaa agc gag aaa gcg aag atc gag aag atc gcc aaa
Ala Gly Val Pro Glu Ser Glu Lys Ala Lys Ile Glu Lys Ile Ala Lys
                405                 410                 415

1296
gag agc ggg tta atg aat gcc gtc acg ccg cag cgt gaa aac tcg atg
Glu Ser Gly Leu Met Asn Ala Val Thr Pro Gln Arg Glu Asn Ser Met
        420                 425                 430

1344
gct tgc gtg tca ttc ccg act tgc ccg ctg gcg atg gcg gaa gca gag
Ala Cys Val Ser Phe Pro Thr Cys Pro Leu Ala Met Ala Glu Ala Glu
            435                 440                 445

1392
cgt ttc ctg ccg tct ttt atc gac aac atc gat aat tta atg gcg aaa
Arg Phe Leu Pro Ser Phe Ile Asp Asn Ile Asp Asn Leu Met Ala Lys
    450                 455                 460

1440
cat ggt gtc agc gat gag cat atc gtg atg cgt gta aca ggc tgc ccg
His Gly Val Ser Asp Glu His Ile Val Met Arg Val Thr Gly Cys Pro
465                 470                 475                 480

1488
aac ggt tgt ggt cgc gcg atg ctg gcg gaa gtg ggc ctg gtg ggt aaa
Asn Gly Cys Gly Arg Ala Met Leu Ala Glu Val Gly Leu Val Gly Lys
                485                 490                 495

1536
gcg ccg ggt cgc tac aac ctg cat ctt ggc ggc aac cgc att ggg aca
Ala Pro Gly Arg Tyr Asn Leu His Leu Gly Gly Asn Arg Ile Gly Thr
        500                 505                 510

1584
cgt atc cca cgg atg tat aaa gaa aac atc acc gag ccg gaa atc ctg
Arg Ile Pro Arg Met Tyr Lys Glu Asn Ile Thr Glu Pro Glu Ile Leu
            515                 520                 525

1632
gcg tcg ctt gat gaa ctg ata ggg cgc tgg gcg aaa gag cgc gaa gcg
Ala Ser Leu Asp Glu Leu Ile Gly Arg Trp Ala Lys Glu Arg Glu Ala
    530                 535                 540

1680
ggt gaa ggc ttc ggc gac ttt acg gtg cgt gcg ggc atc att cgc ccg
Gly Glu Gly Phe Gly Asp Phe Thr Val Arg Ala Gly Ile Ile Arg Pro
545                 550                 555                 560

1713
gtg ctc gat ccg gcg cgt gat ttg tgg gat taa
Val Leu Asp Pro Ala Arg Asp Leu Trp Asp
                565                 570

<210> SEQ ID NO 44
<211> LENGTH: 570
<212> TYPE: PRT
<213> ORGANISM: Escherichia coli

<400> SEQUENCE: 44

Met Ser Glu Lys His Pro Gly Pro Leu Val Val Glu Gly Lys Leu Thr
1               5                   10                  15

Asp Ala Glu Arg Met Lys His Glu Ser Asn Tyr Leu Arg Gly Thr Ile
                20                  25                  30

Ala Glu Asp Leu Asn Asp Gly Leu Thr Gly Gly Phe Lys Gly Asp Asn
            35                  40                  45

Phe Leu Leu Ile Arg Phe His Gly Met Tyr Gln Gln Asp Asp Arg Asp
    50                  55                  60

Ile Arg Ala Glu Arg Ala Glu Gln Lys Leu Glu Pro Arg His Ala Met
65                  70                  75                  80

Leu Leu Arg Cys Arg Leu Pro Gly Gly Val Ile Thr Thr Lys Gln Trp
```

-continued

```
                85                  90                  95
Gln Ala Ile Asp Lys Phe Ala Gly Glu Asn Thr Ile Tyr Gly Ser Ile
            100                 105                 110
Arg Leu Thr Asn Arg Gln Thr Phe Gln Phe His Gly Ile Leu Lys Lys
            115                 120                 125
Asn Val Lys Pro Val His Gln Met Leu His Ser Val Gly Leu Asp Ala
            130                 135                 140
Leu Ala Thr Ala Asn Asp Met Asn Arg Asn Val Leu Cys Thr Ser Asn
145                 150                 155                 160
Pro Tyr Glu Ser Gln Leu His Ala Glu Ala Tyr Glu Trp Ala Lys Lys
                165                 170                 175
Ile Ser Glu His Leu Leu Pro Arg Thr Arg Ala Tyr Ala Glu Ile Trp
                180                 185                 190
Leu Asp Gln Glu Lys Val Ala Thr Thr Asp Glu Pro Ile Leu Gly
                195                 200                 205
Gln Thr Tyr Leu Pro Arg Lys Phe Lys Thr Thr Val Ile Pro Pro
            210                 215                 220
Gln Asn Asp Ile Asp Leu His Ala Asn Asp Met Asn Phe Val Ala Ile
225                 230                 235                 240
Ala Glu Asn Gly Lys Leu Val Gly Phe Asn Leu Leu Val Gly Gly Gly
                245                 250                 255
Leu Ser Ile Glu His Gly Asn Lys Lys Thr Tyr Ala Arg Thr Ala Ser
            260                 265                 270
Glu Phe Gly Tyr Leu Pro Leu Glu His Thr Leu Ala Val Ala Glu Ala
            275                 280                 285
Val Val Thr Thr Gln Arg Asp Trp Gly Asn Arg Thr Asp Arg Lys Asn
            290                 295                 300
Ala Lys Thr Lys Tyr Thr Leu Glu Arg Val Gly Val Glu Thr Phe Lys
305                 310                 315                 320
Ala Glu Val Glu Arg Arg Ala Gly Ile Lys Phe Glu Pro Ile Arg Pro
                325                 330                 335
Tyr Glu Phe Thr Gly Arg Gly Asp Arg Ile Gly Trp Val Lys Gly Ile
            340                 345                 350
Asp Asp Asn Trp His Leu Thr Leu Phe Ile Glu Asn Gly Arg Ile Leu
            355                 360                 365
Asp Tyr Pro Ala Arg Pro Leu Lys Thr Gly Leu Leu Glu Ile Ala Lys
            370                 375                 380
Ile His Lys Gly Asp Phe Arg Ile Thr Ala Asn Gln Asn Leu Ile Ile
385                 390                 395                 400
Ala Gly Val Pro Glu Ser Glu Lys Ala Lys Ile Glu Lys Ile Ala Lys
                405                 410                 415
Glu Ser Gly Leu Met Asn Ala Val Thr Pro Gln Arg Glu Asn Ser Met
            420                 425                 430
Ala Cys Val Ser Phe Pro Thr Cys Pro Leu Ala Met Ala Glu Ala Glu
            435                 440                 445
Arg Phe Leu Pro Ser Phe Ile Asp Asn Ile Asp Asn Leu Met Ala Lys
            450                 455                 460
His Gly Val Ser Asp Glu His Ile Val Met Arg Val Thr Gly Cys Pro
465                 470                 475                 480
Asn Gly Cys Gly Arg Ala Met Leu Ala Glu Val Gly Leu Val Gly Lys
                485                 490                 495
Ala Pro Gly Arg Tyr Asn Leu His Leu Gly Gly Asn Arg Ile Gly Thr
            500                 505                 510
```

```
Arg Ile Pro Arg Met Tyr Lys Glu Asn Ile Thr Glu Pro Glu Ile Leu
            515                 520                 525

Ala Ser Leu Asp Glu Leu Ile Gly Arg Trp Ala Lys Glu Arg Glu Ala
        530                 535                 540

Gly Glu Gly Phe Gly Asp Phe Thr Val Arg Ala Gly Ile Ile Arg Pro
545                 550                 555                 560

Val Leu Asp Pro Ala Arg Asp Leu Trp Asp
                565                 570

<210> SEQ ID NO 45
<211> LENGTH: 1722
<212> TYPE: DNA
<213> ORGANISM: Pantoea ananatis
<220> FEATURE:
<221> NAME/KEY: CDS
<222> LOCATION: (1)..(1722)

<400> SEQUENCE: 45 atg act gaa aaa tac cct ggc ccg ctg gtg gtt gaa ggc aaa ctc acc      48
Met Thr Glu Lys Tyr Pro Gly Pro Leu Val Val Glu Gly Lys Leu Thr
1               5                   10                  15 gac gct gag cgt tta aaa aaa gag agc aac tac ctg cgc ggt acc atc      96
Asp Ala Glu Arg Leu Lys Lys Glu Ser Asn Tyr Leu Arg Gly Thr Ile
                20                  25                  30 ctt gag gac ctc gac gag ggc ctg acc ggt ggt ttc agc ggc gat aac     144
Leu Glu Asp Leu Asp Glu Gly Leu Thr Gly Gly Phe Ser Gly Asp Asn
            35                  40                  45 ttc ctg ctg atc cgt ttt cac ggc atg tac cag cag gat gac cgc gat     192
Phe Leu Leu Ile Arg Phe His Gly Met Tyr Gln Gln Asp Asp Arg Asp
        50                  55                  60 att cgt gct gaa cgt gcg gag caa aaa ctt gag cct cgc cat gcg atg     240
Ile Arg Ala Glu Arg Ala Glu Gln Lys Leu Glu Pro Arg His Ala Met
65                  70                  75                  80 atg ctg cgc tgt cgt ctg ccg ggc ggg atc att acg ccg acc cag tgg     288
Met Leu Arg Cys Arg Leu Pro Gly Gly Ile Ile Thr Pro Thr Gln Trp
                85                  90                  95 ctg gcg att gat aaa ttt gct acc gat aaa acc ctt tac ggc agc atc     336
Leu Ala Ile Asp Lys Phe Ala Thr Asp Lys Thr Leu Tyr Gly Ser Ile
                100                 105                 110 cgt ttg acc aac cgt cag act ttc cag ttt cac ggc att ctg aag aag     384
Arg Leu Thr Asn Arg Gln Thr Phe Gln Phe His Gly Ile Leu Lys Lys
            115                 120                 125 aac gtg aag cct acg cac cag atg ctg cac gaa gtg ggg ctg gat gcg     432
Asn Val Lys Pro Thr His Gln Met Leu His Glu Val Gly Leu Asp Ala
        130                 135                 140 ctg gcg acc gcg aat gac gtt aac cgt aac gtc ctc tgc acc tca aac     480
Leu Ala Thr Ala Asn Asp Val Asn Arg Asn Val Leu Cys Thr Ser Asn
145                 150                 155                 160 cca gtg gag tct gag ttg cat cag gaa gcc tat gag tgg gcc aaa aag     528
Pro Val Glu Ser Glu Leu His Gln Glu Ala Tyr Glu Trp Ala Lys Lys
                165                 170                 175 ctg tcg gag cat ctg ctg ccg caa acc cgc gct tat gcc gag atc tgg     576
Leu Ser Glu His Leu Leu Pro Gln Thr Arg Ala Tyr Ala Glu Ile Trp
            180                 185                 190 tgg gat cag gaa aaa gtg gcg acc acc gac gaa gag ccg atc ctg ggc     624
Trp Asp Gln Glu Lys Val Ala Thr Thr Asp Glu Glu Pro Ile Leu Gly
        195                 200                 205 cag acc tac ctg ccg cgt aag ttt aaa acc acg gtg gtg att ccg ccg     672
Gln Thr Tyr Leu Pro Arg Lys Phe Lys Thr Thr Val Val Ile Pro Pro
    210                 215                 220
```

```
cat aac gat gtt gat ctg cac gct aac gat ctg aac ttt atc gcg att      720
His Asn Asp Val Asp Leu His Ala Asn Asp Leu Asn Phe Ile Ala Ile
225                 230                 235                 240 gcg gaa aac ggc aag ctg gtg ggc ttt aac ctg ctg gtg ggc ggc ggc      768
Ala Glu Asn Gly Lys Leu Val Gly Phe Asn Leu Leu Val Gly Gly Gly
                245                 250                 255 ttg tct atc gag cac ggt aat aaa gcc acc tat gcg cgc acc gcc agc      816
Leu Ser Ile Glu His Gly Asn Lys Ala Thr Tyr Ala Arg Thr Ala Ser
260                 265                 270 gaa ttt ggc tac ttc ccg gtc gat aag atc ctg gat gtg gca gcg gcg      864
Glu Phe Gly Tyr Phe Pro Val Asp Lys Ile Leu Asp Val Ala Ala Ala
        275                 280                 285 gta gtg acg acg cag cgc gac tgg ggc aac cgt acc gat cgt aaa aac      912
Val Val Thr Thr Gln Arg Asp Trp Gly Asn Arg Thr Asp Arg Lys Asn
290                 295                 300 gcc aaa acc aaa tac acg ctg gaa cgc gta ggc gta gag acg ttt aag      960
Ala Lys Thr Lys Tyr Thr Leu Glu Arg Val Gly Val Glu Thr Phe Lys
305                 310                 315                 320 gcg gaa gtc gag aag cgc gcc ggt gtc acg ttt gca ccg aca cgt cct     1008
Ala Glu Val Glu Lys Arg Ala Gly Val Thr Phe Ala Pro Thr Arg Pro
                325                 330                 335 tac gaa ttc acc acc cgt ggc gat cgc att ggc tgg atc aag ggc att     1056
Tyr Glu Phe Thr Thr Arg Gly Asp Arg Ile Gly Trp Ile Lys Gly Ile
                340                 345                 350 gat aac aag tgg cat ctg act ctg ttc atc gaa aac ggt cgt ctg ctg     1104
Asp Asn Lys Trp His Leu Thr Leu Phe Ile Glu Asn Gly Arg Leu Leu
355                 360                 365 gat tat ccg gga cgt ccg ctg aaa agc ggc gtg gcg gaa atc gcc aaa     1152
Asp Tyr Pro Gly Arg Pro Leu Lys Ser Gly Val Ala Glu Ile Ala Lys
        370                 375                 380 atc cat cag ggc gat ttc cgt ctg acc gcc aac cag aac ctg att gtg     1200
Ile His Gln Gly Asp Phe Arg Leu Thr Ala Asn Gln Asn Leu Ile Val
385                 390                 395                 400 gca ggc gtg ccg gaa agc caa aaa gcg cag att gaa gcg att gcc cgc     1248
Ala Gly Val Pro Glu Ser Gln Lys Ala Gln Ile Glu Ala Ile Ala Arg
                405                 410                 415 gaa cac ggt ctg atg gaa aac gtg acg gcc cag cgg gaa aac tcg atg     1296
Glu His Gly Leu Met Glu Asn Val Thr Ala Gln Arg Glu Asn Ser Met
            420                 425                 430 gcc tgc gtg gcg ttt cca acc tgt ccg ctg gcg atg gcg gag gct gaa     1344
Ala Cys Val Ala Phe Pro Thr Cys Pro Leu Ala Met Ala Glu Ala Glu
                435                 440                 445 cgt ttt ctg ccg tct ttc gtg acg aaa gtc gaa gag atc atg cac agc     1392
Arg Phe Leu Pro Ser Phe Val Thr Lys Val Glu Glu Ile Met His Ser
450                 455                 460 cat ggc gta ggc gaa gag cac ata gtg tta cgc gtt acc ggt tgt ccg     1440
His Gly Val Gly Glu Glu His Ile Val Leu Arg Val Thr Gly Cys Pro
465                 470                 475                 480 aac ggc tgt ggc cgt gcc atg ctg gca gaa gtg ggc ctg gtg ggg aaa     1488
Asn Gly Cys Gly Arg Ala Met Leu Ala Glu Val Gly Leu Val Gly Lys
                485                 490                 495 gcg ccg ggc cgt tac aac ctg cat atc ggg ggt aac cgc atc gga acg     1536
Ala Pro Gly Arg Tyr Asn Leu His Ile Gly Gly Asn Arg Ile Gly Thr
        500                 505                 510 cgc att cca cgt atg tat cgc gaa aat att act gaa agt gaa att ctc     1584
Arg Ile Pro Arg Met Tyr Arg Glu Asn Ile Thr Glu Ser Glu Ile Leu
515                 520                 525 gcc aca ctt gat gag ctg gta ggt cgc tgg gcg aaa gag cgc gag gcc     1632
Ala Thr Leu Asp Glu Leu Val Gly Arg Trp Ala Lys Glu Arg Glu Ala
```

```
                530             535             540
gca gaa ggc ttt ggt gac ttc gtg att cgg gct ggc att gtt acg ccg    1680
Ala Glu Gly Phe Gly Asp Phe Val Ile Arg Ala Gly Ile Val Thr Pro
545                 550                 555                 560 gtg ttg gat cct gcg cgc gac ttc tgg cag gag gca aaa tga            1722
Val Leu Asp Pro Ala Arg Asp Phe Trp Gln Glu Ala Lys
                565                 570
```

<210> SEQ ID NO 46
<211> LENGTH: 573
<212> TYPE: PRT
<213> ORGANISM: Pantoea ananatis

<400> SEQUENCE: 46

```
Met Thr Glu Lys Tyr Pro Gly Pro Leu Val Glu Gly Lys Leu Thr
1               5                   10                  15

Asp Ala Glu Arg Leu Lys Lys Glu Ser Asn Tyr Leu Arg Gly Thr Ile
                20                  25                  30

Leu Glu Asp Leu Asp Glu Gly Leu Thr Gly Gly Phe Ser Gly Asp Asn
            35                  40                  45

Phe Leu Leu Ile Arg Phe His Gly Met Tyr Gln Gln Asp Asp Arg Asp
50                  55                  60

Ile Arg Ala Glu Arg Ala Glu Gln Lys Leu Glu Pro Arg His Ala Met
65                  70                  75                  80

Met Leu Arg Cys Arg Leu Pro Gly Gly Ile Ile Thr Pro Thr Gln Trp
                85                  90                  95

Leu Ala Ile Asp Lys Phe Ala Thr Asp Lys Thr Leu Tyr Gly Ser Ile
            100                 105                 110

Arg Leu Thr Asn Arg Gln Thr Phe Gln Phe His Gly Ile Leu Lys Lys
        115                 120                 125

Asn Val Lys Pro Thr His Gln Met Leu His Glu Val Gly Leu Asp Ala
130                 135                 140

Leu Ala Thr Ala Asn Asp Val Asn Arg Asn Val Leu Cys Thr Ser Asn
145                 150                 155                 160

Pro Val Glu Ser Glu Leu His Gln Glu Ala Tyr Glu Trp Ala Lys Lys
                165                 170                 175

Leu Ser Glu His Leu Leu Pro Gln Thr Arg Ala Tyr Ala Glu Ile Trp
            180                 185                 190

Trp Asp Gln Glu Lys Val Ala Thr Thr Asp Glu Pro Ile Leu Gly
        195                 200                 205

Gln Thr Tyr Leu Pro Arg Lys Phe Lys Thr Thr Val Val Ile Pro Pro
210                 215                 220

His Asn Asp Val Asp Leu His Ala Asn Asp Leu Asn Phe Ile Ala Ile
225                 230                 235                 240

Ala Glu Asn Gly Lys Leu Val Gly Phe Asn Leu Leu Val Gly Gly Gly
                245                 250                 255

Leu Ser Ile Glu His Gly Asn Lys Ala Thr Tyr Ala Arg Thr Ala Ser
            260                 265                 270

Glu Phe Gly Tyr Phe Pro Val Asp Lys Ile Leu Asp Val Ala Ala Ala
        275                 280                 285

Val Val Thr Thr Gln Arg Asp Trp Gly Asn Arg Thr Asp Arg Lys Asn
290                 295                 300

Ala Lys Thr Lys Tyr Thr Leu Glu Arg Val Gly Val Glu Thr Phe Lys
305                 310                 315                 320

Ala Glu Val Glu Lys Arg Ala Gly Val Thr Phe Ala Pro Thr Arg Pro
```

```
                   325                 330                 335
Tyr Glu Phe Thr Thr Arg Gly Asp Arg Ile Gly Trp Ile Lys Gly Ile
            340                 345                 350

Asp Asn Lys Trp His Leu Thr Leu Phe Ile Glu Asn Gly Arg Leu Leu
        355                 360                 365

Asp Tyr Pro Gly Arg Pro Leu Lys Ser Gly Val Ala Glu Ile Ala Lys
    370                 375                 380

Ile His Gln Gly Asp Phe Arg Leu Thr Ala Asn Gln Asn Leu Ile Val
385                 390                 395                 400

Ala Gly Val Pro Glu Ser Gln Lys Ala Gln Ile Glu Ala Ile Ala Arg
                405                 410                 415

Glu His Gly Leu Met Glu Asn Val Thr Ala Gln Arg Glu Asn Ser Met
            420                 425                 430

Ala Cys Val Ala Phe Pro Thr Cys Pro Leu Ala Met Ala Glu Ala Glu
        435                 440                 445

Arg Phe Leu Pro Ser Phe Val Thr Lys Val Glu Glu Ile Met His Ser
    450                 455                 460

His Gly Val Gly Glu Glu His Ile Val Leu Arg Val Thr Gly Cys Pro
465                 470                 475                 480

Asn Gly Cys Gly Arg Ala Met Leu Ala Glu Val Gly Leu Val Gly Lys
                485                 490                 495

Ala Pro Gly Arg Tyr Asn Leu His Ile Gly Gly Asn Arg Ile Gly Thr
            500                 505                 510

Arg Ile Pro Arg Met Tyr Arg Glu Asn Ile Thr Glu Ser Glu Ile Leu
        515                 520                 525

Ala Thr Leu Asp Glu Leu Val Gly Arg Trp Ala Lys Glu Arg Glu Ala
    530                 535                 540

Ala Glu Gly Phe Gly Asp Phe Val Ile Arg Ala Gly Ile Val Thr Pro
545                 550                 555                 560

Val Leu Asp Pro Ala Arg Asp Phe Trp Gln Glu Ala Lys
                565                 570

<210> SEQ ID NO 47
<211> LENGTH: 1374
<212> TYPE: DNA
<213> ORGANISM: Escherichia coli
<220> FEATURE:
<221> NAME/KEY: CDS
<222> LOCATION: (1)..(1374)

<400> SEQUENCE: 47 gtg gat cat ttg cct ata ttt tgc caa tta cgc gat cgc gac tgt ctg      48
Met Asp His Leu Pro Ile Phe Cys Gln Leu Arg Asp Arg Asp Cys Leu
1               5                   10                  15 att gtc ggc ggt ggt gat gtc gcg gaa cgc aaa gca agg ttg ctg tta      96
Ile Val Gly Gly Gly Asp Val Ala Glu Arg Lys Ala Arg Leu Leu Leu
            20                  25                  30 gac gca ggc gct cgc tta acg gtg aat gca tta gcg ttt att cca cag     144
Asp Ala Gly Ala Arg Leu Thr Val Asn Ala Leu Ala Phe Ile Pro Gln
        35                  40                  45 ttc acc gca tgg gca gat gca ggc atg tta acc ctc gtc gaa ggg cca     192
Phe Thr Ala Trp Ala Asp Ala Gly Met Leu Thr Leu Val Glu Gly Pro
    50                  55                  60 ttt gat gaa agc ctt ctc gac acc tgc tgg ctg gcg att gca gcg acg     240
Phe Asp Glu Ser Leu Leu Asp Thr Cys Trp Leu Ala Ile Ala Ala Thr
65                  70                  75                  80 gat gat gac gcg ctt aac cag cgc gtc agc gaa gcc gct gaa gct cgt     288
```

```
                Asp Asp Asp Ala Leu Asn Gln Arg Val Ser Glu Ala Ala Glu Ala Arg
                            85                  90                  95 cgc atc ttc tgt aac gtg gtc gat gcg ccg aaa gcc gcc agc ttt att          336
Arg Ile Phe Cys Asn Val Val Asp Ala Pro Lys Ala Ala Ser Phe Ile
                100                 105                 110 atg ccg tcg att att gac cgc tca ccg ctc atg gta gcg gtc tcc tct          384
Met Pro Ser Ile Ile Asp Arg Ser Pro Leu Met Val Ala Val Ser Ser
                115                 120                 125 ggc ggc acc tct ccg gtt ctg gca cgc ctg ttg cgc gaa aaa ctt gaa          432
Gly Gly Thr Ser Pro Val Leu Ala Arg Leu Leu Arg Glu Lys Leu Glu
            130                 135                 140 tca ctg ctg ccg tta cat ctg ggc cag gta gcg aaa tac gcc ggg caa          480
Ser Leu Leu Pro Leu His Leu Gly Gln Val Ala Lys Tyr Ala Gly Gln
145                 150                 155                 160 tta cgc ggg cga gtg aaa caa cag ttc gcc acg atg ggt gag cgt cgc          528
Leu Arg Gly Arg Val Lys Gln Gln Phe Ala Thr Met Gly Glu Arg Arg
                165                 170                 175 cgt ttc tgg gag aaa ttg ttc gtt aac gac cgc ctg gcg cag tcg ctg          576
Arg Phe Trp Glu Lys Leu Phe Val Asn Asp Arg Leu Ala Gln Ser Leu
                180                 185                 190 gca aac aac gat cag aaa gcc att act gaa acg acc gaa cag tta atc          624
Ala Asn Asn Asp Gln Lys Ala Ile Thr Glu Thr Thr Glu Gln Leu Ile
                195                 200                 205 aac gaa ccg ctc gac cat cgc ggt gaa gtg gtg ctg gtt ggt gca ggt          672
Asn Glu Pro Leu Asp His Arg Gly Glu Val Val Leu Val Gly Ala Gly
210                 215                 220 ccg ggc gat gcc ggg ctg ctg aca ctg aaa gga ctg caa caa att cag          720
Pro Gly Asp Ala Gly Leu Leu Thr Leu Lys Gly Leu Gln Gln Ile Gln
225                 230                 235                 240 cag gca gat gtg gtg gtc tac gac cgt ctg gtt tct gac gat att atg          768
Gln Ala Asp Val Val Val Tyr Asp Arg Leu Val Ser Asp Asp Ile Met
                245                 250                 255 aat ctg gta cgc cgc gat gcg gac cgt gtt ttc gtc ggc aaa cgc gcg          816
Asn Leu Val Arg Arg Asp Ala Asp Arg Val Phe Val Gly Lys Arg Ala
                260                 265                 270 gga tac cac tgc gta ccc cag gaa gag att aac cag atc ctg ctg cgg          864
Gly Tyr His Cys Val Pro Gln Glu Glu Ile Asn Gln Ile Leu Leu Arg
                275                 280                 285 gaa gcg caa aaa ggc aaa cgc gtg gtg cgg ctg aaa ggt ggc gat ccg          912
Glu Ala Gln Lys Gly Lys Arg Val Val Arg Leu Lys Gly Gly Asp Pro
290                 295                 300 ttt att ttt ggc cgt ggt ggc gaa gag ctg gaa aca ctg tgc aac gcg          960
Phe Ile Phe Gly Arg Gly Gly Glu Glu Leu Glu Thr Leu Cys Asn Ala
305                 310                 315                 320 ggt att ccg ttc tcg gtg gtt ccg ggt att acc gca gct tct ggt tgc         1008
Gly Ile Pro Phe Ser Val Val Pro Gly Ile Thr Ala Ala Ser Gly Cys
                325                 330                 335 tct gcc tat tcg ggt att cca ctc acg cat cgc gat tat gcc cag agc         1056
Ser Ala Tyr Ser Gly Ile Pro Leu Thr His Arg Asp Tyr Ala Gln Ser
                340                 345                 350 gta cgc tta att acc gga cac tta aaa acc ggt ggc gag ctg gac tgg         1104
Val Arg Leu Ile Thr Gly His Leu Lys Thr Gly Gly Glu Leu Asp Trp
                355                 360                 365 gaa aac ctg gcg gca gaa aaa cag acg ctg gtg ttc tat atg ggg ttg         1152
Glu Asn Leu Ala Ala Glu Lys Gln Thr Leu Val Phe Tyr Met Gly Leu
                370                 375                 380 aat cag gcc gcg act att cag caa aag ctg att gaa cac gga atg cca         1200
Asn Gln Ala Ala Thr Ile Gln Gln Lys Leu Ile Glu His Gly Met Pro
385                 390                 395                 400
```

| | | | | | | | | | | | | | | | | |
|---|---|---|---|---|---|---|---|---|---|---|---|---|---|---|---|---|
|ggc|gaa|atg|ccg|gtg|gca|att|gtc|gaa|aac|ggt|acg|gca|gtc|acg|cag||1248|
|Gly|Glu|Met|Pro|Val|Ala|Ile|Val|Glu|Asn|Gly|Thr|Ala|Val|Thr|Gln||
| | | |405| | | | |410| | | | |415| | | |

| | | | | | | | | | | | | | | | | |
|---|---|---|---|---|---|---|---|---|---|---|---|---|---|---|---|---|
|cgc|gtg|att|gac|ggt|acg|ctc|aca|cag|ctg|gga|gaa|ctg|gcg|cag|caa||1296|
|Arg|Val|Ile|Asp|Gly|Thr|Leu|Thr|Gln|Leu|Gly|Glu|Leu|Ala|Gln|Gln||
| | | |420| | | | |425| | | | |430| | | |

| | | | | | | | | | | | | | | | | |
|---|---|---|---|---|---|---|---|---|---|---|---|---|---|---|---|---|
|atg|aac|agt|cca|tcg|cta|att|att|att|ggt|cgg|gtt|gtt|ggc|ctg|cgc||1344|
|Met|Asn|Ser|Pro|Ser|Leu|Ile|Ile|Ile|Gly|Arg|Val|Val|Gly|Leu|Arg||
| | | |435| | | | |440| | | | |445| | | |

| | | | | | | | | | |
|---|---|---|---|---|---|---|---|---|---|
|gat|aaa|ctg|aac|tgg|ttc|tcc|aac|cat|taa|1374|
|Asp|Lys|Leu|Asn|Trp|Phe|Ser|Asn|His| | |
| | |450| | | | |455| | | |

<210> SEQ ID NO 48
<211> LENGTH: 457
<212> TYPE: PRT
<213> ORGANISM: Escherichia coli

<400> SEQUENCE: 48

Met Asp His Leu Pro Ile Phe Cys Gln Leu Arg Asp Arg Asp Cys Leu
1               5                   10                  15

Ile Val Gly Gly Gly Asp Val Ala Glu Arg Lys Ala Arg Leu Leu Leu
            20                  25                  30

Asp Ala Gly Ala Arg Leu Thr Val Asn Ala Leu Ala Phe Ile Pro Gln
        35                  40                  45

Phe Thr Ala Trp Ala Asp Ala Gly Met Leu Thr Leu Val Glu Gly Pro
    50                  55                  60

Phe Asp Glu Ser Leu Leu Asp Thr Cys Trp Leu Ala Ile Ala Ala Thr
65                  70                  75                  80

Asp Asp Asp Ala Leu Asn Gln Arg Val Ser Glu Ala Ala Glu Ala Arg
                85                  90                  95

Arg Ile Phe Cys Asn Val Val Asp Ala Pro Lys Ala Ala Ser Phe Ile
            100                 105                 110

Met Pro Ser Ile Ile Asp Arg Ser Pro Leu Met Val Ala Val Ser Ser
        115                 120                 125

Gly Gly Thr Ser Pro Val Leu Ala Arg Leu Leu Arg Glu Lys Leu Glu
    130                 135                 140

Ser Leu Leu Pro Leu His Leu Gly Gln Val Ala Lys Tyr Ala Gly Gln
145                 150                 155                 160

Leu Arg Gly Arg Val Lys Gln Gln Phe Ala Thr Met Gly Glu Arg Arg
                165                 170                 175

Arg Phe Trp Glu Lys Leu Phe Val Asn Asp Arg Leu Ala Gln Ser Leu
            180                 185                 190

Ala Asn Asn Asp Gln Lys Ala Ile Thr Glu Thr Thr Glu Gln Leu Ile
        195                 200                 205

Asn Glu Pro Leu Asp His Arg Gly Glu Val Val Leu Val Gly Ala Gly
    210                 215                 220

Pro Gly Asp Ala Gly Leu Leu Thr Leu Lys Gly Leu Gln Gln Ile Gln
225                 230                 235                 240

Gln Ala Asp Val Val Val Tyr Asp Arg Leu Val Ser Asp Asp Ile Met
                245                 250                 255

Asn Leu Val Arg Arg Asp Ala Asp Arg Val Phe Val Gly Lys Arg Ala
            260                 265                 270

Gly Tyr His Cys Val Pro Gln Glu Glu Ile Asn Gln Ile Leu Leu Arg
        275                 280                 285

Glu Ala Gln Lys Gly Lys Arg Val Val Arg Leu Lys Gly Gly Asp Pro

```
                290                 295                 300
Phe Ile Phe Gly Arg Gly Gly Glu Glu Leu Glu Thr Leu Cys Asn Ala
305                 310                 315                 320

Gly Ile Pro Phe Ser Val Val Pro Gly Ile Thr Ala Ala Ser Gly Cys
                325                 330                 335

Ser Ala Tyr Ser Gly Ile Pro Leu Thr His Arg Asp Tyr Ala Gln Ser
            340                 345                 350

Val Arg Leu Ile Thr Gly His Leu Lys Thr Gly Gly Glu Leu Asp Trp
                355                 360                 365

Glu Asn Leu Ala Ala Glu Lys Gln Thr Leu Val Phe Tyr Met Gly Leu
            370                 375                 380

Asn Gln Ala Ala Thr Ile Gln Gln Lys Leu Ile Glu His Gly Met Pro
385                 390                 395                 400

Gly Glu Met Pro Val Ala Ile Val Glu Asn Gly Thr Ala Val Thr Gln
                405                 410                 415

Arg Val Ile Asp Gly Thr Leu Thr Gln Leu Gly Glu Leu Ala Gln Gln
                420                 425                 430

Met Asn Ser Pro Ser Leu Ile Ile Ile Gly Arg Val Val Gly Leu Arg
            435                 440                 445

Asp Lys Leu Asn Trp Phe Ser Asn His
        450                 455

<210> SEQ ID NO 49
<211> LENGTH: 1416
<212> TYPE: DNA
<213> ORGANISM: Pantoea ananatis
<220> FEATURE:
<221> NAME/KEY: CDS
<222> LOCATION: (1)..(1416)

<400> SEQUENCE: 49 gtg gat tat ttg cct ctt ttt gcc gat ctc gca ggt cga ccc gta ctg     48
Met Asp Tyr Leu Pro Leu Phe Ala Asp Leu Ala Gly Arg Pro Val Leu
1               5                   10                  15 gtc gtc ggc ggc gga gat atc gcg gcg cgc aag att gag ctg ctg cgt     96
Val Val Gly Gly Gly Asp Ile Ala Ala Arg Lys Ile Glu Leu Leu Arg
            20                  25                  30 cgg gcc ggg gcg cgc att caa atc gcc tca cgc gaa ctc tgc ccc gag    144
Arg Ala Gly Ala Arg Ile Gln Ile Ala Ser Arg Glu Leu Cys Pro Glu
        35                  40                  45 tta cag gct ttg ctg gat gaa cag cag ctt gaa tgg ctg gcc acg tcc    192
Leu Gln Ala Leu Leu Asp Glu Gln Gln Leu Glu Trp Leu Ala Thr Ser
    50                  55                  60 ttt gaa ccc gct cag ctc gac aag gtc ttt ctg gtc att gcc gct acc    240
Phe Glu Pro Ala Gln Leu Asp Lys Val Phe Leu Val Ile Ala Ala Thr
65                  70                  75                  80 gat gac aat gcg ctg aat gcg cag gtc tat gac gaa gcg aat gcc cgc    288
Asp Asp Asn Ala Leu Asn Ala Gln Val Tyr Asp Glu Ala Asn Ala Arg
                85                  90                  95 cac aag ctg gta aac gtg gta gac gat cag cct aaa tgc agc ttt att    336
His Lys Leu Val Asn Val Val Asp Asp Gln Pro Lys Cys Ser Phe Ile
            100                 105                 110 ttc ccc tct att gtt gat cga tcg cca ctg gtc gtg gcg atc tcc tcc    384
Phe Pro Ser Ile Val Asp Arg Ser Pro Leu Val Val Ala Ile Ser Ser
        115                 120                 125 agt ggc acc gcg ccg gtg ctg gcc cgc atg ctg cgc gag aaa ctc gaa    432
Ser Gly Thr Ala Pro Val Leu Ala Arg Met Leu Arg Glu Lys Leu Glu
    130                 135                 140
```

| | | |
|---|---|---|
| acg ctg ctg cca tcc cat ctg ggc caa atg gcc gag ctg gcg ggt cag<br>Thr Leu Leu Pro Ser His Leu Gly Gln Met Ala Glu Leu Ala Gly Gln<br>145                            150                     155                   160 | | 480 |
| tgg cgt gac aaa gtc aaa gct cgc ttc agc cgt atg tcc gat cgc cgt<br>Trp Arg Asp Lys Val Lys Ala Arg Phe Ser Arg Met Ser Asp Arg Arg<br>                        165                     170                     175 | | 528 |
| cgt tac tgg gaa aga ata ttt aat ggc cgt ttt gcc agt cag atg gcg<br>Arg Tyr Trp Glu Arg Ile Phe Asn Gly Arg Phe Ala Ser Gln Met Ala<br>                  180                     185                     190 | | 576 |
| acg ggc gac gtt acg gcc gct aaa cag acg ctg gat agc gaa ctg ggc<br>Thr Gly Asp Val Thr Ala Ala Lys Gln Thr Leu Asp Ser Glu Leu Gly<br>         195                     200                     205 | | 624 |
| gat cag ccg ccc cga cag ggc gaa att att ctg gtt ggc gcg ggg cct<br>Asp Gln Pro Pro Arg Gln Gly Glu Ile Ile Leu Val Gly Ala Gly Pro<br>210                            215                     220 | | 672 |
| ggc gac agc ggc ctg tta acc ctg cgc gga ctg cag gtg atg cag ctg<br>Gly Asp Ser Gly Leu Leu Thr Leu Arg Gly Leu Gln Val Met Gln Leu<br>225                          230                     235                   240 | | 720 |
| gcg gac gtg gtg ctc tac gat cat ctc gtc agc gat gag gtg ctc gat<br>Ala Asp Val Val Leu Tyr Asp His Leu Val Ser Asp Glu Val Leu Asp<br>                           245                     250                     255 | | 768 |
| ctg gtc cgg cgc gat gcc gat cgt atc tgc gta ggc aag cgt gcc agc<br>Leu Val Arg Arg Asp Ala Asp Arg Ile Cys Val Gly Lys Arg Ala Ser<br>         260                     265                     270 | | 816 |
| gcc cat ctc ctg ccg cag gac gaa att aac cag ttg atg gtg caa ctg<br>Ala His Leu Leu Pro Gln Asp Glu Ile Asn Gln Leu Met Val Gln Leu<br>                  275                     280                     285 | | 864 |
| gcg cag aaa ggc aaa cgt gtg gtg cgc ctt aaa ggc ggc gat ccc ttt<br>Ala Gln Lys Gly Lys Arg Val Val Arg Leu Lys Gly Gly Asp Pro Phe<br>290                            295                     300 | | 912 |
| att ttt ggc cgc ggc ggc gaa gag tta cag gcg gcg gcg caa gcg ggc<br>Ile Phe Gly Arg Gly Gly Glu Glu Leu Gln Ala Ala Ala Gln Ala Gly<br>305                            310                     315                   320 | | 960 |
| att cca ttc cag gtc gtg cct ggc gta acg gcc gcc gca ggg gct acc<br>Ile Pro Phe Gln Val Val Pro Gly Val Thr Ala Ala Ala Gly Ala Thr<br>                         325                     330                     335 | | 1008 |
| gcc tat gct ggc att ccg ctg acg cac cgt gat tac gca caa agc gtg<br>Ala Tyr Ala Gly Ile Pro Leu Thr His Arg Asp Tyr Ala Gln Ser Val<br>         340                     345                     350 | | 1056 |
| ctg ttt atc acc gga cac tgc cgt ccg gat ggc gat gat att gac tgg<br>Leu Phe Ile Thr Gly His Cys Arg Pro Asp Gly Asp Asp Ile Asp Trp<br>                  355                     360                     365 | | 1104 |
| cca tcc ctc gcg cgt gcc cgt cag acg ctg gcg att tac atg ggc gct<br>Pro Ser Leu Ala Arg Ala Arg Gln Thr Leu Ala Ile Tyr Met Gly Ala<br>370                            375                     380 | | 1152 |
| gtc aag gcg gct cac atc agc cag cag ctt att ctt cat ggg cgc gcc<br>Val Lys Ala Ala His Ile Ser Gln Gln Leu Ile Leu His Gly Arg Ala<br>385                            390                     395                   400 | | 1200 |
| gcc tca aca ccg gtt gcg gtg att ggg cgc ggt acc cgg ccg gat caa<br>Ala Ser Thr Pro Val Ala Val Ile Gly Arg Gly Thr Arg Pro Asp Gln<br>                         405                     410                     415 | | 1248 |
| cag gta ttg acc ggc aca ctc gaa cat ctg gag acg ctg gca gcg tca<br>Gln Val Leu Thr Gly Thr Leu Glu His Leu Glu Thr Leu Ala Ala Ser<br>                  420                     425                     430 | | 1296 |
| gcg cct tcc ccg gcc ctg ctg gtg att ggg gaa gtg gtt aat tta cac<br>Ala Pro Ser Pro Ala Leu Leu Val Ile Gly Glu Val Val Asn Leu His<br>         435                     440                     445 | | 1344 |
| ggg caa ctg gcc tgg ttt cag cat tcg gca cag cag ggg gct cgc gag<br>Gly Gln Leu Ala Trp Phe Gln His Ser Ala Gln Gln Gly Ala Arg Glu<br>450                            455                     460 | | 1392 |

```
tcc gcc gtt gtc aat ctg gct tga                                    1416
Ser Ala Val Val Asn Leu Ala
465                 470
```

<210> SEQ ID NO 50
<211> LENGTH: 471
<212> TYPE: PRT
<213> ORGANISM: Pantoea ananatis

<400> SEQUENCE: 50

| Met | Asp | Tyr | Leu | Pro | Leu | Phe | Ala | Asp | Leu | Ala | Gly | Arg | Pro | Val | Leu |
|---|---|---|---|---|---|---|---|---|---|---|---|---|---|---|---|
| 1 | | | | 5 | | | | | 10 | | | | | 15 | |

| Val | Val | Gly | Gly | Gly | Asp | Ile | Ala | Ala | Arg | Lys | Ile | Glu | Leu | Leu | Arg |
| | | | 20 | | | | | 25 | | | | | 30 | | |

| Arg | Ala | Gly | Ala | Arg | Ile | Gln | Ile | Ala | Ser | Arg | Glu | Leu | Cys | Pro | Glu |
| | | 35 | | | | | 40 | | | | | 45 | | | |

| Leu | Gln | Ala | Leu | Leu | Asp | Glu | Gln | Leu | Glu | Trp | Leu | Ala | Thr | Ser |
| | 50 | | | | | 55 | | | | | 60 | | | | |

| Phe | Glu | Pro | Ala | Gln | Leu | Asp | Lys | Val | Phe | Leu | Val | Ile | Ala | Ala | Thr |
| 65 | | | | | 70 | | | | | 75 | | | | | 80 |

| Asp | Asp | Asn | Ala | Leu | Asn | Ala | Gln | Val | Tyr | Asp | Glu | Ala | Asn | Ala | Arg |
| | | | | 85 | | | | | 90 | | | | | 95 | |

| His | Lys | Leu | Val | Asn | Val | Val | Asp | Asp | Gln | Pro | Lys | Cys | Ser | Phe | Ile |
| | | | 100 | | | | | 105 | | | | | 110 | | |

| Phe | Pro | Ser | Ile | Val | Asp | Arg | Ser | Pro | Leu | Val | Val | Ala | Ile | Ser | Ser |
| | | 115 | | | | | 120 | | | | | 125 | | | |

| Ser | Gly | Thr | Ala | Pro | Val | Leu | Ala | Arg | Met | Leu | Arg | Glu | Lys | Leu | Glu |
| | 130 | | | | | 135 | | | | | 140 | | | | |

| Thr | Leu | Leu | Pro | Ser | His | Leu | Gly | Gln | Met | Ala | Glu | Leu | Ala | Gly | Gln |
| 145 | | | | | 150 | | | | | 155 | | | | | 160 |

| Trp | Arg | Asp | Lys | Val | Lys | Ala | Arg | Phe | Ser | Arg | Met | Ser | Asp | Arg | Arg |
| | | | | 165 | | | | | 170 | | | | | 175 | |

| Arg | Tyr | Trp | Glu | Arg | Ile | Phe | Asn | Gly | Arg | Phe | Ala | Ser | Gln | Met | Ala |
| | | | 180 | | | | | 185 | | | | | 190 | | |

| Thr | Gly | Asp | Val | Thr | Ala | Ala | Lys | Gln | Thr | Leu | Asp | Ser | Glu | Leu | Gly |
| | | 195 | | | | | 200 | | | | | 205 | | | |

| Asp | Gln | Pro | Pro | Arg | Gln | Gly | Glu | Ile | Ile | Leu | Val | Gly | Ala | Gly | Pro |
| | 210 | | | | | 215 | | | | | 220 | | | | |

| Gly | Asp | Ser | Gly | Leu | Leu | Thr | Leu | Arg | Gly | Leu | Gln | Val | Met | Gln | Leu |
| 225 | | | | | 230 | | | | | 235 | | | | | 240 |

| Ala | Asp | Val | Val | Leu | Tyr | Asp | His | Leu | Val | Ser | Asp | Glu | Val | Leu | Asp |
| | | | | 245 | | | | | 250 | | | | | 255 | |

| Leu | Val | Arg | Arg | Asp | Ala | Asp | Arg | Ile | Cys | Val | Gly | Lys | Arg | Ala | Ser |
| | | | 260 | | | | | 265 | | | | | 270 | | |

| Ala | His | Leu | Leu | Pro | Gln | Asp | Glu | Ile | Asn | Gln | Leu | Met | Val | Gln | Leu |
| | | 275 | | | | | 280 | | | | | 285 | | | |

| Ala | Gln | Lys | Gly | Lys | Arg | Val | Val | Arg | Leu | Lys | Gly | Gly | Asp | Pro | Phe |
| | 290 | | | | | 295 | | | | | 300 | | | | |

| Ile | Phe | Gly | Arg | Gly | Gly | Glu | Glu | Leu | Gln | Ala | Ala | Gln | Ala | Gly |
| 305 | | | | | 310 | | | | | 315 | | | | | 320 |

| Ile | Pro | Phe | Gln | Val | Val | Pro | Gly | Val | Thr | Ala | Ala | Gly | Ala | Thr |
| | | | | 325 | | | | | 330 | | | | | 335 | |

| Ala | Tyr | Ala | Gly | Ile | Pro | Leu | Thr | His | Arg | Asp | Tyr | Ala | Gln | Ser | Val |
| | | | 340 | | | | | 345 | | | | | 350 | | |

```
Leu Phe Ile Thr Gly His Cys Arg Pro Asp Gly Asp Ile Asp Trp
    355                 360                 365

Pro Ser Leu Ala Arg Ala Arg Gln Thr Leu Ala Ile Tyr Met Gly Ala
    370                 375                 380

Val Lys Ala Ala His Ile Ser Gln Gln Leu Ile Leu His Gly Arg Ala
385                 390                 395                 400

Ala Ser Thr Pro Val Ala Val Ile Gly Arg Gly Thr Arg Pro Asp Gln
                405                 410                 415

Gln Val Leu Thr Gly Thr Leu Glu His Leu Glu Thr Leu Ala Ala Ser
            420                 425                 430

Ala Pro Ser Pro Ala Leu Leu Val Ile Gly Glu Val Val Asn Leu His
            435                 440                 445

Gly Gln Leu Ala Trp Phe Gln His Ser Ala Gln Gln Gly Ala Arg Glu
    450                 455                 460

Ser Ala Val Val Asn Leu Ala
465             470

<210> SEQ ID NO 51
<211> LENGTH: 146
<212> TYPE: DNA
<213> ORGANISM: Escherichia coli

<400> SEQUENCE: 51
aaaacgtgag gaaatacctg gattttcct ggttattttg ccgcaggtca gcgtatcgtg      60
aacatctttt ccagtgttca gtagggtgcc ttgcacggta attatgtcac tggttattaa    120 ccaattttc ctgggataa atgagc                                           146

<210> SEQ ID NO 52
<211> LENGTH: 146
<212> TYPE: DNA
<213> ORGANISM: Escherichia coli

<400> SEQUENCE: 52
aaaacgtgag gaaatacctg gattttcct ggttattttg ccgcaggtca gcgtataatg      60
aagatctttt ccagtgttga caagggtgcc ttgcacggtt ataatgtcac tggttattaa    120 ccaattttc ctgggataa atgagc                                           146
```